US010477355B1

(12) United States Patent
Niranjayan et al.

(10) Patent No.: US 10,477,355 B1
(45) Date of Patent: Nov. 12, 2019

(54) SYSTEM FOR LOCATING USERS

(71) Applicant: AMAZON TECHNOLOGIES, INC., Seattle, WA (US)

(72) Inventors: Somasundaram Niranjayan, Issaquah, WA (US); Patrick Ian McCleary, Seattle, WA (US); Matthew Gregory Bowen, Hudson, MA (US); Nikolai Orlov, Seattle, WA (US); James Stephanick, Seattle, WA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 2 days.

(21) Appl. No.: 15/841,216

(22) Filed: Dec. 13, 2017

(51) Int. Cl.
| | |
|---|---|
| *H04W 4/02* | (2018.01) |
| *G06F 3/01* | (2006.01) |
| *G01S 3/04* | (2006.01) |
| *G06Q 10/08* | (2012.01) |
| *E04F 15/024* | (2006.01) |
| *G06K 17/00* | (2006.01) |

(52) U.S. Cl.
CPC ....... *H04W 4/027* (2013.01); *E04F 15/02405* (2013.01); *G01S 3/046* (2013.01); *G06F 3/011* (2013.01); *G06Q 10/087* (2013.01); *G06K 2017/0045* (2013.01)

(58) Field of Classification Search
CPC ............. H04W 4/027; E04F 15/02405; G06Q 10/087; G06F 3/011; G01S 3/046; G06K 2017/0045
See application file for complete search history.

(56) References Cited

U.S. PATENT DOCUMENTS

| | | | | |
|---|---|---|---|---|
| 5,670,778 | A * | 9/1997 | Smith | G01V 8/22 250/221 |
| 7,225,980 | B2 | 6/2007 | Ku et al. | |
| 7,356,495 | B2 * | 4/2008 | Beigl | G06K 7/10336 340/10.3 |
| 7,949,568 | B2 | 5/2011 | Fano et al. | |
| | | (Continued) | | |

OTHER PUBLICATIONS

"Eroding and Dilating", OpenCV 2.4.13.3 documentation, Oct. 5, 2017. Retrieved from the Internet: <<URL:http://docs.opencv.org/2.4/doc/tutorials/imgproc/erosion_dilatation/erosion_dilatation.html>>.

(Continued)

*Primary Examiner* — Tyler J Lee
(74) *Attorney, Agent, or Firm* — Lindauer Law, PLLC

(57) ABSTRACT

A surface within a facility, such as a floor, is equipped with electromagnetic sensors that generate data indicative of the presence of objects, such as the feet of users, at or close to the floor. The data may also be indicative of cross-coupling resulting from a transfer of an electromagnetic signal by the object, such as from one foot to another of a user. The data is processed to determine presence of individual object representations, such as representing a foot. Information about object representations such as their movement, cross-coupling, physical distance between, or features of the object representation may be determined. This data may be used to maintain the identity of particular object representations, track object representations over time, determine that particular object representations are associated with a single user and so forth. Adjacent object representations may avoid merging by using a top-down cross sectioning technique.

21 Claims, 16 Drawing Sheets

(56) References Cited

U.S. PATENT DOCUMENTS

| | | | |
|---|---|---|---|
| 8,009,864 | B2 | 8/2011 | Linaker et al. |
| 8,138,882 | B2* | 3/2012 | Do .................... G08B 21/0461 |
| | | | 340/5.1 |
| 8,189,855 | B2 | 5/2012 | Opalach et al. |
| 8,401,781 | B2* | 3/2013 | Pazos .................. G01C 21/005 |
| | | | 340/10.1 |
| 8,630,924 | B2 | 1/2014 | Groenevelt et al. |
| 8,880,327 | B2* | 11/2014 | Pazos .................. G01C 21/005 |
| | | | 340/944 |
| 9,043,126 | B2* | 5/2015 | Pazos .................. G01C 21/005 |
| | | | 701/419 |
| 9,077,343 | B2* | 7/2015 | Gong .................... H03K 17/955 |
| 9,235,928 | B2 | 1/2016 | Medioni et al. |
| 9,473,747 | B2 | 10/2016 | Kobres et al. |
| 10,203,669 | B2* | 2/2019 | Jun ........................ G05B 15/02 |
| 2006/0071674 | A1* | 4/2006 | Jean ................... H05B 37/0227 |
| | | | 324/686 |
| 2006/0077172 | A1* | 4/2006 | Fukumoto .............. H04B 13/00 |
| | | | 345/156 |
| 2006/0202832 | A1* | 9/2006 | Reznik ............... G06K 7/10346 |
| | | | 340/572.7 |
| 2006/0267731 | A1* | 11/2006 | Chen ...................... G06Q 10/08 |
| | | | 340/10.1 |
| 2006/0290472 | A1* | 12/2006 | Onderko .............. G06K 7/0008 |
| | | | 340/10.1 |
| 2007/0069021 | A1* | 3/2007 | Elrod ..................... G06K 17/00 |
| | | | 235/451 |
| 2007/0088498 | A1* | 4/2007 | Pazos .................. G01C 21/005 |
| | | | 701/408 |
| 2007/0243942 | A1* | 10/2007 | Elliott ................ A63B 69/3608 |
| | | | 473/220 |
| 2008/0191864 | A1* | 8/2008 | Wolfson .................. G06F 3/011 |
| | | | 340/524 |
| 2010/0149093 | A1* | 6/2010 | Edwards ................. G06F 3/011 |
| | | | 345/156 |
| 2010/0164737 | A1* | 7/2010 | Lu ....................... G07C 9/00158 |
| | | | 340/665 |
| 2011/0011936 | A1 | 1/2011 | Morandi et al. |
| 2011/0300938 | A1* | 12/2011 | Mao ........................ G06F 3/011 |
| | | | 463/36 |
| 2012/0283896 | A1* | 11/2012 | Persaud .................. A63F 13/06 |
| | | | 701/2 |
| 2012/0284132 | A1 | 11/2012 | Kim et al. |
| 2013/0284806 | A1 | 10/2013 | Margalit |
| 2014/0184496 | A1* | 7/2014 | Gribetz ................ G02B 27/017 |
| | | | 345/156 |
| 2015/0086107 | A1 | 3/2015 | Dedeoglu et al. |
| 2015/0262510 | A1* | 9/2015 | Pazos .................. G01C 21/005 |
| | | | 340/8.1 |
| 2015/0282766 | A1* | 10/2015 | Cole ...................... A61B 5/7267 |
| | | | 702/139 |
| 2017/0131690 | A1* | 5/2017 | Asaro ...................... G10L 15/22 |
| 2017/0184387 | A1* | 6/2017 | Lefevre .................. G01B 7/004 |
| 2018/0089475 | A1* | 3/2018 | Hattori ............... G06K 7/10346 |
| 2018/0315007 | A1* | 11/2018 | Kingsford ............ G06Q 10/087 |

OTHER PUBLICATIONS

Asthana, et al., "An Indoor Wireless System for Personalized Shopping Assistance", CiteSeerX, In Proceedings of IEEE Workshop on Mobile Computing Systems and Applications, 1994. Retrieved from the Internet: <URL:http://citeseerx.ist.psu.edu/viewdoc/summary?doi=10.1.1.127.3033>.

Dietz, et al., "DiamondTouch: A Multi-User Touch Technology", Mitsubishi Electric Research Laboratories, TR2003-125, Oct. 2003. Retrieved from Internet: <<URL: http://www.merl.com/publications/docs/TR2003-125.pdf.

Fischer, Dirk, "Capacitive Touch Sensors. Application Fields, technology overview and implementation example", Fujitsu Microelectronics Europe GmbH. V4, Jan. 12, 2010. Retrieved from Internet: <<URL: http://www.fujitsu.com/ downloads/MICRO/fme/articles/fujitsu-whitepaper-capacitive-touch-sensors.pdf>>.

Hasegawa, et al., "Human Body Equivalent Phantom for Analyzing of Surface and Space Propagation in MHz-Band Signal Transmission", Department of Electronics, Kyoto Institute of Technology. Retrievable from Internet: <<http://ieeexplore.ieee.org/document/7481823/>>.

Kalnikaite, et al., "How to Nudge In Situ: Designing Lambent Devices to Deliver Information Salience in Supermarkets", ACM, In proceeding of: UbiComp 2011: Ubiquitous Computing, 13th International Conference, UbiComp 2011, Beijing, China, Sep. 17-21, 2011. Retrieved from Internet: <URL:http://www.researchgate.net/publication/221568350_How_to_nudge_in_Situ_designing_lambent_devices_to_deliver_salient_information_in_supermarkets>.

O'Connor, Todd, "mTouch™ Projected Capacitive Touch Screen Sensing Theory of Operation", Microchip Technology Inc. TB3064. 2010. Retrieved from Internet: <<URL: https://www.microchip.com/stellent/groups/techpub_sg/documents/devicedoc/en550192.pdf>>.

Pop, Cristian, "Introduction to the BodyCom Technology", AN1391, DS01391A, Microchip Technology, Inc., May 2, 2011.

Valtonen, Mikka, "Technologies for Smart Environments: Capacitive User Tracking and Proactive Fuzzy Control", Tampere University of Technology. Publication 1044. 2012. Retrieved from Internet: <<http://dspace.cc.tut.fi/dpub/bitstream/handle/123456789/21002/valtonen.pdf?sequence=3&isAllowed=y>>.

Vu, et al., "Distinguishing Users with Capacitive Touch Communication", WINLAB, Rutgers University, In proceedings of: The 18th Annual International Conference on Mobile Computing and Networking ("MobiCom'12"), Aug. 22-26, 2012, Istanbul, Turkey.

* cited by examiner

SYSTEM FOR LOCATING USERS

BACKGROUND

Retailers, wholesalers, and other product distributors typically maintain an inventory of various items that may be ordered, purchased, leased, borrowed, rented, viewed, and so forth, by clients or customers. For example, an e-commerce website may maintain inventory in a fulfillment center. When a customer orders an item, the item is picked from inventory, routed to a packing station, packed, and shipped to the customer. Likewise, physical stores maintain inventory in customer accessible areas, such as in a shopping area, and customers can pick items from inventory and take them to a cashier for purchase, rental, and so forth.

Many physical stores also maintain inventory in a storage area, fulfillment center, or other facility that can be used to replenish inventory located in the shopping areas or to satisfy orders for items that are placed through other channels (e.g., e-commerce). Other examples of entities that maintain facilities holding inventory include libraries, museums, rental centers, and so forth. In each instance, for an item to be moved from one location to another, it is picked from its current location and transitioned to a new location. It is often desirable to monitor quantity or movement of users, inventory, or other objects within the facility.

Other types of facilities may also benefit from the locating of users or other objects. For example, hospitals may wish to determine the location of patients, airports may wish to know where passengers are, and so forth.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features. The figures are not necessarily drawn to scale, and in some figures, the proportions or other aspects may be exaggerated to facilitate comprehension of particular aspects.

Figure 1:
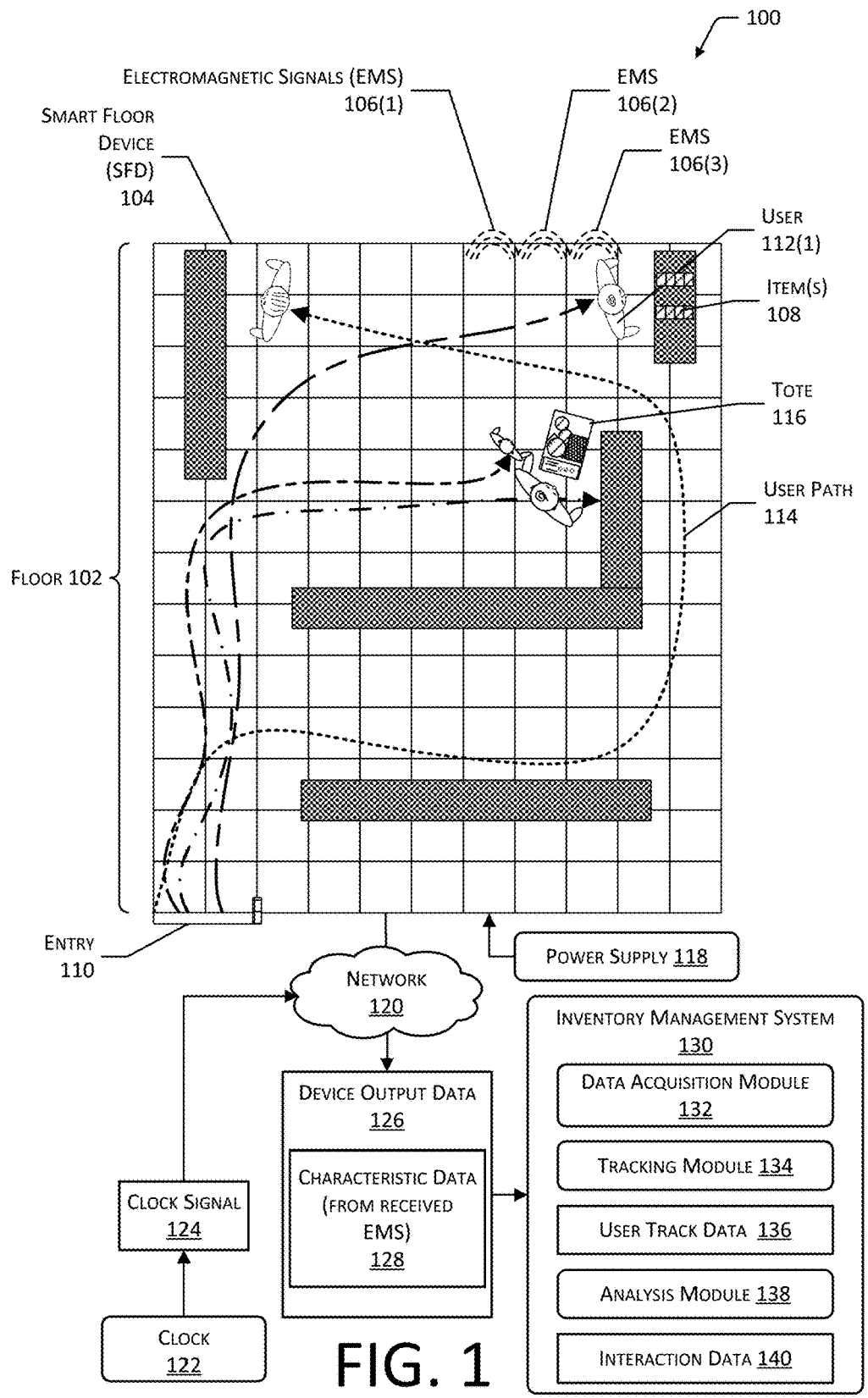
FIG. 1 illustrates a system using signals emitted by smart floor devices to generate user track data about movement of users or other objects within a facility, according to some implementations.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean "including, but not limited to".

DETAILED DESCRIPTION

Described in this disclosure are systems and techniques for generating data in a materials handling facility (facility). The facility may include, or have access to, an inventory management system. The inventory management system may be configured to maintain information about items, users, condition of the facility, and so forth. For example, the inventory management system may maintain data indicative of a number of items at a particular fixture, what items a particular user is ordered to pick, how many items have been picked or placed at the fixture, requests for assistance, environmental status of the facility, and so forth.

Operation of the facility may be facilitated by using one or more sensors to acquire information about interactions in the facility. The inventory management system may process data from the one or more sensors to determine tracking data, interaction data, and so forth. The tracking data provides information about the location of a user within the facility at particular times, their path through the facility, and so forth. The interaction data is indicative of an action such as picking or placing an item at a particular location on the fixture, touching an item at a particular location on the fixture, presence of the user at the fixture without touching the item, and so forth. For example, the inventory management system may use the data to generate tracking data and interaction data that determines a type of item that a user picked from a particular fixture.

A fixture may include one or more item stowage areas such as shelves, hangers, and so forth, that hold or otherwise support a type of item. The fixture may be arranged into sections, such as lanes on a shelf. For example, a shelf may have three lanes, with each lane holding a different type of item. Items may be added to (placed) or removed (picked) from the fixture, moved from one fixture to another, and so forth.

The floor or other surfaces of the facility may comprise a plurality of smart floor devices. For ease of illustration and not necessarily as a limitation, the systems and techniques are described herein with respect to a floor, but may also be used on other surfaces such as shelves, walls, tables, counters, and so forth.

The smart floor devices may include one or more transmitters that generate electromagnetic signals (EMS) and one or more receivers that detect the EMS. For example, a carrier frequency of these signals may be less than or equal to 30 MHz. Each smart floor device may include a plurality of segments. In some implementations, a segment may be configurable to transmit or receive signals from a particular antenna. For example, the smart floor device may comprise 16 segments. At a given time, an antenna at a particular segment may be used to transmit or receive a signal.

The floor of the facility may be divided into clusters. A cluster comprises a plurality of segments of the smart floor devices. The size, boundaries, location, and so forth of the cluster may be adjustable. For example, a cluster may comprise a square, rectangle, circle, irregular shape, and so forth. A cluster may include all of the segments of a smart floor device, or just some segments.

The signals from different segments may be differentiated based on various techniques, such as operating at different frequencies, encoding particular information, being transmitted in particular timeslots, and so forth. While the following examples describe the use of timeslots to differentiate, other techniques may be used instead of, or in addition to timeslots to provide information about which segment has produced a particular signal.

During operation of the floor, each segment within the cluster is associated with a particular timeslot. For example, the cluster may exhibit a relative arrangement of a grid having 20 rows and 20 columns, with a total of 400 segments within the cluster. The size of the cluster may be such that the total physical width and length of the cluster is large enough that a single step of a user is contained therein. For example, assuming a stride length of four feet, the cluster may comprise a square that is five feet on a side. A scan pattern describes a sequence in which the respective segments are used to transmit, receive, and so forth. This sequence may then be repeated. For example, the scan pattern may comprise, with respect to an origin at a top-leftmost position, a sequence progressing through the segments left to right to complete a row of segments, then moving to the next row down, progressing through the segments in that next row left to right, and so forth. Thus, the top-leftmost segment may be segment 1 and the bottom rightmost segment may be segment 400 in the cluster of 400 segments. Each segment in the sequence may be associated with a particular timeslot.

The transmissions radiated from a particular segment are scheduled to occur during a particular timeslot. The segment signal is transmitted on the frequency associated with operation of the smart floor devices. Each segment signal within a given smart floor device is transmitted during a different timeslot, or interval of time. Each segment includes at least one antenna that radiates the segment signal assigned to that segment during the timeslot. By determining the timeslot in which a signal has been received, the source segment at a source location that transmitted the signal may be determined, providing device output data that is indicative of the source location with respect to the floor of the source of the signal and the destination.

An object may electromagnetically couple to a proximate antenna in the smart floor device. For example, when a user is standing with their left foot on or above a first segment in a first smart floor device, their left foot electromagnetically couples to the antenna in that segment. As a result of this coupling, signals radiated by the antenna in the first segment are transferred along the body of the user by way of this electromagnetic coupling. Continuing the example, the signals are propagated along the body of the user to the other extremities such as the right foot and both hands.

The body of the user acts as a bridge, providing a signal path along which signals may travel between the first and second smart floor devices. This cross-coupling of signals provides information about which objects on the floor are electromagnetically coupled. For example, the feet of a single user are electromagnetically coupled to one another as the body of the user provides a signal path for the signals transmitted below one foot to pass along the user's body to be re-radiated at the other foot.

A receiver connected to an antenna in a second segment detects the signals that originated at the first segment under the left foot. Meanwhile, the reverse happens with the first segment detecting a second signal that originates from a second segment and passed from the right foot through the user's body to the left foot.

The smart floor devices may generate device output data that includes received characteristic data. The received characteristic data provides information about the signals received and may include other information, such as the received signal strength of those signals, phase information, and so forth. The device output data from the smart floor devices may be acquired at various times, and this device output data may be processed by a server to generate data captures.

The device output data may comprise a sample associated with a particular segment. This particular segment is associated with a particular location on the floor. Each sample may include data indicative of the characteristic data, such as a received signal strength or intensity, information about the segment that originated the signal that was received, and so forth.

The smart floor devices and their constituent segments are arranged in a generally fixed arrangement. As a result, the relative arrangement of particular segments with respect to one another is known. Physical size of smart floor devices and the constituent segments are known. A correspondence between a known physical reference point or origin may be specified. With this information, a particular segment may be associated with a particular physical location in the facility.

The samples acquired at a particular time, such as within a specified time window, may be arranged into a data capture. The data capture may be expressed as a two-dimensional matrix or arrangement of the samples that corresponds to the physical arrangement of the segments on the floor. One or more values of the characteristic data may be provided for each sample. By analogy, the data capture may be thought of as a frame of an image, in which each pixel of the image corresponds to a particular segment and the color of that pixel is represented by a value of the characteristic data.

A tracking system may track users or other objects in the facility by using the information presented in the data captures. For example, as a user walks across the floor, they produce a series of data captures in which their feet are detected by the smart floor. One or more data captures may be processed to determine the presence of one or more object representations (ORs) or "blobs". An OR may comprise a region of one or more samples within the data capture that are adjacent to one another and exhibit values different from surrounding samples. For example, an OR may comprise a region of adjacent samples that have a received signal intensity that exceeds a threshold value. An OR may correspond to an object such as a foot, portion of a foot, wheel on a tote, and so forth.

The tracking system may assign each OR an OR identifier (ID) that is indicative of that particular OR represented in a data capture. In successive data captures, ORs may be determined and then associated with an OR identifier. It is possible that over the successive data captures, the ORs in those data captures that are produced by the same object may exhibit different characteristics. For example, the first OR of a foot that is flat on the floor may be larger and exhibit a greater signal intensity at a local maxima than a second OR representing the same foot later in time when that foot is being held above the floor in mid-stride.

If the ORs in successive data captures are deemed to be the same OR, that is they correspond to the same object such as a foot that is detected by the smart floor, the same OR ID may be assigned to that OR in the successive data captures.

Individual ORs represented in successive data captures may be deemed to be the same OR, that is representing the same object, using one or more techniques. One technique uses continuity of the OR between successive data captures. For example, if the area of the ORs in successive data captures overlap by a threshold amount, the two ORs may be deemed to be the same, and may be assigned the same OR ID. Another technique uses a linear quadratic estimation algorithm, also known as a Kalman filter, to use information from previous data captures to determine a predicted location. If the actual location in a later data capture is within a region of location uncertainty centered on the predicted location, the two ORs may be deemed to be the same, and may be assigned the same OR ID.

In some situations, an object may not be detected by the smart floor during one or more data captures. For example, a user may lift their foot too high above the floor to be detected, a user may climb a ladder, and so forth. Other techniques may be used to determine the OR ID for these unidentified ORs.

One technique to determine the OR ID may utilize an optical flow algorithm to associate the ORs in successive data captures. For example, the Lucas-Kanade algorithm for optical flow estimation may be used to determine a predicted direction vector for the OR. This predicted direction vector may be used to determine a predicted location that is then compared with an actual location of an OR in a data capture acquired at a later time. If the comparison indicates that the actual location is within a region of location uncertainty or other threshold value of the predicted location, the same OR ID from the prior data captures may be associated with the unidentified OR.

Another technique to determine the OR ID of an OR may be to use feature data of the OR. During data captures in which the OR ID is known, those data captures in which the foot of the user is deemed to be touched down may be analyzed to determine features of the foot. For example, a "touched down" foot may be one in which the foot is moving at less than a threshold velocity and the foot is substantially in contact with the floor. The feature data from several touchdown data captures may be used to train a classifier algorithm to associate those particular features with a particular OR ID. In the event the OR ID is lost, such as due to a loss of continuity, the classifier algorithm may be used to process the feature data of an unidentified OR and provide classifier data that is indicative of one or more of the OR ID or a user identifier (ID).

Yet another technique to determine one or more of the OR ID or a user identifier (ID) may be analysis of gait data. The gait data may include information associated with the movement of a particular user, as represented in the data captures. For example, the gait data may be indicative of one or more of timing between steps, stride length, touchdown dwell time, acceleration profile, velocity, and so forth. Historical gait data may be acquired that includes gait data and an association with a particular OR ID or user ID. A comparison may be made between the gait data of one or more unidentified ORs and the historical gait data. If the comparison indicates a match that is within a threshold value, the OR ID or user ID associated with that historical gait data may be associated with the one or more unidentified ORs.

During operation of the system, ORs from different objects may merge. For example, in a crowded situation the foot of one user may touch the foot of another user. As a result, the two ORs representative of their respective feet may merge in a particular data capture. In the event of such a merger, the merged OR may be associated with both of the OR IDs.

In the event of a merger, the data capture may be processed using one or more techniques to suppress or eliminate the merger and reestablish the constituent separate ORs. In one implementation, a dilating kernel algorithm may be applied to the data capture to produce a dilated data capture. The dilating kernel algorithm may have the effect of suppressing or eliminating areas with lower sample values, revealing two or more distinct ORs, each having at least one local maxima. In other implementations other techniques may be used, such as erosion functions, threshold filtering, and so forth. By using these techniques, the tracking of the separate ORs and their respective OR IDs may be maintained.

The tracking system may produce OR track data. The OR track data may include information that indicates one or more OR IDs, an ID confidence value, and information about those ORs at particular times such as cross-coupling data, OR images taken from respective data captures, timestamps associated with this information, and so forth.

The ID confidence value provides an indication of how reliable a particular OR ID is deemed to be. In some situations, the confidence in an OR ID may degrade. For example, a user may climb a ladder, resulting in a discontinuity in the data captures. After stepping back onto the floor, the confidence value of the OR ID may be decreased until other data, such as gait data or feature data is assessed and used to increase the confidence value of the OR ID. In other situations, a single OR may be associated with a plurality of different OR IDs. For example, a first OR and a second OR may merge to form a third OR, and the OR IDs for the first OR and second OR may be associated with the third OR. Continuing the example, the ID confidence value for each of the OR IDs may be 50%.

As described above, during operation of the smart floor, cross-coupling of signals takes place in which an object being tracked may act as a signal path that propagates signals from one segment to another. For example, a signal from a first segment under a left foot may be transferred via the body of the user to a second segment that is under a right foot. The cross-coupling data provides information indicative of this relationship. For example, the cross-coupling data may indicate that OR ID "192" is cross-coupled with OR ID "217", indicating a high likelihood that these ORs are associated with the same object or are associated with two objects that are in close physical proximity or contact. This cross-coupling data may be used to resolve OR ID, associate two OR IDs with the same user ID, and so forth.

The OR track data may be used to generate user track data. The user track data is indicative of the particular OR IDs that are associated with a particular user ID. The user track data may include information such as a location of that user ID at particular times. The user ID is indicative of a particular user that is in the facility. In some implementations the user ID may be assigned and used for that particular user while they are in the facility, and then is removed or reassigned to another user later. In other implementations the user ID may be associated with an actual identity of the user. For example, the user ID may be indicative of "Bob M. Jones".

The OR track data may be processed to determine those OR IDs that are associated with a particular user ID. For example, based on the location of the ORs and cross coupling data, a pair of OR IDs may be associated with a particular user ID. Other information such as gait data, classifier data, and so forth may be used to determine the user ID associated with one or more ORs.

By tracking the individual ORs as they move about the facility, the movement of the user may be determined. For example, a user may enter the facility through an entry. As the user passes through the entry, the ORs representative of their feet are assigned OR IDs and a user ID is associated with those OR IDs. In some implementations the user may provide credentials or may otherwise be identified, and the user ID may be indicative of that particular user and their user account.

As the user walks about the facility, their ORs representing their feet move across the successive data captures and the OR ID is maintained using the continuity and prediction techniques described above. As the user steps in to retrieve an item from a crowded shelf, they come into contact with another user, resulting in a merger of the ORs of their respective feet that is apparent in a few data captures. Dilated data captures are determined for those data captures, and used to separate the ORs, allowing for the OR IDs to be maintained.

Continuing the example, the user moves about the facility and uses a step stool to reach an item on a high shelf. While on the step stool, the user's feet are no longer detectable by the smart floor. Meanwhile, several other users gather around the step stool. As the user steps back onto the floor, a first OR from one foot and a second OR from another foot of that user may be unidentified. The system may look at the feature data obtained from the first OR and determine the OR ID for the first OR. The cross-coupling data provides information that the now identified first OR is coupled to the second OR. Based on this coupling the OR ID of the second OR may be asserted as being the OR ID of the other OR previously coupled to the first OR.

As the ORs and their associated OR IDs are tracked throughout the facility, user track data is provided that is indicative of the location at different times of the user with the user ID associated with those OR IDs. For example, the location of the user may be designated as a geometric center between the centroids of the ORs associated with that user ID.

By using the techniques described herein, operation of the facility may be improved. The user track data providing information about movement of the users in the facility may be used to determine other information such as interaction data. For example, the user track data may provide information that a user with a particular user ID was in front of an inventory location. Changes to the quantity on hand at the inventory location may then be associated with the user ID. As a result, the inventory management system may be able to quickly determine what item a user has interacted with, determine what items to bill that user ID for taking, and so forth.

The user track data may also allow for enhanced services to be provided to the users of the facility. For example, as an authorized user approaches a fixture holding items that is locked, the fixture may be unlocked to provide access to the items held therein.

The tracking system provides various technical advantages including, but not limited to, reductions in bandwidth compared to other sensor methodologies, improved tracking of individual users in congested environments, detection of potential hazards, detection of user incapacity, and so forth.

The system described herein allows for reduced capital expenditures, as well as reduced operating expenditures relative to other sensor methodologies. For example, compared to vision tracking systems, installation of smart floor devices is less expensive and, during operation, requires fewer computational resources, is less prone to failure or environmental interference, and so forth.

The system described herein may be used in other types of facilities, both commercial and non-commercial. For example, the smart floor devices may be installed within a home or care facility. The system may be used to improve user safety by determining the whereabouts of the user, determining if the user has fallen, and so forth. The system may also provide enhanced functionality, such as operating in conjunction with building operation. For example, by tracking the user in the facility, lighting, environmental controls, and so forth, may be controlled based on the location of the user. In this way, overall energy consumption associated with building operation may be reduced.

Illustrative System

FIG. 1 illustrates a system 100 using a variety of sensors to generate user track data and other information within a facility, according to some implementations. The facility includes a floor 102. The floor 102 may comprise a plurality of smart floor devices (SFDs) 104. A group of the SFDs 104 is a cluster. The floor 102 may include a plurality of clusters.

Each of the SFDs 104 may include various components such as antennas, transmitters, receivers, hardware processors, sensors, and so forth. The SFD 104 may itself be subdivided into segments. For example, each segment may comprise a different antenna. The SFD 104 may be configured to transmit and receive electromagnetic signals (EMS) 106. Groups of segments may be designated as clusters. Each segment within the cluster may be associated with a particular timeslot. During operation, the segment of the SFD 104 may transmit at a particular frequency during that particular timeslot. As a result, within the cluster, a particular segment is designated by when the segment transmits at the particular frequency. The clusters may be sized such that the physical boundaries exceed an expected stride length of users. For example, if the expected stride length is four feet, the clusters may be sized as squares that are five feet on a side. Segments are discussed in more detail below with regard to FIG. 4.

The EMS 106 may be transmitted at a low power. For example, the EMS 106 may have a power level of less than 500 microwatts. These EMS 106 may be propagated by the body of a user. For example, the EMS 106 may be propagated along the skin or clothing of the user, traveling from one SFD 104 to another, or from one SFD 104 to another device such as the fixtures. Each SFD 104 may transmit several signals. The transmissions may be continuous or may be made at particular times, using one or more of the antennas of the SFD 104. The different types of signals that may be transmitted are discussed in more detail below with regard to FIG. 4. The SFD 104 is discussed in more detail below with regard to FIG. 5.

Within the facility may be one or more fixtures. The fixture may include shelves, hangers, and so forth, that hold or otherwise support a type of item. The fixture may be arranged into sections, such as lanes on a shelf. For example, a shelf may have three lanes, with each lane holding a different type of item. Items 108 may be added to (placed) or removed (picked) from the fixture, moved from one fixture to another, and so forth. In some implementations, the SFDs 104 may be installed, and the fixtures and other objects may then be installed on the SFDs 104. In other implementations, the fixtures may be installed and then the SFDs 104 may be installed around the fixtures. Some portions of the floor 102 may omit SFDs 104. For example, SFDs 104 may be omitted from around the perimeter of a room, immediately adjacent to a wall, underneath a fixture, and so forth.

An entry 110 provides access for a user 112 to the facility. For example, the entry 110 may comprise a foyer, door, gated entry area, and so forth. In some implementations, an identity of the user 112 may be asserted at the entry 110. For example, the user 112 may provide identification credentials such as swiping a card, carrying a device that transmits or displays authentication credentials, and so forth. The user 112 may move throughout the facility, with movement depicted in this illustration as a user path 114 across the floor 102. The user 112 may use various tools while in the facility, such as a tote 116, pallet jack, and so forth. The tote 116 may include a basket, cart, bin, bag, and so forth. During operation of the facility, users 112 thus move around, picking, placing, or otherwise interacting with items 108 at the fixtures.

The SFDs 104 may obtain electrical power from a power supply 118. For example, the power supply 118 may provide 24 volts direct current (VDC) to one or more of the SFDs 104. The power supply 118 may be configured to obtain power from building mains and then provide conditioned power for use. The SFDs 104 are connected to a network 120. The network 120 allows for communication between SFDs 104 and other devices, such as described below.

A clock 122 may provide a clock signal 124 or other clock data that is transmitted to the SFDs 104 using the network 120. An interface of the SFD 104 is used to receive the clock signal 124. For example, the interface may be a communication interface such as a data network. In some implementations, the clock signal 124 may be distributed via another mechanism, such as by the power supply 118 by way of a power distribution network. For example, the clock signal 124 may be overlaid as an alternating current signal along one or more of the electrical conductors used to supply direct current power to the SFDs 104. In this example, the interface may comprise circuitry coupled to part of the power supply 118 that detects the clock signal 124 and produces an output indicative of or based on the clock signal 124. In some implementations, the clock signal 124 may be omitted, with each SFD 104 synchronizing timing to an adjacent SFD 104, or by recovering timing data from one or more transmitted signals.

One or more processors of the SFDs 104 may generate device output data 126 comprising one or more samples. The device output data 126 may include characteristic data 128. The characteristic data 128 may be indicative of one or more of the received signal strength or amplitude of the signals, the frequency of the received signal, a phase delay relative to a clock signal, timeslot associated with receipt of the received signal, data indicative of the segment used to receive the data, other phase information, and so forth. In some implementations, the characteristic data 128 may include information such as a timestamp associated with the EMS 106. The characteristic data 128 is indicative of a particular SFD 104 and one or more segments of the SFD 104. The device output data 126 may include information about the SFD 104 itself and the segments thereon that received the signals that are represented by the characteristic data 128. For example, the device output data 126 may be a plurality of samples, with each sample being representative of a value of characteristic data 128 for the EMS 106 received at each segment at a particular time. Each segment, in turn is associated with a particular location on the floor 102.

An object may provide a signal path that allows for cross-coupling of signals between different parts of the object, such as between the feet of a user. During operation, a first foot of the user 112 is proximate to a first SFD 104(1). The particular EMS 106(1) transmitted by the first SFD 104(1) from a first segment is electromagnetically coupled to the body of the user 112 and transferred along a signal path that includes the body of the user 112 from the first foot to the second foot of the user 112. Meanwhile, a first receiver in the first SFD 104(1) is listening for EMS 106. As the second foot approaches a second SFD 104(2), a bidirectional exchange of EMS 106 may take place. The first SFD 104(1) transmits a first set of EMS 106(1) (with segment signals sent during respective timeslots), which is received by a receiver of the second SFD 104(2). Meanwhile, the second SFD 104(2) transmits a second set of EMS 106(2) (with one or more segment signals sent during respective timeslots), which is received by a receiver of the first SFD 104(1).

As used in this disclosure, "foot" may include but is not limited to footwear or other foot coverings in addition to the anatomical feature of the user 112. For example, if the user 112 is wearing shoes, the SFD 104 may detect the presence of the sole of the shoes, and not necessarily the tissue of the user's 112 anatomy within the shoe.

The device output data 126 may be generated that is indicative of the identity of the segment of the receiving SFD 104 and the characteristic data 128 indicative of the EMS 106 that were received. The device output data 126 may be transferred from the SFD 104 in the floor 102 to an inventory management system 130 via the network 120. Other information, such as data from other sensors, may also be provided to the inventory management system 130.

The inventory management system 130 may include a data acquisition module 132. The data acquisition module 132 may be configured to control operation of the SFDs 104, receive the device output data 126, perform pre-processing on the device output data 126, and so forth. For example, as described in FIG. 2, the data acquisition module 132 may generate data captures of data from the device output data 126.

The inventory management system 130 may include a tracking module 134. The tracking module 134 may use the device output data 126 to generate user track data 136. The user track data 136 may include one or more of information indicative of the user path 114 within the facility, current location, location at a particular time, and so forth. In some implementations, the tracking module 134 may be executed as a tracking system, such as provided by one or more computing devices. The generation of the user track data 136 is discussed in more detail with regards to the following figures.

In some implementations, the tracking module 134 may use the characteristic data 128 to further distinguish between users 112 or other objects. For example, the user 112, tote 116, or other object may include a transmitter that emits a discrete EMS 106 or a receiver that receives the EMS 106 and provides characteristic data 128.

The inventory management system 130 may include an analysis module 138 to generate interaction data 140. The interaction data 140 is indicative of an action such as picking or placing an item at a particular fixture, presence of the user 112 at the fixture, and so forth. For example, the analysis module 138 may use user track data 136 to determine that a particular user 112 was in front of a particular fixture at a time when that fixture experienced a change in quantity of items stowed therein. Based on this correspondence, a particular user 112 may be associated with that change in quantity, and interaction data 140 indicative of this may be generated.

The interaction data 140 may be further processed. For example, based on the interaction data 140 indicating a pick of a particular type of item, the user account associated with the user indicated in the interaction data 140 may be billed for that item.

While FIG. 1 depicts the floor 102 as being completely covered with SFDs 104, in some implementations, only a portion of the floor 102 may include SFDs 104. For example, SFDs 104 may be placed within an aisle and not underneath the fixtures. In another example, the SFDs 104 may be deployed in front of the fixtures. The SFDs 104 may also be utilized on other surfaces of the facility. For example, SFDs 104 may be installed at the walls, fixtures, totes 116, and so forth.

The inventory management system 130 may access data from other sensors within the facility. For example, image data may be obtained from a plurality of cameras located within the facility. In another example, weight sensors on the fixtures may be used to produce weight data that is then processed to determine quantity of inventory on hand, quantity picked, quantity placed, and so forth.

Figure 2:
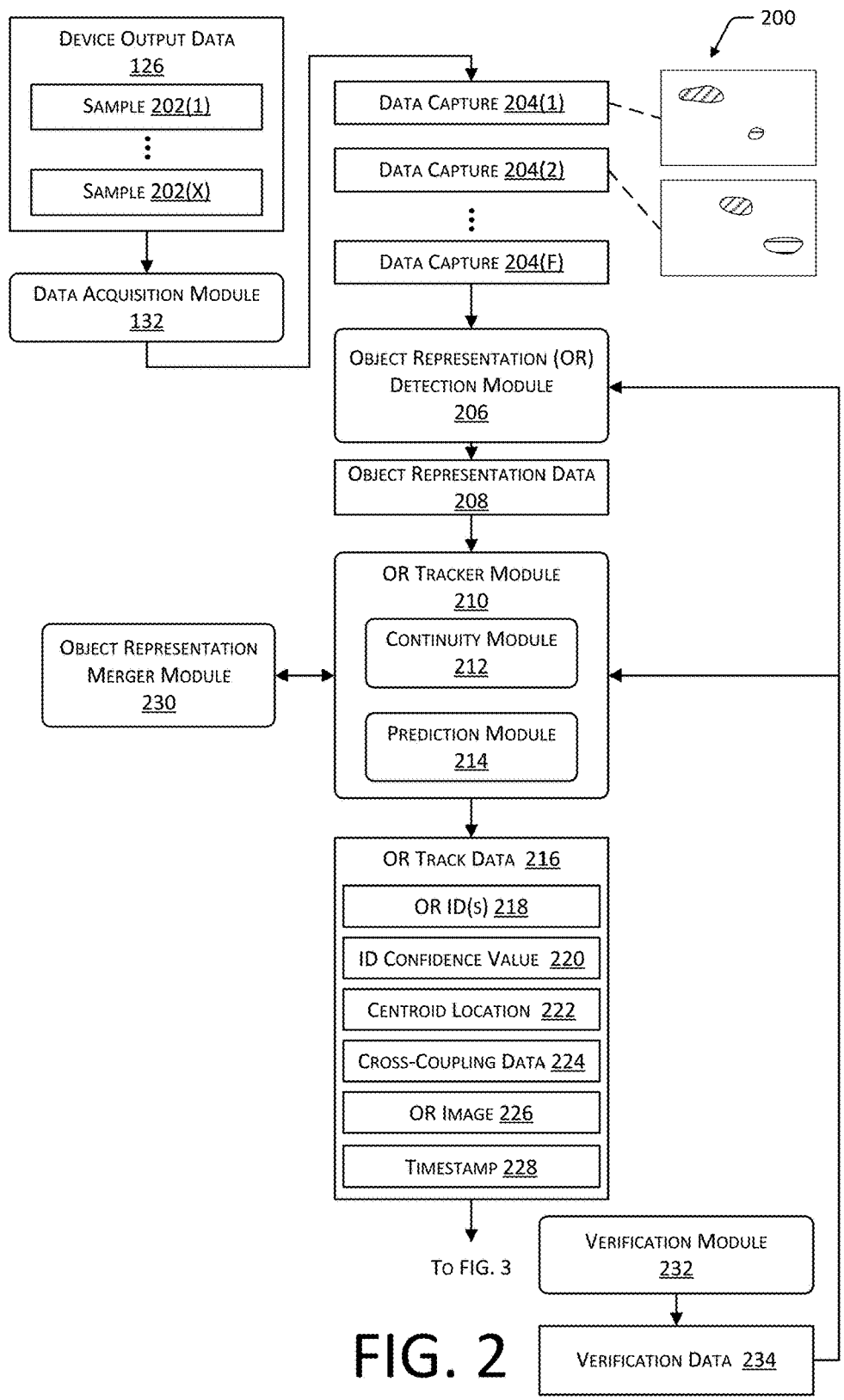
FIGS. 2-3 illustrate a block diagram of a tracking module used to track users in the facility by processing data from a smart floor, according to some implementations.
Figure 3:
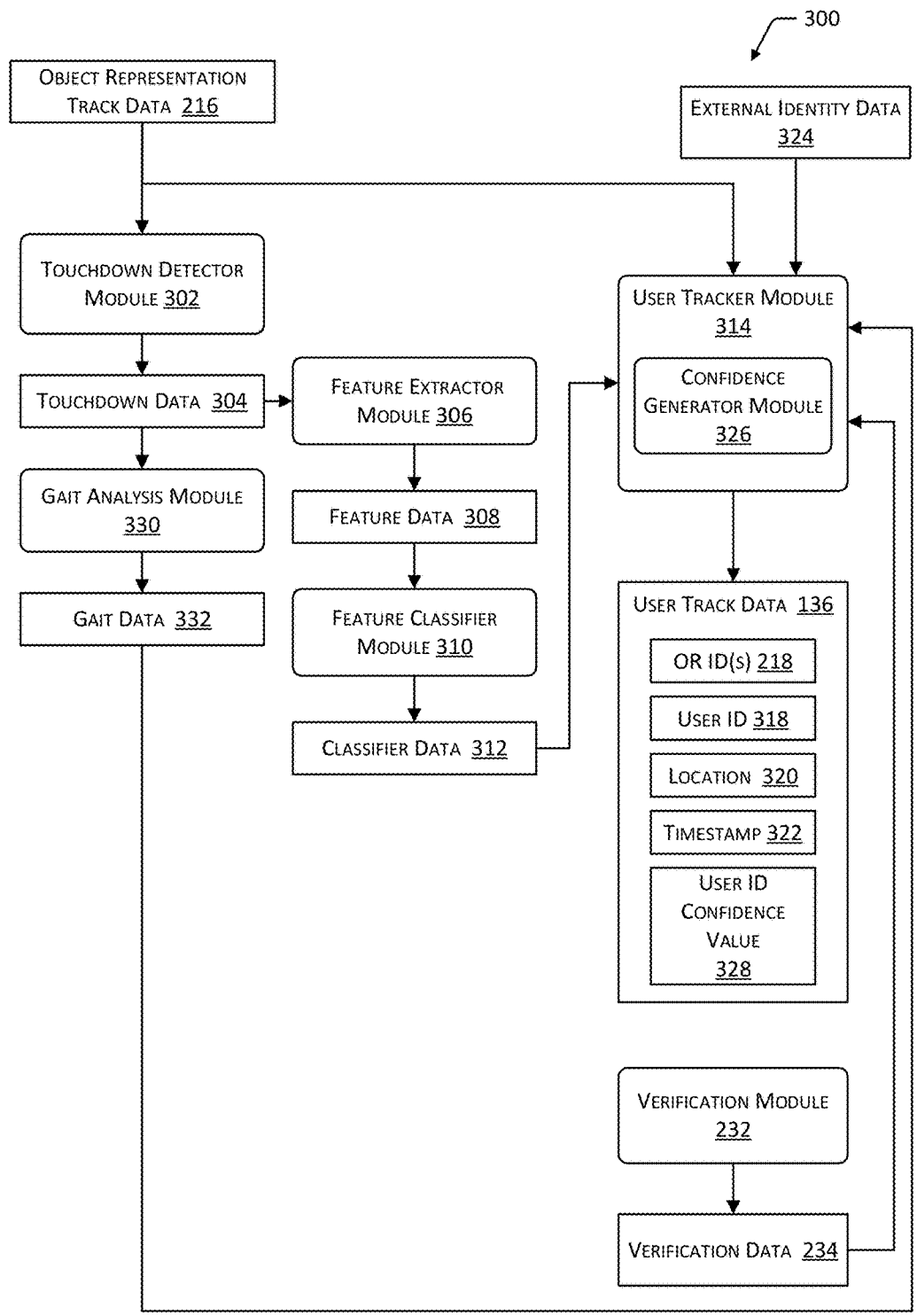

FIGS. 2-3 illustrate a block diagram of the tracking module 134 used to track users in the facility by processing data from a smart floor, according to some implementations.

FIG. 2 depicts portions 200 of the tracking module 134. The device output data 126 may comprise samples 202(1), 202(2), . . . 202(X) that are obtained from particular segments of the SFDs 104. As described in more detail below with regard to FIG. 4, each SFD 104 may comprise a plurality of segments, each segment comprising an antenna that is used to transmit or receive an EMS 106. The sample 202 may comprise information indicative of the particular segment and SFD 104 that originated the sample 202, one or more values of the characteristic data 128 from that segment, and data indicative of when the data was acquired, such as a timestamp. For example, the sample 202 may comprise information indicating the location of the segment, a value indicative of an intensity of a received signal, data indicating the segment that transmitted the received signal, and timing data indicative of when the sample 202 was acquired.

Continuing the example, the sample 202 may comprise information such as "receiving_segment:68; recieved_signal_strength:7; origin_segment: 205; timestamp:1000501".

The data acquisition module 132 may obtain the device output data 126 provided by the SFDs 104 of the floor 102 and generate one or more data captures 204 as output. Each data capture 204 may comprise data representing a two-dimensional arrangement of locations, with each location corresponding to a segment on the floor 102. For example, the floor 102 may comprise SFDs 104 with a total of 640,000 segments. Continuing the example, each of these segments may be square in shape, and the segments themselves may be arranged in a square tile pattern that is 800 segments on a side. If each segment is 3 inches on a side, the floor 102 is a square that is 200 feet on each side, and has a total surface area of 40,000 square feet. In this example, the data capture 204 could be represented as a grid that has 800 rows, 800 columns, and a total of 640,000 elements within it, each element indicative of a particular segment that corresponds to a location on the floor 102. Each element in turn may include data representative of values for one or more of the characteristic data 128 associated with the location of that element.

In some implementations the data capture 204 may comprise the entire floor 102 or may comprise a portion of the floor 102 of the facility. For example, a facility which uses a relatively large number of segments may be subdivided into sections, and data captures 204 acquired for each section. In such an implementation, the data captures 204 may overlap to allow for continuity of tracking between one section and another. In another implementation, the data captures 204 from particular sections may be joined or stitched together to produce a super data capture that encompasses the entire floor 102.

By way of illustration, and not necessarily as a limitation, the data capture 204 may be visualized as if it were a bitmap image. Each pixel in the image corresponds to a particular segment on the floor 102 that is used to obtain data. The value of each pixel in the bitmap image may be based on the value of the characteristic data 128 of that segment. For example, the color of the pixel may be represented by the received signal strength. For example, low signal strengths may be represented by blue color values and high signal strengths may be represented as red color values, producing a "heat map" type of representation. This "heat map" is not representative of physical temperature, but rather reflects other values such as intensity of received signal strength, cross-coupling data, or other values representative of the characteristic data 128.

During operation, the data acquisition module 132 may provide many data captures 204(1), 204(2), . . . , 204(F). Each data capture 204 may be representative of the samples 202 obtained at a particular time or within a particular time window. For example, data capture 204(1) may comprise samples 202 acquired from time=0 to time=30 milliseconds, while data capture 204(2) comprises samples 202 acquired from time=31 milliseconds to time=60 milliseconds, and so forth.

In some implementations the data acquisition module 132 may perform other functions. For example, the data acquisition module 132 may apply one or more filters to the samples 202, and use resulting filtered data to generate the data captures 204.

An object representation (OR) detection module 206 processes a data capture 204 to determine OR data 208 that is indicative of one or more ORs present in the data capture 204. An OR, or "blob", may comprise a region within the data capture 204 of samples 202 that are adjacent to one another and exhibit values different from those surrounding the OR. For example, the OR detection module 206 may process the data capture 204 to determine which samples 202 have a received signal strength value or intensity that is above a minimum threshold value. Those samples 202 that exhibit the received signal strength value that is greater than the threshold, or adjacent to one another and are surrounded by samples 202 with values that are less than the threshold, may be designated as an object representation.

Various OR detection algorithms may be utilized to generate OR data 208. For example, the data capture 204 may be processed using the SimpleBlobDetector Class of OpenCV as developed by Intel Corporation of Santa Clara, Calif., USA; Willow Garage of Menlo Park, Calif., USA; and Itseez of Nizhny Novgorod, Russia, with information available at www.opencv.org.

An OR tracker module 210 may use as input the OR data 208 and one or more of the data captures 204. The OR tracker module 210 may use one or more of a continuity module 212 or a prediction module 214 to generate OR track data 216.

The OR track data 216 may comprise one or more OR identifiers (OR ID) 218, ID confidence values 220, centroid location 222, cross-coupling data 224, OR image 226, timestamp 228, and so forth. An OR that has been determined by the OR detection module 206 may be assigned an OR ID 218. That OR is representative of a particular object, such as a foot of the user 112. As the object moves over time across the floor 102, the OR itself may move within the data capture 204. The OR ID 218 associates individual ORs in individual data captures 204 as being representative of the same object.

In some situations, an OR may have multiple OR IDs 218. For example, a first OR associated with a first OR ID 218(1) and a second OR associated with a second OR ID 218(2) may merge to form a third OR. The third OR may be associated with both the first OR ID 218(1) and the second OR ID 218(2).

The ID confidence value 220 provides data indicative of how likely the OR ID 218 for a particular OR is to be correct. For example, the ID confidence value 220 may be expressed as a value between 0 and 1. Returning to the example above with the third OR resulting from a merger, the third OR may have a first ID confidence value 220(1) of 0.5 for the first OR ID 218(1) and a second ID confidence value 220(2) of 0.5 for the second OR ID 218(2).

The centroid location 222 may comprise the location of the geometric centroid of the OR. The centroid location 222 may be expressed as a location with respect to the data capture 204, such as a pair of (x,y) coordinates with respect to the data capture 204, or as a physical location with respect to the floor 102.

The cross-coupling data 224 provides information indicative of cross-coupling. For example, the cross-coupling data 224 may indicate that the OR is receiving signals transmitted by one or more segments at one or more locations on the floor 102. Cross-coupling is discussed in more detail below with regard to FIGS. 6 and 7.

The OR image 226 may comprise an image representation of the OR. For example, the OR image 226 may comprise the portion of the data capture 204 that includes the OR which has been extracted and represented as an image. This portion of the data capture 204 may be extracted and stored as a separate set of data, such as an image. For example, the OR image 226 may be a cropped or extracted portion of the data capture 204 that includes the OR. In some implementations, the OR image 226 may comprise the data capture 204 with information indicative of a region within that data capture 204, such as a set of coordinates that describe a rectangle within which the OR appears. The sensor data in the data capture 204 is obtained at a particular time.

The timestamp 228 provides information indicative of the time at which the OR track data 216 is associated. For example, the timestamp 228 may comprise a value obtained from a clock that is representative of a specified time window during which the samples 202 were obtained. The timestamp 228 may comprise a value indicative of clock time, may comprise a sequence number indicative of relative timing, and so forth.

OR track data 216 for a plurality of different timestamps 228 may be expressed as a time series, in which the location and image of the OR changes over time.

The OR track data 216 may include other information as well. For example, the OR track data 216 may comprise information such as the coordinates of, or other data representative of, a perimeter of the OR.

The OR tracker module 210 may use various techniques to determine if an OR appearing in a first data capture 204(1) that comprises samples 202 obtained at a first time is the same OR that appears in a second data capture 204(2) that comprises samples 202 obtained at a second time. For example, the same OR may mean ORs in different data captures 204 that are produced by the same object, such as a foot.

One technique to determine if an OR appearing in different data captures 204 is an OR that is associated with the same object is to look for continuity between successive data captures. In one implementation, the continuity module 212 may analyze successive data captures 204 to determine if at least a portion of a first OR in a first data capture 204(1) overlaps with at least a portion of a second OR in a second data capture 204(2). For example, an overlap occurs when a first perimeter of the first OR intersects with a second perimeter of the second OR. In another example, if a location within the first OR is the same as a location within the second OR, the two are deemed to overlap. This continuity between ORs may be used to assert that the same OR is present across two or more data captures 204.

In some situations, the continuity of ORs may be lost. For example, a user 112 may lift their foot to a height at which the SFD 104 is unable to detect it. As a result, the foot may not produce an OR in a data capture 204. In another example, the user 112 may run or move so quickly that the motion of the OR produced by their foot produces such a displacement that no overlap in successive data captures 204 takes place.

The OR tracker module 210 may include a prediction module 214 that uses data captures 204 from an earlier time to determine a predicted location of the OR at a later time. The predicted location may then be used as a point from which a region of location uncertainty (ROLU) extends. For example, the predicted location may specify the coordinates at which the centroid of the OR is expected to be at a later time. The ROLU may extend away from this predicted location, describing an area in which the OR may be expected to be. The size and shape of the ROLU may be based on one or more factors including a maximum expected displacement of a foot during a time interval between successive data captures 204, a direction of travel indicated by prior centroid locations, speed of the OR, statistical estimation error, sample rate of the SFDs 104, and so forth.

ORs within the data capture 204 associated with the later time may then be assessed with respect to the predicted location and the associated ROLU. Continuing the example above, if the centroid of an OR in this later data capture 204 is within the ROLU, then that OR will be deemed to be the same as the OR that was used to determine the predicted location and the associated ROLU. In other implementations other comparisons may be made. For example, if the OR in the later data capture 204 overlaps the ROLU, then the OR may be deemed the same. Once the determination has been made, the OR ID is then asserted with that particular OR.

The prediction module 214 may implement various techniques to determine the predicted location. For example, a linear quadratic estimation (LQE) algorithm, also known as Kalman filtering, may be used to process the OR track data 216 and determine information such as speed, displacement vector, predicted location, and so forth.

In some implementations the OR tracker module 210 may use both the continuity module 212 and the prediction module 214 to assert an OR ID 218 across data captures 204. In other implementations, the continuity module 212 may be used initially, and if continuity is lost, the prediction module 214 may be used.

In some implementations, the OR tracker module 210 may use other techniques to track an OR across multiple data captures 204. For example, an optical flow module (not shown) may utilize an optical flow algorithm to determine if ORs in successive data captures are representative of the same object. In one implementation, the Lucas-Kanade algorithm for optical flow estimation may be used to determine a predicted direction vector for the OR. This predicted direction vector may be used to determine a predicted location that is then compared with an actual location of an OR in a data capture acquired at a later time. If the comparison indicates that the actual location is within a region of location uncertainty (ROLU) or other threshold value of the predicted location, the same OR ID 218 from the prior data captures may be associated with the unidentified OR.

In some situations, two or more ORs may come into contact with one another or overlap one another. As a result, the OR detection module 206 may merge the two or more ORs into a single OR. The OR tracker module 210 may be configured to retain the OR IDs 218 of the ORs that were merged. For example, the merged OR may be associated with multiple OR IDs 218, as described above. However, it may be advantageous to further process the data capture 204 to produce separate ORs.

An OR merger module 230 may be used to produce a plurality of ORs from a single OR. One technique may involve increasing the minimum threshold value used by the OR detection module 206. By increasing the minimum threshold value, areas of local maxima of a sample 202 value may be separated, producing a plurality of ORs.

Another technique may involve using algorithms such as a dilating kernel algorithm or an erosion algorithm. In one implementation, a dilating kernel algorithm may be applied to the data capture 204 to produce a dilated data capture. The dilating kernel algorithm may have the effect of suppressing or eliminating areas with lower sample values, revealing two or more distinct ORs, each having at least one local maxima. The dilating kernel algorithm may convolute a value of each sample 202 in the data capture 204 with a specified kernel. This may have the effect of computing a maximal value for the sample 202 that is overlapped by the kernel and then replacing the sample 202 value at an anchor position with this maximal value. For example, the cvDilate function of OpenCV may be used to produce a dilated data capture. Dilation is discussed below with regard to FIG. 9. By using these or other techniques, the tracking of the separate ORs and their respective OR IDs 218 may be maintained.

The tracking module 134 may include other modules, such as a verification module 232. The verification module 232 may be used to verify accuracy of information such as an OR ID 218. For example, in a situation where the ID confidence value 220 of an OR is less than a threshold value, a video comprising the data captures 204 associated with a change in the ID confidence value 220 may be presented to a human operator or automated system for further processing. The human operator may review the data and make a determination as to the OR ID 218 in that situation. The verification module 232 may produce as output verification data 234. The verification data 234 may comprise information such as corrections to OR track data 216 or other information.

In some implementations the verification data 234 may comprise statistical information about the operation of various algorithms used by the tracking module 134. This statistical information may be used to assist in the allocation of resources used to further refine those algorithms.

FIG. 3 continues depicting portions 300 of the tracking module 134. The OR track data 216 described above may be used by various modules.

Information about when the foot of a user is "touched down" may be used by the tracking module 134. For example, a foot may be considered "touched down" when it is moving at less than a maximum speed with respect to the floor 102 and exhibits a maximum typical surface area in contact with the floor. Continuing the example, a user 112 that is standing in one place will have both feet "touched down". While walking, that user 112 will have at least one foot briefly "touched down" during a stride.

A touchdown detector module 302 may be used to generate touchdown data 304. The touchdown detector module 302 may utilize information such as the OR track data 216 to determine that an OR in a data capture 204 is representative of a foot that is "touched down." For example, the touchdown detector module 302 may use the speed data determined by the prediction module 214 to determine when the OR is not moving. For example, the predicted velocity of the OR may be determined using the LQE algorithm, and if that predicted velocity is below a threshold value, the data capture may be indicative of a touched down foot or other object. In another example, if the centroid location 222 of an OR does not change more than a threshold distance during a threshold amount of time, the touchdown detector module 302 may determine that the OR is indicative of a touched down foot or other object. In yet another example, the area of the OR may be calculated in successive data captures. The data capture 204 in a set of successive data captures in which the area is at a maximum value may be designated by the touchdown detector module 302 as representing a "touched down" foot. In other implementations other techniques may be used to generate the touchdown data 304. For example, the touchdown detector module 302 may utilize a classifier algorithm, artificial neural network, and so forth.

The touchdown data 304 may comprise information such as a data capture identifier (data capture ID) indicative of a particular data capture 204, a timestamp value indicative of the time associated with the data capture 204 in which the touchdown was detected, an OR ID 218 indicative of the OR, location data of the OR, OR image 226 for that OR, and so forth.

The touchdown data 304 may be provided to an OR feature extractor module 306. The OR feature extractor module 306 is configured to generate feature data 308 about an OR. For example, the OR feature extractor module 306 may generate feature data 308 about the OR that is designated by the touchdown data 304 as being "touched down."

The feature data 308 may comprise information about the OR. For example, the feature data 308 may include one or more of a cross section of the OR, an area of the cross section, a volume of the OR based on the cross section and a value of the samples 202 within the cross section, a centroid of the cross section, a location (with respect to the centroid) of one or more local maxima of the values of the samples 202 within the cross section, a major axis of the cross section, a minor axis of the cross section, a heading of the OR based on the major axis and the minor axis, and so forth. In other implementations, the feature data 308 may include information such as a posture of the user 112. For example, the feature data 308 may indicate that the user is leaning left, leaning right, leaning forward, and so forth.

This feature data 308 may be used in several ways. When the OR track data 216 has an OR ID 218 with an ID confidence value 220 above a threshold confidence value, the feature data 308 may be used to train a feature classifier module 310. In one implementation, the feature classifier module 310 may implement a Gaussian Naive Bayes algorithm that is capable of being trained with relatively small numbers of feature data 308. In some implementations, one or more of the values of the feature data 308 may be filtered to remove outliers. The filtered data may then be grouped into subsets and then statistical values from that grouped data may be calculated. For example, group averages of those values may be determined. Continuing the example, the feature classifier module 310 may be trained using the average location of the centroid as determined from a plurality of different data captures 204 deemed to be representative of a touched down foot or other object.

In some implementations, the OR feature extractor module 306 may operate without using touchdown data 304 to generate feature data 308 representative of a foot that is in a "touched down" state. For example, feature data 308 may be determined for a plurality of data captures 204. The resulting values of the feature data 308 for these data captures 204 may be filtered to find values greater than a threshold, such as a ninetieth ($90^{th}$) percentile value. Outliers of these values may be removed, and the subsequent values may then be used to generate feature data 308 indicative of a foot that is "touched down."

The OR feature extractor module 306 determines the location of various features in the OR with respect to reference points that are specific to the OR. For example, a geometric centroid of the OR may be determined, and the major axis and minor axis that pass through the centroid may be determined. The location of features, such as a local minima or local maxima, may be determined with respect to the centroid and the major axis and minor axis.

In some implementations the OR feature extractor module 306 may resample the input prior to feature extraction. For example, the data captures 204 or portions thereof such as an OR image 226 may be resampled. The resampling may comprise increasing the number of samples in the resulting resampled data capture compared to the original data capture 204. For example, the input may be resampled at a ratio of 10:1 using a 2-D spline interpolation algorithm. Other resampling ratios may be used. The OR feature extractor module 306 may then process the resampled data to determine the feature data 308.

In some implementations the SFDs 104 may produce device output data 126 that is indicative of a height of an object above the floor 102. The OR feature extractor module 306 may be configured to generate feature data 308 for samples 202 that correspond to a particular height. For example, the OR feature extractor module 306 may determine the feature data 308 based on samples 202 corresponding to at least a minimum height above the floor 102.

Once the feature classifier module 310 has been trained, it may be utilized to determine the OR ID 218 for an unidentified OR. For example, the feature data 308 for an unidentified OR may be processed by the trained feature classifier module 310, and classifier data 312 may be produced that is indicative of an OR ID 218 and an ID confidence value 220 for that OR ID 218. In some implementations, the feature classifier module 310 may be configured to produce classifier data 312 that indicates a particular user ID 318, as described below, that is associated with the unidentified OR.

The tracking module 134 may include a user tracker module 314. The user tracker module 314 is configured to use input such as the OR track data 216 to generate the user track data 136. The user track data 136 may include one or more OR IDs 218, a user identifier (user ID) 318 that is associated with the one or more OR IDs 218, a location 320 of the user 112, a timestamp 322 indicative of the time associated with the user track data 136, and so forth. As described above, the user 112 may be associated with a plurality of OR IDs 218. In some implementations, the same OR ID 218 may be associated with more than one user ID 318, such as described above in the event of an OR merger.

The user ID 318 is indicative of a particular user 112 that is in the facility. In some implementations the user ID 318 may be assigned and used for that particular user 112 while they are in the facility, and then is removed or reassigned to another user 112 later. In other implementations the user ID may be associated with an actual identity of the user 112. For example, the user ID "39481" may be indicative of "Bob M. Jones", and is used in the user track data 136 when Mr. Jones is in the facility.

In some implementations the user ID 318 may be asserted using external identity data 324. For example, an identity of the user 112 may be asserted at the entry 110. Continuing the example, the user 112 may provide identification credentials such as swiping an identification card, by carrying a device that transmits or displays authentication credentials, by providing a fingerprint, and so forth. Once this external identity data 324 is asserted, it may be used to assign the user ID 318 for the OR ID 218 associated with entry.

The user tracker module 314 may include a confidence generator module 326 to generate a user ID confidence value 328. The user ID confidence value 328 provides information indicative of a probability that the user ID 318 is associated with the correct OR ID 218. For example, the confidence generator module 326 compares various inputs to the user tracker module 314 and determines if there are incongruities between them. Based on this comparison, a user ID confidence value 328 may be generated. In another example, the various inputs may be used to further reinforce the user track data 136. For example, a previously asserted user ID 318 may be considered highly confident if the gait data 332 and the classifier data 312 assert the same user ID 318 with a high confidence value.

Other information may be determined from the OR track data 216. A gait analysis module 330 may process the OR track data 216 to generate gait data 332. In some implementations, the gait analysis module 330 may utilize the touchdown data 304 to generate the gait data 332 from those data captures 204 that are associated with a touchdown of the user's 112 foot. The gait data 332 may include information associated with the movement of a particular user 112, as represented in the data captures 204. For example, the gait data 332 may be indicative of one or more of timing between steps, stride length, touchdown dwell time, acceleration profile, velocity overall, velocity of a particular OR, and so forth.

The user tracker module 314 may be used to determine an association between an OR ID 218 and a user ID 318 for ORs that are not currently associated with at least one user ID 318. For example, as a new user 112 enters the facility, the ORs associated with their presence would be assigned OR IDs 218. These ORs would then be processed by the user tracker module 314 to associate those ORs with the user ID 318 for that new user 112. The user tracker module 314 may be used when an OR splits or a new OR is otherwise created. For example, if the user 112 enters the facility carrying a child, and later sets the child down, the child will result in the formation of two new ORs.

The gait analysis module 330 may operate in conjunction with the user tracker module 314 to acquire historical gait data that includes gait data 332 and an association with a particular OR ID 218 or user ID 318.

The user tracker module 314 may perform a comparison between the gait data 332 of one or more unidentified ORs and the historical gait data. If the comparison indicates a match that is within a threshold value, the OR ID 218 or user ID 318 associated with that historical gait data may be associated with the one or more unidentified ORs.

The gait data 332 may be used by other modules as well. For example, the prediction module 214 may use the gait data 332 to generate predictions as to the movement of an OR.

As described above, the verification module 232 may provide verification data 234 to the user tracker module 314. For example, if the user ID confidence value 328 is below a threshold value, data may be presented to a human operator or automated system for further processing. The human operator may review the data and make a determination as to the user ID 318 in that situation. The verification module 232 may produce as output verification data 234. The verification data 234 may comprise information such as corrections to user track data 136 or other information.

Figure 4:
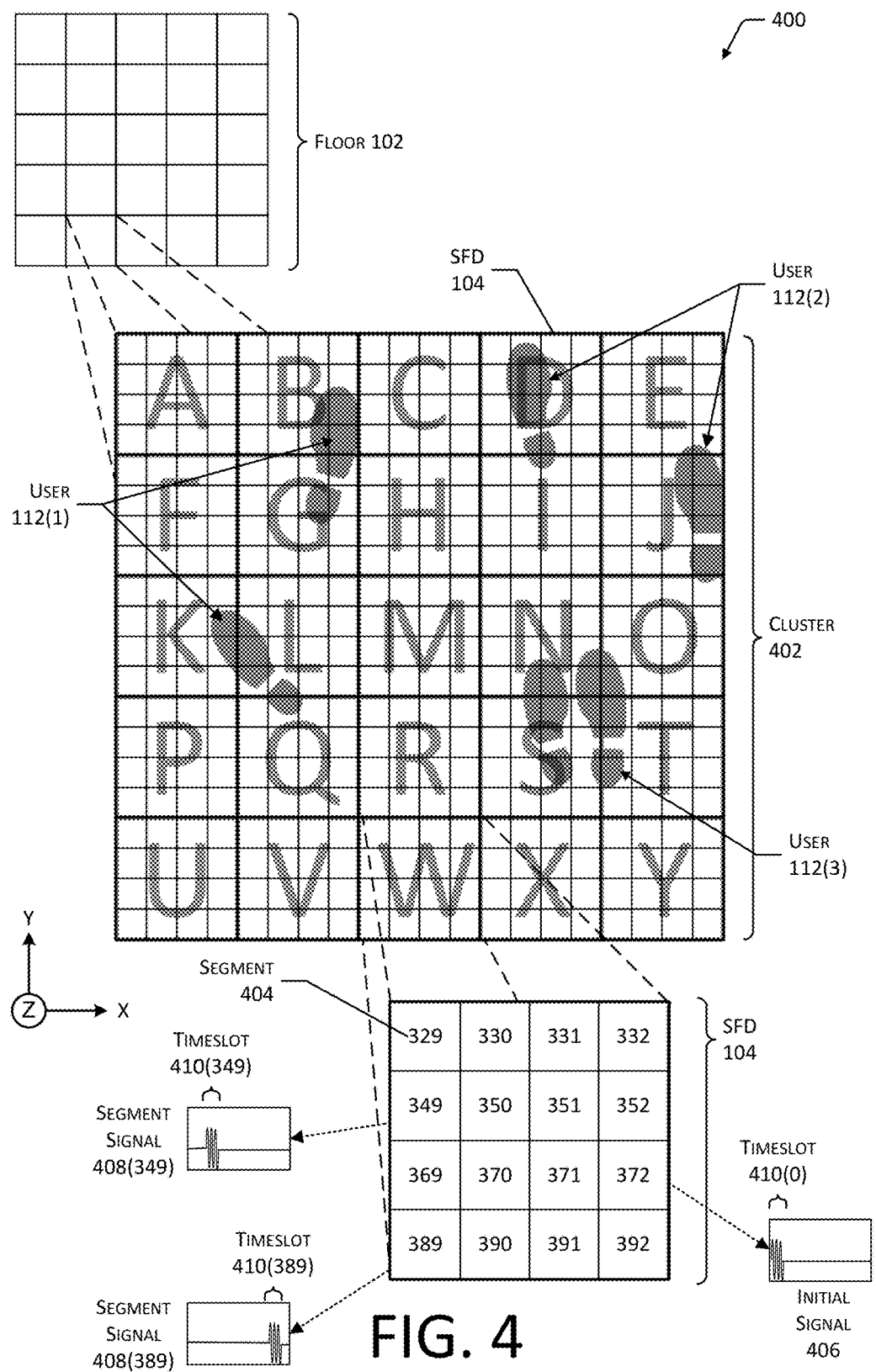
FIG. 4 illustrates an arrangement of smart floor devices and the respective segments within a cluster, according to some implementations.

FIG. 4 illustrates an arrangement 400 of SFDs 104 and their respective segments including clusters, according to some implementations.

A portion of the floor 102 is depicted which is made up of several clusters 402. A cluster 402 is a grouping of segments 404 of the SFDs 104. For example, the cluster 402 depicted here comprises twenty-five (25) SFDs 104(A), 104(3), . . . , 104(Y). In other implementations, a cluster 402 may include different numbers of SFDs 104. Each SFD 104 in turn may include one or more segments 404. Continuing the example depicted here, each SFD 104 includes sixteen (16) segments 404. In other implementations, the SFD 104 may include different numbers of segments 404.

In some implementations, individual segments 404 may be part of a SFD 104, or may be discrete devices that are joined together to form a SFD 104 or cluster 402. For example, the segments 404 may be connected to one another, a backplane, wiring harness, and so forth, to form a SFD 104.

The physical size of a cluster 402 may be determined in some implementations based on a maximum expected stride length for a user 112. For example, a user 112 may be expected to have a stride length that is less than 4 feet while walking. If the SFDs 104 are 1 foot on each side, then the cluster 402 depicted here is 5 feet by 5 feet. Likewise, each segment 404 is 3 inches by 3 inches. In other implementations, other sizes of segments 404, SFDs 104, and clusters 402 may be used. Also, other shapes of segments 404, SFDs 104, and clusters 402 may be used. For example, the segments 404 may be triangular shaped, SFDs 104 may be rectangular, and so forth.

The SFD 104 transmits one or more EMS 106. For example, an initial signal 406 and one or more segment signals 408 may be transmitted. Together, these signals comprise the EMS 106 emitted by the SFD 104. The segment signal 408 may be unmodulated, or may contain null data. The EMS 106 transmitted by the SFD 104 may be at a first frequency. The segment signal 408 may be transmitted at the first frequency and includes a signal that is transmitted at a particular time within a timeslot 410. The timeslot 410, in turn, is associated with the particular segment 404 within the cluster 402. For example, a segment signal 408 received during a particular timeslot 410 may be deemed associated with the segment 404 assigned to that timeslot. In some implementations, the occurrence of the segment signal 408 at a particular time within a timeslot 410 is thus representative of the particular timeslot 410, and the corresponding segment 404 associated with that timeslot 410. In some implementations, the timeslot 410 may be 3 millisecond (ms) or less in duration. For example, the timeslots 410 may be 40 microseconds. The characteristic data 128 may include timestamp data associated with receipt of one or more of the initial signal 406 or the segment signal 408. In some implementations, the timestamp data may be used to determine the timeslot 410.

The segment signals 408 may be configured such that the first timeslot 410(1) is associated with a segment 404(1), a second timeslot 410(2) is associated with a segment 404(2), and so forth. In one implementation, each timeslot 410 may be less than or equal to 40 microseconds in duration. In some implementations, the duration of timeslots 410 may differ. For example, timeslot 410(1) may be 40 microseconds in duration while timeslot 410(2) is 50 microseconds in duration. Timing of the timeslots 410 may be synchronized to the clock signal 124. For example, the clock signal 124 may be used to synchronize the clocks in respective SFDs 104 which in turn activate their respective segments 404 during the timeslots 410 assigned to those segments.

The EMS 106 as emitted may exhibit sinusoidal waveforms. In other implementations, other waveforms such as square, triangle, sawtooth, and so forth, may be used. Use of sinusoidal waveforms may allow for reduced channel spacing and minimize adjacent channel interference. The EMS 106 may be transmitted at carrier frequencies of between 40 kilohertz and 30 megahertz. For example, the EMS 106 used by the segments 404 in the floor may be about 4 megahertz. In other implementations, other frequencies may be used. In some implementations, the waveforms of the initial signal 406 may differ from the waveforms of the segment signal 408.

In some implementations, as depicted here, each cluster 402 may utilize the same spatial arrangement of segments 404, segment number scheme, and the corresponding timeslot 410 associated with that segment 404. For example, the clusters 402 in the floor 102 may all utilize the same arrangement of segments 404, such as beginning at the top left of the cluster 402 with segment 1 and increasing from left to right and into subsequent rows, such as in FIG. 4.

In this illustration, three users 112 are depicted. The right foot of user 112(1) is above the segments 404 in SFDs 104(B) and 104(G). The left foot of user 112(1) is above the segments 404 in SFDs 104(K), 104(L), and 104(Q). Also shown are the feet of users 112(2) and 112(3) at other locations within the cluster 402. A representation of the characteristic data 128 associated with the first user 112(1) is depicted below with regard to FIG. 8.

The SFDs 104 may be configurable, such that they may be installed and then configured to transmit at a particular frequency after physical installation of the SFD 104. For example, the SFDs 104 in the floor 102 may be electronically switched to generate EMS 106 at a specified frequency.

The SFDs 104 may be installed inside or outside of a building. For example, the floor 102 of an uncovered area, yard, exterior shed, and so forth may be equipped with the SFDs 104.

While the hierarchy of floor 102, cluster 402, SFD 104 and segments 404 is discussed and used herein, it is understood that other hierarchies or arrangements may utilize the techniques described herein. For example, instead of segments 404 being part of an SFD 104, the floor 102 may comprise a plurality of single-segment SFDs 104. The segment signals 408 may then be transmitted, in the appropriate timeslot 410, to indicate a particular timeslot 410. In another example, instead of arranging SFDs 104 into clusters 402, each SFD 104 may have a unique combination of one or more of frequency, timeslot, or other characteristics of EMS 106 that are used to identify a particular SFD 104 on the floor 102.

Instead of, or in addition to, the use of timeslots 410, other techniques may be used to provide information indicative of the segment 404 from which a signal originated. For example, each segment 404 within a cluster 402 may transmit a different frequency, identifier sequence, and so forth.

Figure 5:
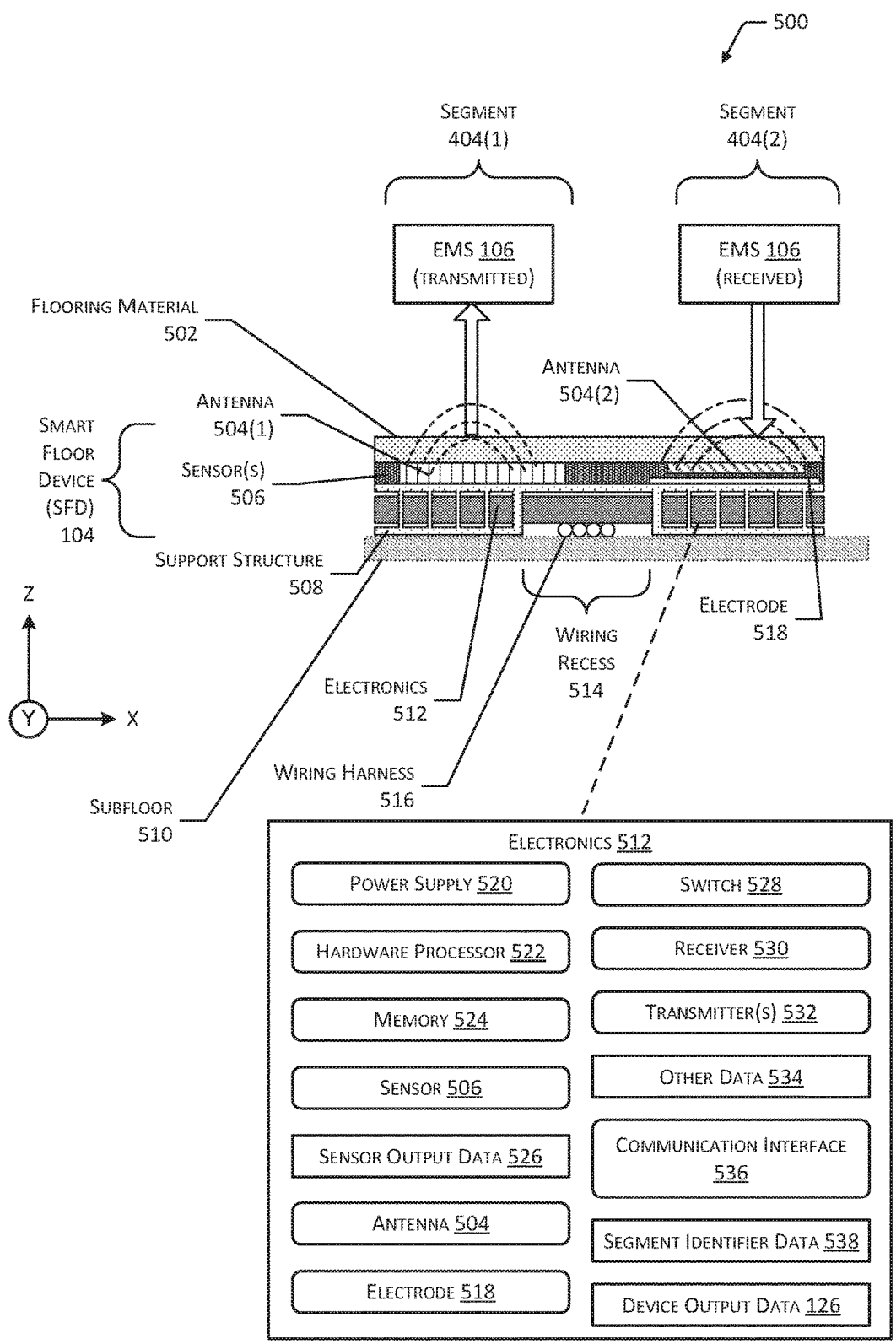
FIG. 5 illustrates the arrangement of components included in the smart floor device, according to some implementations.

FIG. 5 illustrates the arrangement 500 of components included in a SFD 104, according to some implementations. A side view of a portion of the SFD 104 depicts a top layer comprising a protective material, such as flooring material 502. The flooring material 502 is electrically non-conductive under ordinary conditions. For example, the flooring material 502 may include plastic, ceramic, wood, textile, or other material. Beneath a layer of flooring material 502 may be one or more antennas 504 and one or more sensors 506. The antennas 504 may comprise structures designed to accept or emit EMS 106. In some implementations, the antennas 504 may also serve as the flooring material 502. For example, the antennas 504 may comprise aluminum or steel sheets upon which the users 112 walk. The active portion of the antenna 504 comprises that portion of the antenna 504 that is used to radiate or receive an EMS 106.

The SFD 104 may include a plurality of antennas 504. For example, the antennas 504 may be arranged to form an array. In some implementations, the active portion of the antennas 504 may have a surface area that occupies at least 1 square inch. Each segment 404 includes at least one segment antenna 504. The segment antenna 504 of the segment 404 may be the same size as the segment 404 or may be smaller. For example, the segment 404 may be 3 inches by 3 inches square, but the segment antenna 504 in that segment 404 may only be 2 inches by 2 inches square. In another example, the segment 404 may be 3 inches by 3 inches square and the segment antenna 504 in that segment 404 may be 3 inches by 3 inches square. Each segment antenna 504 may have a maximum size of sixteen square inches, in some implementations. The size of the segment antennas 504 may be determined at least in part based on the expected size of the objects in contact with the floor 102, such as the size of the foot of the user 112. In one implementation, antennas 504 may be shared, with a single antenna 504 being used to both transmit and receive simultaneously or at different times. In another implementation, separate antennas 504 may be used to transmit and receive.

The SFD 104 may also include a plurality of sensors 506 that may be arranged to form one or more arrays. For example, the sensors 506 may include weight sensors that measure the weight applied to a particular segment 404. The sensors 506 provide sensor output data. The arrangement of an array of one type of sensor may differ from another type of sensor. In some implementations, the sensors 506 may include a magnetometer that provides information about local magnetic fields, an accelerometer that provides information about vibration, and so forth. The SFD 104 may incorporate one or more of the sensors described below with regard to FIG. 11, or other sensors.

As illustrated here, the antennas 504 may be located within a common plane. In other implementations, the antennas 504 may be arranged within a layer that is above the sensors 506, below the sensors 506, and so forth. A load bearing support structure 508 may be beneath the sensors 506 and the antennas 504 and provides mechanical and physical separation between the underlying subfloor 510 upon which the SFD 104 rests and the flooring material 502. The support structure 508 may comprise a series of pillars, posts, ribs, or other vertical elements. The support structure 508 may comprise a composite material, plastic, ceramic, metal, or other material. In some implementations, the support structure 508 may be omitted, and electronics 512 or structures associated with the electronics 512 may be used to support a load on the flooring material 502. For example, the electronics 512 may comprise a glass fiber circuit board that provides mechanical support while also providing a surface for mounting the electronics 512. The subfloor 510 may comprise concrete, plywood, or existing flooring materials over which the SFD 104 is installed. In some implementations, the SFD 104 may be affixed to the subfloor 510, or may be unaffixed or "floating". For example, the SFD 104 may be adhered to the subfloor 510 using a pressure sensitive adhesive.

The SFD 104 includes the electronics 512. The electronics 512 may include the elements described elsewhere in more detail. In the implementation depicted here, the electronics 512 are arranged within the support structure 508. In some implementations, one or more of the antennas 504 or the sensors 506 may be located within the support structure 508. The support structure 508 may operate as a heat sink to dissipate heat generated by operation of the electronics 512.

The SFD 104 may incorporate a wiring recess 514 on an underside of the SFD 104. For example, the support structure 508 and the electronics 512 may be formed or arranged to provide a pathway for a wiring harness 516 to pass beneath at least a portion of the SFD 104. The wiring recess 514 may extend from one edge of the SFD 104 to another, may extend in different directions, and so forth. For example, the wiring recess 514 may be arranged in a "+" or cross shape, allowing for wiring harnesses 516 to pass along the X or Y axes as depicted here.

The wiring harness 516 may provide a coupling to one or more of the power supply 118, the network 120, and so forth. For example, the wiring harness 516 may include conductors that allow for the SFD 104 to receive electrical power from an electrical distribution network, allow for connection to a Controller Area Network (CAN) bus network that services a group of SFDs 104, and so forth. The wiring harness 516 may include electrical conductors, electromagnetic waveguides, fiber optics, and so forth. In some implementations, a plurality of wiring harnesses 516 may be used. For example, a first wiring harness 516(1) may provide electrical power while a second wiring harness 516(2) provides network connectivity. In some implementations, the wiring harness 516 may be used to provide information that is then processed to determine a relative arrangement of SFDs 104.

With respect to the antennas 504, in some implementations an electrode may be proximate to, but separated by a dielectric from, one or more of the antennas 504. The electrode 518 may be utilized to improve received signal voltage at the antenna by increasing the effective impedance for the receive antenna. The electrode 518 may increase the effective impedance by reducing the receive circuit parasitic capacitance to ground. The electrode 518 may be driven with a signal from a receive buffer output which has a unity gain, wide bandwidth, low output impedance, and a negligible phase shift in the working bandwidth. In this configuration, the receive antenna 504 to ground parasitic capacitance may be almost eliminated. For the receive antenna 504, by utilizing the electrode 518 the corresponding receive signal level, such as measured Volts peak-to-peak (VPP), may be improved by more than 50 times as compared to implementations without the electrode 518. This improved sensitivity improves overall system performance.

The electronics 512 of the SFD 104 may include a power supply 520. The power supply 520 may include an electric power interface that allows for coupling to the power supply 118. For example, the electrical power interface may comprise connectors, voltage converters, frequency converters, and so forth. The power supply 520 may include circuitry that is configured to provide monitoring or other information with regard to the consumption of electrical power by the other electrical power components of the SFD 104. For example, the power supply 520 may include power conditioning circuitry, DC to DC converters, current limiting devices, current measurement devices, voltage measurement devices, and so forth. In some implementations, the SFD 104 may be configured to connect to redundant power buses. For example, a first electrical distribution network such as an "A" bus and a second electrical distribution network such as a "B" bus may be provided, each of which can provide sufficient electrical power for operation. In some implementations, the SFD 104 may incorporate redundant power supplies 520.

The SFD 104 may include one or more hardware processors 522. Hardware processors 522 may include microprocessors, microcontrollers, systems on a chip (SoC), field programmable gate arrays (FPGAs), and so forth. The SFD 104 may also include one or more memories 524. The memory 524 may comprise one or more non-transitory computer-readable storage media (CRSM). The CRSM may be any one or more of an electronic storage medium, a magnetic storage medium, an optical storage medium, a quantum storage medium, a mechanical computer storage medium, and so forth. The memory 524 provides storage of computer-readable instructions, data structures, program modules, and other data for the operation of the SFD 104.

The electronics 512 may be configured to acquire information from sensors 506 of the SFD 104. In one implementation, the sensors 506 may comprise electrodes or other electrically conductive elements that are used as part of a capacitive sensor array. In one implementation, the electrodes may be arranged in an array. Each electrode may be rectangular with a first side and a second side, with the length of the first side and the second side being between 10 millimeters and 50 millimeters. In other implementations, other shapes and sizes of electrodes may be used.

The electronics 512 may include capacitance measurement circuitry that generates capacitance data. The capacitance measurement circuitry may use various techniques to determine capacitance. For example, the capacitance measurement circuitry may include a source that provides a predetermined voltage, a timer, and circuitry to measure voltage of the conductive element relative to the ground. By determining an amount of time that it takes to charge the conductive element to a particular voltage, the capacitance may be calculated. The capacitance measurement circuitry may use one or more of analog or digital circuits to determine capacitance. During operation, the capacitive sensor uses a conductive element located beneath the flooring material 502 to produce capacitance data indicating capacitance values at particular times. Based on the capacitance data, information such as a presence of an object, shape of an object, and so forth, may be generated to produce sensor output data 526. The sensor electronics 512 may be configured to scan the sensors 506 and generate sensor output data 526 at least 30 times per second. The sensor output data 526 may include information about proximity of an object with respect to a particular electrode. The sensor output data 526 may be further processed to generate the other data.

In other implementations, the sensors 506 may comprise optical touch sensors comprising one or more illuminators and one or more photodetector elements, resistive touch sensors comprising electrically resistive material, acoustic touch sensors comprising one or more transducers, and so forth. The sensors 506 may include other sensors, such as weight sensors, moisture detectors, microphones, and so forth.

The SFD 104 may include a receiver 530. The receiver 530 is configured to detect the EMS 106. The receiver 530 may be implemented as discrete circuitry, as a software defined radio (SDR), and so forth. The receiver 530 is coupled to one or more of the antennas 504. In some implementations, a single receiver 530 may be coupled to a single antenna 504. In other implementations, a single receiver 530 may be coupled to a plurality of antennas 504 by way of a switch 528, matching network, and so forth. The switch 528 or switching circuitry may allow the selective connection of a particular antenna 504 to the receiver 530. This selective connection may include the disconnection of one antenna 504 and connection of another antenna 504 at a particular time. The receiver 530 may be configured to detect the EMS 106 at a particular frequency and generate information indicative of a received signal strength. For example, the switch 528 may operate to connect the particular antenna 504 for the segment 404 associated with a particular timeslot 410.

In some implementations the receiver 530 may utilize one or more of amplitude modulation rectification, synchronous detection, and so forth to detect the signal. For example, the received signals may be buffered, filtered with a narrow band filter, amplified, and detected using a synchronous detector. The detection may provide information about the amplitude, phase, and so forth. In some implementations the use of a synchronous detector may provide amplitude information, attenuate noise, and provide phase delay information. The output from the detector may be digitized to produce digital data. The digital data may then be analyzed for timing, to determine amplitude, and so forth using a digital signal processor (DSP). Post-processing may be used to detect proximity of an object to the segment 404 based on amplitude variation within the segment, such as changes in self-coupling, or through propagation of signals through the body of the user 112 or other object.

In some implementations, elements of the sensors 506 may be combined or used in conjunction with the antennas 504. For example, electrically conductive elements may be used for both capacitive sensing by the sensor 506 and as antennas 504. This dual use may occur at the same time or may be multiplexed over time. For example, switching circuitry may, at a first time, selectively connect the sensor electronics 512 to the electrically conductive element for use as a capacitive sensor pad. The switching circuitry may then selectively connect, at a second time, the receiver 530 to the same electrically conductive element for use as an antenna 504.

The EMS 106 is acquired by the antenna 504 and then provided to the receiver 530. For example, the receiver 530 may comprise a superheterodyne receiver, with an incoming radio signal being converted to an intermediate frequency by a mixer. At the intermediate frequency stage, the downconverted signal is amplified and filtered before being fed to a demodulator. One or more antennas 504 may be dedicated for use by the receiver 530, while one or more other antennas 504 may be dedicated for use by the transmitter(s) 532. The use of separate antennas to transmit and receive may improve isolation between the receiver 530 and the transmitter 532. The receiver 530 or the hardware processor 522 processes the EMS 106 to determine the characteristic data 128, such as a received frequency and the signal strength received at that frequency. In another implementation, the receiver 530 may comprise a SDR.

In some implementations, the EMS 106 may encode data. The receiver 530 or the hardware processor 522 may decode, decrypt, or otherwise demodulate and process the demodulated signal to determine the characteristic data 128. For example, the receiver 530 may provide as output the digital representation of a signal that incorporates binary phase shift keying (BPSK) or other techniques. The hardware processor 522 may process this digital representation to recover a serial data stream that includes framing, error control data, payload, and other information. The payload may then be processed to produce output. The error control data may include error detection data such as parity check data, parity bits, hash values, and so forth. For example, a hash function may be applied to the characteristic data 128 to generate hash output. A comparison of the hash output may be made to determine if an error is present.

The SFD 104 includes one or more transmitters 532. For example, the transmitter 532 may comprise a voltage controlled oscillator that generates an output signal that is fed directly to a power amplifier. The transmitter 532 couples to an antenna 504, which then radiates the EMS 106. The transmitter 532 may be implemented as discrete circuitry, SDR, or a combination thereof.

The transmitter 532 may accept multiple signals to generate the EMS 106 that is emitted from an antenna 504 connected to the output of the transmitter 532. In some implementations, each segment 404 may utilize a single transmitter 532 that produces an EMS 106 that includes at least the segment signal 408. In other implementations, a single transmitter 532 may be used to generate all of the EMS 106 from a given SFD 104. For example, the transmitter 532 may generate the initial signal 406 and all the respective segment signals 408 for that SFD 104 that are directed to the appropriate antennas 504 during the particular timeslots 410 by way of a switch 528 or other circuitry.

The transmitter 532 may be configured to produce an output signal that is amplitude modulated, frequency modulated, phase modulated, and so forth. The transmitters 532 for the SFDs 104 in a given floor 102 may operate on a single frequency, or may be frequency agile and operate on a plurality of different frequencies. In some implementations, the receiver 530 and the transmitter 532 may be combined or share one or more components. For example, the receiver 530 and the transmitter 532 may share a common oscillator or frequency synthesizer.

In some implementations, a single antenna 504 may be used to both transmit and receive. For example, the receiver 530 may include notch filters to attenuate the frequencies of the transmitted EMS 106. A single antenna 504 may also be used to transmit different signals. For example, a single antenna 504 may be used to transmit the initial signal 406 and a segment signal 408. In some implementations, a diplexer may be used that accepts input from two or more transmitters 532 and provides output of the EMS 106 to an antenna 504 or group of antennas 504. In other implementations, the diplexer or other filtering may be omitted, and one or more transmitters 532 may be coupled to a single antenna 504 or group of antennas 504.

The hardware processor 522 may acquire data from one or more of the sensors 506, the receiver 530, the transmitter 532, and so forth, to generate other data 534. The other data 534 comprises information about an object that is resting on or proximate to the flooring material 502. The information may be indicative of a shape of the object. In some implementations, the other data 534 may comprise information that is representative of the contours of an object. For example, the other data 534 may comprise a bitmap representative of the output from a plurality of sensors 506 and indicative of their relative arrangement. In another example, the other data 534 may comprise a vector value that is indicative of polygons used to represent an outline of an object. In some implementations, the other data 534 may be indicative of an area of the object. For example, the other data 534 may indicate that the total area of an object is 58 square centimeters. The other data 534 may include other information such as information about amplitude of a received EMS 106 with respect to different portions of the object. For example, other data 534 may be generated that indicates the shape of the object with information about amplitude, frequency, or other details about the EMS 106 at particular points or areas within that shape.

In some implementations, one or more of the receivers 530 or the transmitters 532 may be used to generate the sensor output data 526. For example, sensors 506 may communicate with the power supply 520 to determine the amount of electrical current that is being drawn at a particular time by the transmitter 532. As the electrical coupling between an object above the SFD 104 and one or more of the antennas 504 changes, one or more operating characteristics of the devices in the SFD 104 may change. For example, the impedance of the antenna 504 may experience change. Changes in the impedance may result in a change in the power output of the transmitter 532 during operation. For example, the transmitter 532 may exhibit an impedance mismatch with the antenna 504 in the presence of an object, such as a foot. This impedance mismatch may result in reduced power consumption by the radio frequency amplifier of the transmitter 532. Information about changes in the operational characteristics, such as a change in current draw by the transmitter 532, may be processed to determine the presence or absence of an object with respect to the antenna 504. The operating characteristics may include, but are not limited to: received signal strength at the receiver 530, power consumption of the transmitter 532, radio frequency power output of the transmitter 532, impedance presented at an antenna 504, standing wave ratio (SWR), and so forth.

For example, the impedance of the antenna 504 may be measured at a radio frequency input to the receiver 530, a radio frequency output of the transmitter 532, and so forth. In another example, the SWR presented by one or more of the antennas 504 may be similarly measured. In other implementations, other operating characteristics may be used. For example, a change in the noise detected by the receiver 530 may be used to determine presence or absence of an object. In yet another implementation, the transmitter 532 of the SFD 104 may generate a signal that is then received by the receiver 530 of the same SFD 104. A change in the received signal at a particular antenna 504 may be used to determine the presence of an object. In still another implementation, the EMS 106 received from the other SFD 104 may be measured, and the received signal strength at particular segments 404 may be used to generate information indicative of the presence of an object.

By combining information from a plurality of antennas 504, other data 534 may be generated. In other implementations, other characteristics of the receiver 530 or the transmitter 532 may be assessed to generate the other data 534 or other information indicative of proximity of an object to the antenna 504. For example, the change in impedance may be measured, a change in background noise level may be measured, and so forth. In some implementations, radio ranging may be utilized in which the transmitter 532 emits a pulse and the receiver 530 listens for a return or echo of that pulse. Data indicative of proximity from several antennas 504 may then be processed to generate the other data 534. In another implementation, distance between the object and the antenna 504 may be determined using the amplitude of the received EMS 106. For example, a lookup table may be used that associates a particular received signal strength with a particular distance from the antenna 504.

The communication interface 536 connects the SFD 104 to the network 120. For example, the communication interface 536 may be able to connect to one or more of a Controller Area Network (CAN bus), Inter-Integrated Circuit (I2C), Serial Peripheral Interface bus (SPI), 1-Wire bus, Universal Serial Bus (USB) as promulgated by the USB Implementers Forum, RS-232, Ethernet, Wi-Fi, Bluetooth, and so forth. The communication may be facilitated by data connectors, such as optical connectors, electrical connectors, and so forth. The data connectors provide a pathway for signals to be exchanged between the communication interface 536 and the network 120.

The SFD 104 may include non-transitory computer readable media that is used to store instructions, data, and so forth. Segment identifier data 538 comprises information indicative of a particular segment 404. In some implementations, the segment identifier data 538 may be indicative of a particular segment 404 of a particular SFD 104. The segment identifier data 538 may be unique within the cluster 402, the particular network 120, the facility, unique across the production of all SFDs 104 manufactured, and so forth. In some implementations, a media access control (MAC) address, network address, bus address, and so forth, that is associated with the communication interface 536 may be used as segment identifier data 538.

During operation, the hardware processor 522 may generate device output data 126. As described above, the device output data 126 may include the characteristic data 128. In some implementations, the device output data 126 may indicate the characteristic data 128 that was received by the SFD 104, the particular antennas 504 or segments 404 associated with that reception, information about the frequencies of EMS 106 that are being received, phase information, and so forth. The device output data 126 may also include the segment identifier data 538, timestamp data, and so forth. For example, the timestamp data included in the device output data 126 may indicate when the characteristic data 128 was received by the receiver 530.

The SFD 104 may include multiple hardware processors 522 with different capabilities. For example, individual elements of the sensors 506 may utilize dedicated state machines to perform simple processing functions. These dedicated state machines may then send output data to a microcontroller that provides additional processing to generate sensor output data 526. In one implementation, the dedicated state machine may comprise a complex programmable logic device (CPLD). Continuing the example, a dedicated state machine may provide a 4-bit value indicative of the capacitance measured by a capacitive sensor 506 at a particular location on the SFD 104. The microcontroller may have information that describes a relative arrangement of the sensors 506, and may use this information in conjunction with the dedicated state machine output to generate a bitmap that may be included in the other data 534.

Various techniques may be used to increase the overall uptime of an individual SFD 104, and functionality of the floor 102 as a whole. In one implementation, the SFD 104 may include additional components to provide for failover redundancy. For example, the SFD 104 may include at least two hardware processors 522, each of which is able to generate other data 534, generate device output data 126, and so forth. In another example, the SFD 104 may include two power supplies 520, each connected to a different bus or power supply 118.

To provide additional redundancy, adjacent SFDs 104 may be connected to different networks 120. For example, an SFD 104 may be connected to a first network 120(1) while the SFD 104 immediately to the right may be connected to a second network 120(2).

The SFD 104 may be configured to perform diagnostics of onboard components, adjacent SFDs 104, and so forth. For example, the SFD 104 may be configured to test the receiver 530 and the transmitter 532 by transmitting a signal from the first antenna 504(1) and listening with the receiver 530 with a second antenna 504(2) that is adjacent to the first antenna 504(1). In some implementations, the SFD 104 may be configured to send diagnostic data using the network 120. For example, diagnostic data may be sent to the inventory management system 130 indicating that a particular SFD 104 has a fault and requires repair or replacement. The SFD 104 may be designed in a modular fashion to allow for repair or replacement without affecting adjacent SFDs 104.

In some implementations, operation of the SFD 104 or the segments 404 therein may be responsive to presence or absence of an object. For example, segments 404 that are proximate to or underneath the object forming a shape may be deemed active segments. Antennas 504 associated with these active segments may be used to transmit or receive the EMS 106. Inactive segments comprise segments 404 that are not underneath or proximate to the shape. The determination of whether a segment 404 is active or not may be based at least in part on output from the sensors 506, antennas 504, or other sensors. For example, a segment 404 may be deemed to be an active segment when the associated sensor element exhibits a capacitance value that exceeds a threshold level.

During operation, the determination of which segments 404 are active may be used to determine which antennas 504 are used to one or more of transmit or receive the EMS 106. For example, the antennas 504 beneath inactive segments may be disconnected from receivers 530, or the receivers 530 associated with those antennas 504 may be placed in a low power mode or turned off. As an object is detected by the sensor 506 as driven using the sensor electronics 512, a particular segment 404 may be designated as an active segment. The antenna 504 and associated radio frequency elements such as the receiver 530 and the transmitter 532 associated with that antenna 504 may be transitioned to an operational mode. Continuing the example, the receiver 530 may begin listening for an EMS 106.

The SFD 104, or portions thereof such as segments 404, may transition from a receive mode to a transmit mode or vice versa. This transition may be responsive to the detection of an object by the sensor 506. For example, the presence of an object followed by the absence of the object may result in the SFD 104 transitioning from the transmit mode to the receive mode.

By selectively transmitting the EMS 106 using antennas 504 that are within a threshold distance of the shape as determined by the sensors 506, performance of the system may be improved. For example, power consumption may be reduced by transmitting using only those antennas 504 that are proximate to the object producing the shape. In other implementations, the transmitters 532 may be activated on a particular schedule, such as transmitting for 50 milliseconds (ms) duration with a gap waiting time of 100 ms before the next transmission. This reduction in duty cycle decreases power consumption.

In some implementations, segments 404 may be in transmit mode while the receiver 530 is still active. For example, the transmitters 532 may transmit while the receiver 530 is listening.

The sensors 506 in the SFD 104 may be used to determine the presence of hazardous conditions at the SFD 104. For example, the sensors 506 may be able to detect a liquid that is present on the flooring material 502 that may comprise a slipping hazard. Continuing the example, a puddle of water on the flooring material 502 may be detected. Information indicative of the puddle may be provided to the inventory management system 130 for mitigation, such as clean up. In another example, the sensors 506 may be able to detect a user 112 lying on the flooring material 502. Upon such detection, an attendant of the facility may be alerted to provide assistance to the user 112. With this example, the floor 102 provides information to the operators of the facility that may be used to improve the safety of the facility for the users 112.

The SFD 104 may be implemented in a variety of form factors including, but not limited to, rigid floor tiles, semi rigid floor tiles, flexible tiles, flexible sections, and so forth. In one implementation, the SFD 104 may comprise a rigid floor tile, such as when the support structure 508 prevents flexure during typical handling and use. In another implementation, one or more SFDs 104 may be affixed to a flexible backing such as an elastomeric material or a textile. In this implementation, one or more SFDs 104 may be rolled up, as with a carpet, for easier storage and transport prior to installation. With this implementation, one or more of the components may be designed to flex. For example, the antennas 504 may comprise conductive materials on a flexible substrate, the electronics 512 may comprise low-profile components interconnected by a flexible printed circuit board, and so forth.

Figure 6:
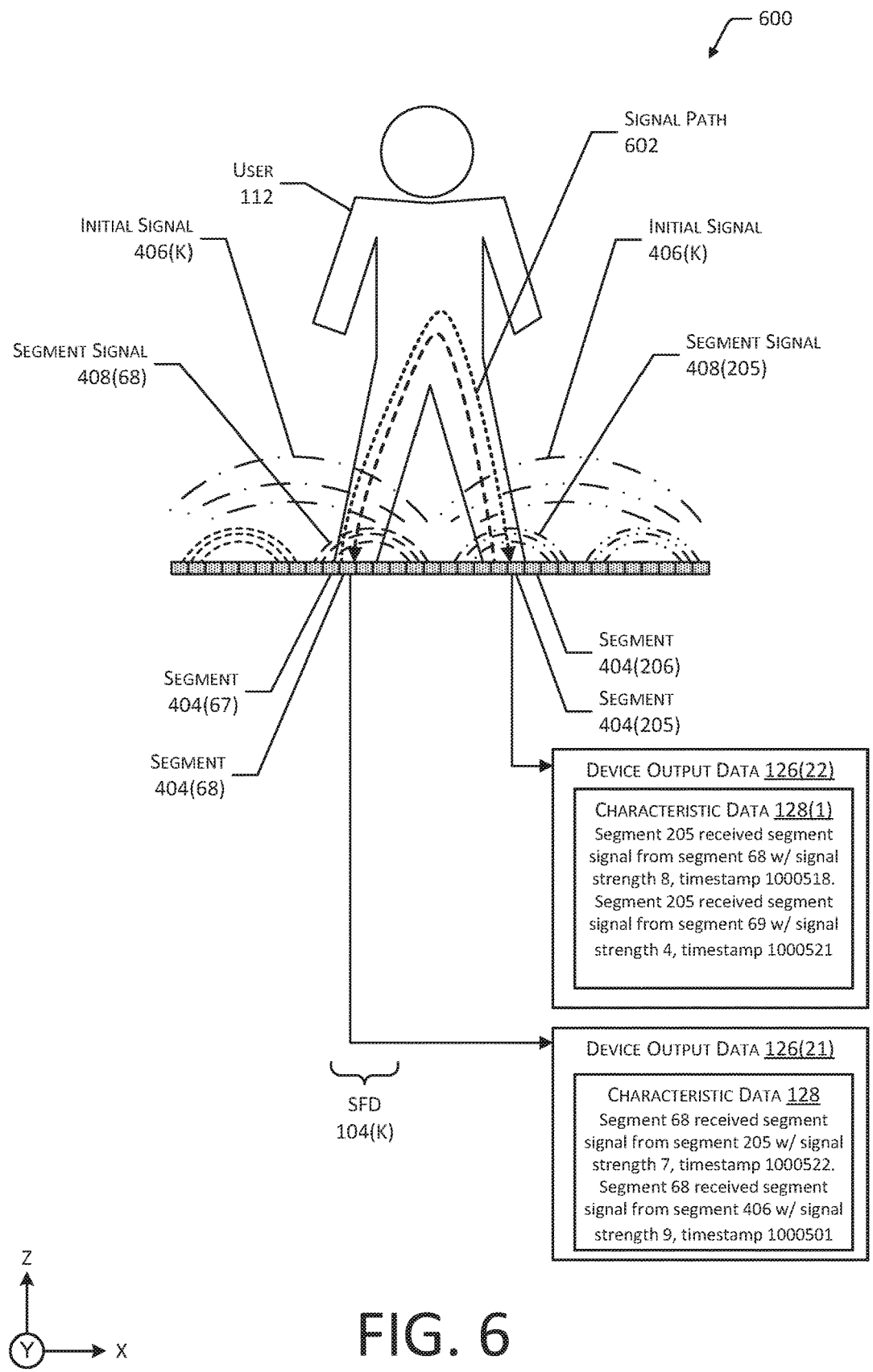
FIG. 6 illustrates cross-coupling of signals transmitted by the smart floor devices and the corresponding device output data, according to some implementations.

FIG. 6 illustrates at 600 the mixing of EMS 106 transmitted simultaneously by the SFDs 104, according to some implementations. The body of the user 112, or another object proximate to the antenna 504, may electromagnetically couple to the antenna 504. This electromagnetic coupling may include, but is not limited to, capacitive coupling, electrostatic coupling, inductive coupling, and so forth. In other implementations, other types of coupling may take place. Once coupled, a signal path 602 is provided that incorporates the body of the user 112, their clothing, other users 112 they are in contact with, and so forth. This signal path 602 provides a path by which the signals are cross-coupled from one part of the user 112 to another.

As described above and illustrated here, each SFD 104 and the respective segments 404 thereof may transmit signals at a particular frequency and during particular timeslots 410. In some implementations each segment 404 may emit from its respective one or more antennas 504 both the initial signal 406 and the respective segment signal 408. In this example, the user 112 is standing with a left foot on segments 404(67) and 404(68), and thus the body of the user 112 acts as the signal path 602 of the EMS 106 to a right foot on segments 404(205) and 404(206), and vice versa. Each of the SFDs 104 produces device output data 126 that is indicative of the segment identifier data 538 of the receiving segment 404.

The SFD 104 produces device output data 126 that is indicative of the signals received by the SFD 104 at the different timeslots 410. With the characteristic data 128, the frequency of the signal, the combination of the various timeslots 410 presented and their received signal strength provides information as to the placement of the foot with respect to a SFD 104. As the foot of the user 112 rests across different segments 404, and possibly different SFDs 104, it electromagnetically couples to the antennas 504 therein.

The device output data 126 thus provides information about the location of a foot. Given the exchange of EMS 106 from one SFD 104 to another, a pair of SFDs 104 (or locations therein) may be determined. Because of the reciprocity of the exchanges of EMS 106 and the resulting characteristic data 128, the two feet may be associated with a single user 112. In some implementations, the location 320 of the user 112 may be determined to be between the centroid locations 222 of the ORs associated with the user ID 318. For example, if each foot is a single OR, the tracking module 134 may generate user track data 136 that indicates the location of the user 112 is at a midpoint between their left and right footprints. In situations in which a single OR is associated with multiple OR IDs 218, the centroid of that single OR may be used to determine the location of multiple users 112.

The tracking module 134 may utilize certain assumptions or rules in the determination of a location of the user 112. For example, the user 112 may be assumed to have two feet, the feet may be assumed to have a minimum length of 5 inches but less than 20 inches, and so forth. The tracking module 134 may also utilize data about the physical layout of the facility. For example, the physical arrangement of the SFDs 104 with respect to one another, the arrangement of the segments 404 therein, and so forth, may be used.

Figure 7:
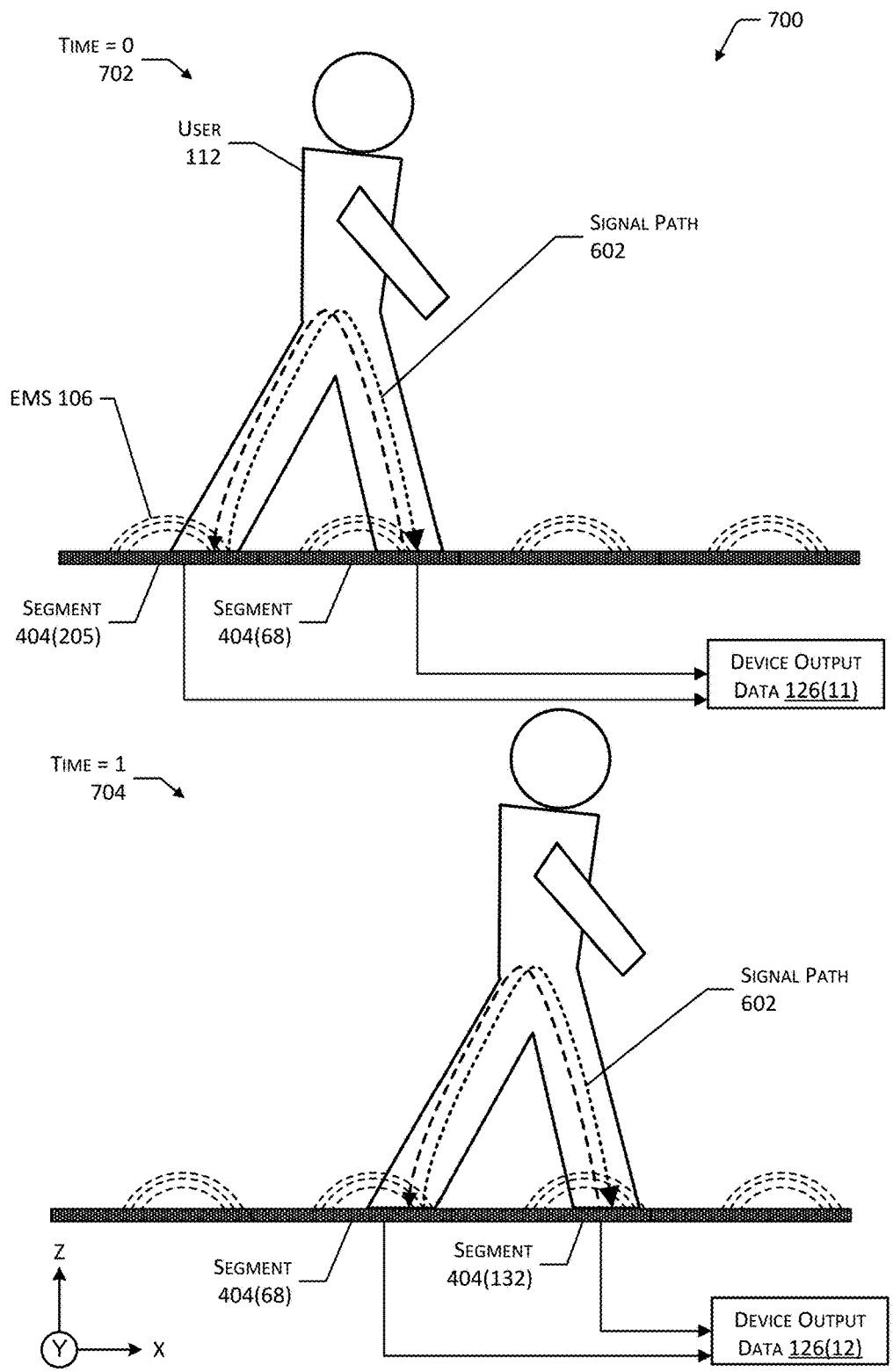
FIG. 7 illustrates cross-coupling of signals by a user as they move across the smart floor devices, according to some implementations.

FIG. 7 illustrates cross-coupling of signals 700 by a user 112 as they move across the SFDs 104. At 702, the user 112 is shown at a first time=0. Device output data 126(11) is produced that includes samples of characteristic data 128 from different segments 404. In particular, the left foot of the user 112 is detected at segment 404(205) and the right foot of the user 112 is at segment 404(68).

At 704, the user 112 is shown at a second time=1. The right foot of the user 112 is still at segment 404(68) while the left foot has moved to segment 404(132).

Figure 8:
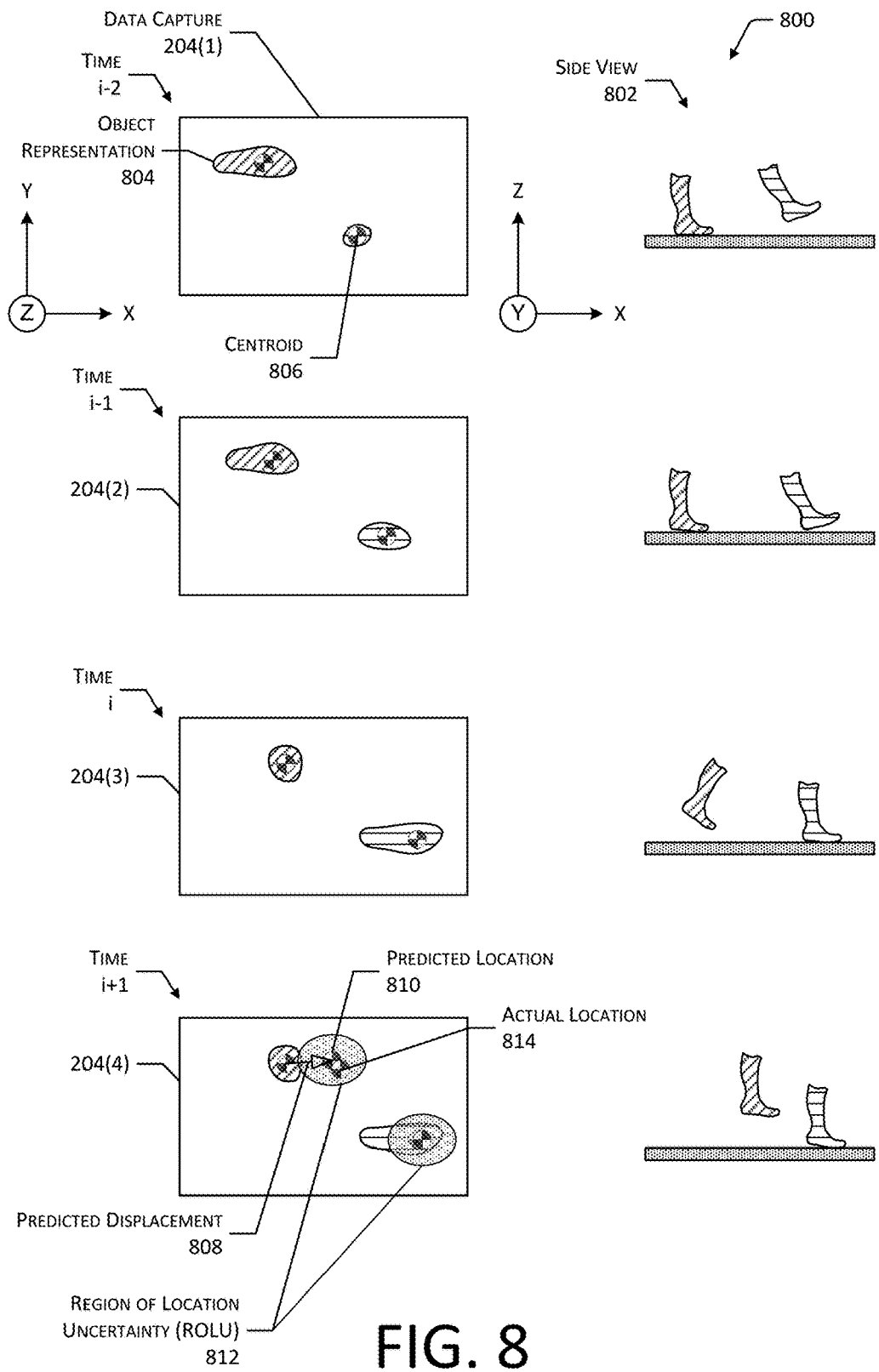
FIG. 8 illustrates a series of data captures showing object representations (ORs) associated with a user walking, according to some implementations.

FIG. 8 illustrates a series 800 of data captures 204 showing ORs associated with a user 112 walking, according to some implementations. On the left of this figure are visual representations of data captures 204(1) through 204(4) corresponding to times i−2, i−1, i, and i+1, respectively. On the right of this figure are side view(s) 802 of the feet of the user 112 corresponding to the data captures 204. ORs 804 are depicted in the data captures 204. Centroids 806 for each OR are also shown. As time progresses across these successive data captures 204, the location and shape of the ORs 804 change as the distance of the user's 112 feet change height and location with respect to the floor 102. The SFD 104 is able to detect the presence of objects that are above the floor 102. For example, the raised right foot of the user 112 depicted in the side view 802 at time i−2 is detected as illustrated by the corresponding OR in data capture 204(1).

As described above, the prediction module 214 may be used to determine a predicted displacement 808 of the centroid or another feature of an OR. For example, the prediction module 214 may use a linear quadratic estimation (LQE) algorithm, also known as Kalman filtering, to use the successive locations of the centroids 806 for the respective ORs 804 during times i−2, i−1, and i to determine a predicted displacement 808 of the centroid 806 at time i+1. Based on the predicted displacement 808, a predicted location 810 of the centroid 806 at time i may be calculated. A region of location uncertainty (ROLU) 812 may be determined. The ROLU 812 may be centered at the predicted location 810.

The ROLU 812 may extend away from this predicted location 810, describing an area in which the OR may be expected to be at time i. The size and shape of the ROLU 812 may be based on one or more factors including a maximum expected displacement of a foot during a time interval between successive data captures 204, a direction of travel indicated by prior centroid locations, speed of the OR, rate at which data capture 204 are acquired, and so forth. For example, as the speed of the OR increases, the area of the ROLU 812 may increase.

Figure 9:
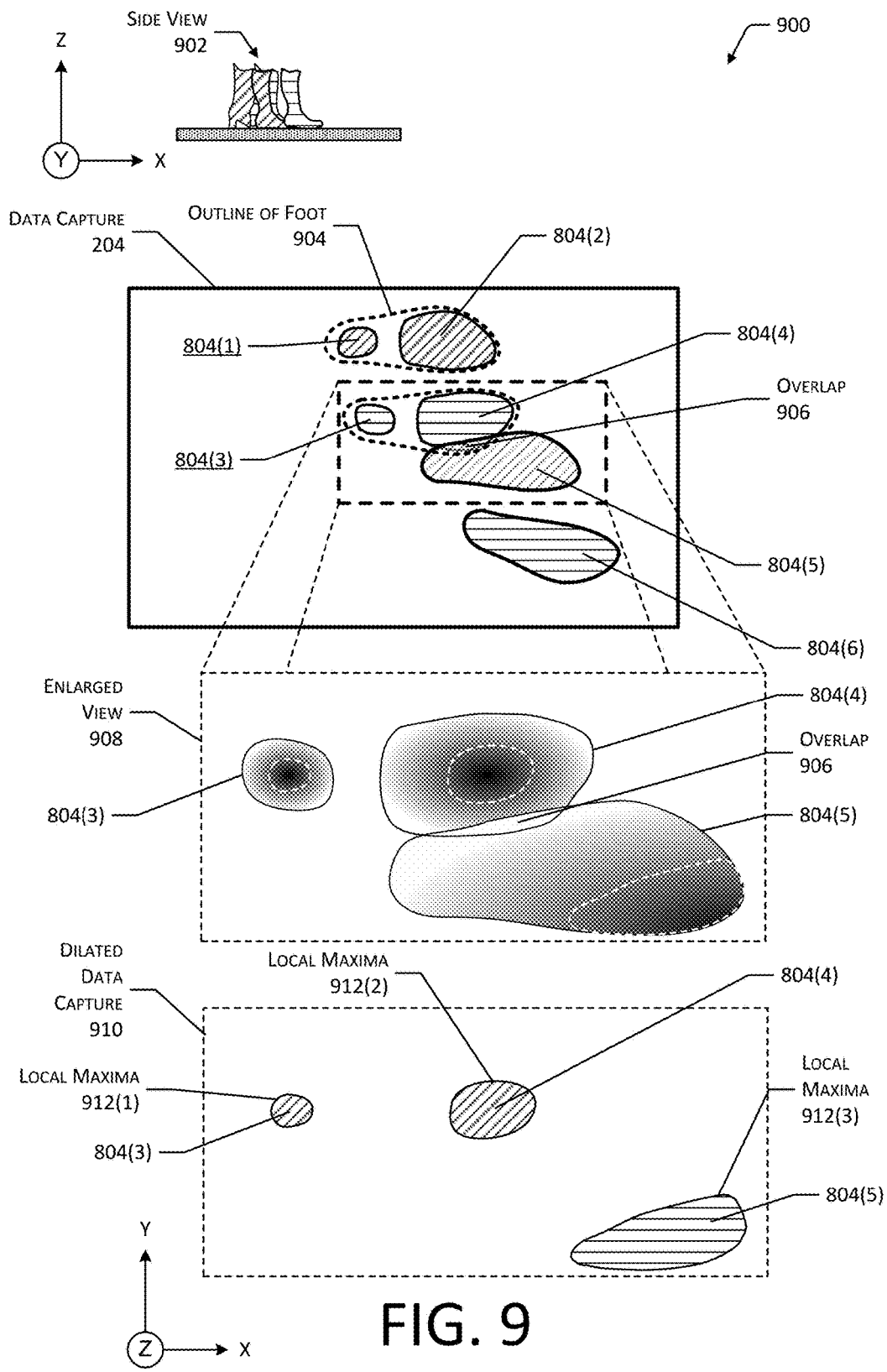
FIG. 9 illustrates a scenario of an OR merger and use of a dilation function to maintain separation between ORs, according to some implementations.

FIG. 9 illustrates a scenario 900 of an OR merger and use of a dilation function to maintain separation between ORs, according to some implementations. In this illustration a side view 902 shows the feet of two users 112 in a situation in which the two users 112 are standing close to one another, with a right foot of one user 112(1) touching a left foot of another user 112(2).

A data capture 204 shows the ORs generated by the OR detection module 206. Also shown, with a dotted line, are outlines of the respective feet 904. The user 112(1) is wearing shoes with taller heels, and as a result each foot exhibits two ORs. For example, the left foot of user 112(1) comprises ORs 804(1) and 804(2), while the right foot comprises ORs 804(3) and 804(4). Also shown are the ORs for the feet of the user 112(2), with OR 804(5) of the left foot and OR 804(6) of the right foot. Because of the size of the segments, and the radiation pattern of the EMS 106, the perimeter of an OR may extend beyond a perimeter of the foot or other object that the OR represents. For example, a perimeter of OR 804(5) overlaps 906 a perimeter of the OR 804(4).

Other situations may also produce an overlap 906 between ORs. For example, the user 112(2) may accidentally step on the foot of another user 112(1). In another example, a single user 112 may place one foot atop the other.

An enlarged view 908 depicts the overlap 906 and the corresponding ORs. Also depicted in the enlarged view is a graphical representation of the relative intensity of the received signal strength for different areas of the ORs. In this representation, darker colors indicate increased received signal strength.

As a result of the overlap 906, OR 804(4) and 804(5) may be subsequently merged. To mitigate such a merger, the OR merger module 230 may be used. For example, the OR merger module 230 may utilize a dilating kernel algorithm to produce a dilated data capture 910. As illustrated in the dilated data capture 910, ORs 804(4) and 804(5) are now clearly distinct from one another, and no longer overlap 906. The dilating kernel algorithm has reduced the area of the ORs such that the ORs are more tightly distributed around local maxima 912. The resulting dilated ORs may subsequently be associated with their respective OR IDs 218 and tracked.

Figure 10:
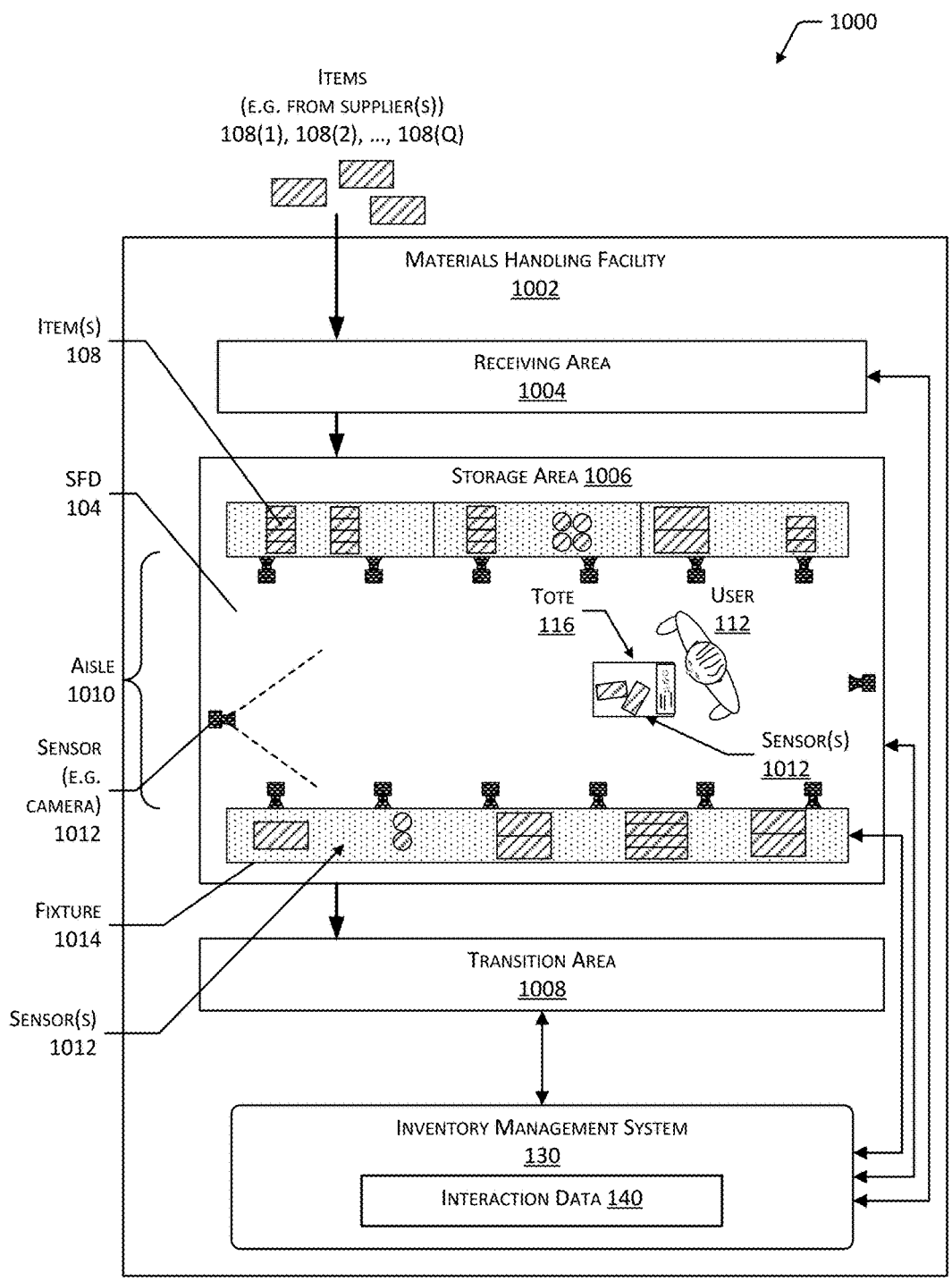
FIG. 10 is a block diagram illustrating a materials handling facility (facility) using the system, according to some implementations.

FIG. 10 is a block diagram 1000 illustrating a materials handling facility (facility) 1002 using the system 100, according to some implementations. A facility 1002 comprises one or more physical structures or areas within which one or more items 108(1), 108(2), ..., 108(Q) may be held. The items 108 may comprise physical goods, such as books, pharmaceuticals, repair parts, electronic gear, and so forth.

The facility 1002 may include one or more areas designated for different functions with regard to inventory handling. In this illustration, the facility 1002 includes a receiving area 1004, a storage area 1006, and a transition area 1008. Throughout the facility 1002, the plurality of SFDs 104 may be deployed as described above.

The receiving area 1004 may be configured to accept items 108, such as from suppliers, for intake into the facility 1002. For example, the receiving area 1004 may include a loading dock at which trucks or other freight conveyances unload the items 108. In some implementations, the items 108 may be processed, such as at the receiving area 1004, to generate at least a portion of item data as described below. For example, an item 108 may be tested at the receiving area 1004 to determine the attenuation of an EMS 106 passing through it, and this information stored as item data.

The storage area 1006 is configured to store the items 108. The storage area 1006 may be arranged in various physical configurations. In one implementation, the storage area 1006 may include one or more aisles 1010. The aisle 1010 may be configured with, or defined by, the fixtures on one or both sides of the aisle 1010. The fixtures may include one or more of a shelf, a rack, a case, a cabinet, a bin, a floor location, or other suitable storage mechanisms for holding, supporting, or storing the items 108. For example, the fixtures may comprise shelves with lanes designated therein. The fixtures may be affixed to the floor 102 or another portion of the structure of the facility 1002. The fixtures may also be movable such that the arrangements of aisles 1010 may be reconfigurable. In some implementations, the fixtures may be configured to move independently of an outside operator. For example, the fixtures may comprise a rack with a power source and a motor, operable by a computing device to allow the rack to move from one location within the facility 1002 to another.

One or more users 112(1), 112(2), ..., 112(U) and totes 116(1), 116(2), ..., 116(T) or other material handling apparatus may move within the facility 1002. For example, the user 112 may move about within the facility 1002 to pick or place the items 108 in various fixtures, placing them on the tote 116 for ease of transport. The tote 116 is configured to carry or otherwise transport one or more items 108. For example, the tote 116 may include a basket, cart, bag, bin, and so forth. In other implementations, other material handling apparatuses such as robots, forklifts, cranes, aerial drones, and so forth, may move about the facility 1002 picking, placing, or otherwise moving the items 108. For example, a robot may pick an item 108 from a first fixture and move the item 108 to a second fixture.

One or more sensors 1012 may be configured to acquire information in the facility 1002. The sensors 1012 may include, but are not limited to, weight sensors 1012(1), capacitive sensors 1012(2), image sensors 1012(3), depth sensors 1012(4), and so forth. The weight sensors 1012(1) may comprise the same or different hardware as the weight sensors described above. The sensors 1012 may be stationary or mobile, relative to the facility 1002. For example, the fixtures may contain weight sensors 1012(1) to acquire weight sensor data of items 108 stowed therein, image sensors 1012(3) to acquire images of picking or placement of items 108 on shelves, optical sensor arrays to detect shadows of the user's 112 hands at the fixtures, and so forth. In another example, the facility 1002 may include image sensors 1012(3) to obtain images of the user 112 or other objects in the facility 1002.

While the storage area 1006 is depicted as having one or more aisles 1010, fixtures storing the items 108, sensors 1012, and so forth, it is understood that the receiving area 1004, the transition area 1008, or other areas of the facility 1002 may be similarly equipped. Furthermore, the arrangement of the various areas within the facility 1002 is depicted functionally rather than schematically. For example, in some implementations, multiple different receiving areas 1004, storage areas 1006, and transition areas 1008 may be interspersed rather than segregated in the facility 1002.

The facility 1002 may include, or be coupled to, the inventory management system 130. The inventory management system 130 is configured to interact with one or more of the users 112 or devices such as sensors 1012, robots, material handling equipment, computing devices, and so forth, in one or more of the receiving area 1004, the storage area 1006, or the transition area 1008.

During operation of the facility 1002, the sensors 1012 may be configured to provide sensor data, or information based on the sensor data, to the inventory management system 130. The sensor data may include the weight data, the capacitance data, the image data, and so forth. The sensors 1012 are described in more detail below with regard to FIG. 11.

The inventory management system 130 or other systems may use the sensor data to track the location of objects within the facility 1002, movement of the objects, or provide other functionality. Objects may include, but are not limited to, items 108, users 112, totes 116, and so forth. For example, a series of images acquired by the image sensor 1012(3) may indicate removal by the user 112 of an item 108 from a particular location on the fixture and placement of the item 108 on or at least partially within the tote 116.

The facility 1002 may be configured to receive different kinds of items 108 from various suppliers and to store them until a customer orders or retrieves one or more of the items 108. A general flow of items 108 through the facility 1002 is indicated by the arrows of FIG. 10. Specifically, as illustrated in this example, items 108 may be received from one or more suppliers, such as manufacturers, distributors, wholesalers, and so forth, at the receiving area 1004. In various implementations, the items 108 may include merchandise, commodities, perishables, or any suitable type of item 108, depending on the nature of the enterprise that operates the facility 1002.

Upon being received from a supplier at the receiving area 1004, the items 108 may be prepared for storage in the storage area 1006. For example, in some implementations, items 108 may be unpacked or otherwise rearranged. The inventory management system 130 may include one or more software applications executing on a computer system to provide inventory management functions. These inventory management functions may include maintaining information indicative of the type, quantity, condition, cost, location, weight, or any other suitable parameters with respect to the items 108. The items 108 may be stocked, managed, or dispensed in terms of countable units, individual units, or multiple units, such as packages, cartons, crates, pallets, or other suitable aggregations. Alternatively, some items 108, such as bulk products, commodities, and so forth, may be stored in continuous or arbitrarily divisible amounts that may not be inherently organized into countable units. Such items 108 may be managed in terms of a measurable quantity such as units of length, area, volume, weight, time, duration, or other dimensional properties characterized by units of measurement. Generally speaking, a quantity of an item 108 may refer to either a countable number of individual or aggregate units of an item 108 or a measurable amount of an item 108, as appropriate.

After arriving through the receiving area 1004, items 108 may be stored within the storage area 1006. In some implementations, like items 108 may be stored or displayed together in the fixtures such as in bins, on shelves, hanging from pegboards, and so forth. For example, all items 108 of a given kind are stored in one fixture. In other implementations, like items 108 may be stored in different fixtures. For example, to optimize retrieval of certain items 108 having frequent turnover within a large physical facility 1002, those items 108 may be stored in several different fixtures to reduce congestion that might occur at a single fixture.

When a customer order specifying one or more items 108 is received, or as a user 112 progresses through the facility 1002, the corresponding items 108 may be selected or "picked" from the fixtures containing those items 108. In various implementations, item picking may range from manual to completely automated picking. For example, in one implementation, a user 112 may have a list of items 108 they desire and may progress through the facility 1002 picking items 108 from the fixtures within the storage area 1006 and placing those items 108 into a tote 116. In other implementations, employees of the facility 1002 may pick items 108 using written or electronic pick lists derived from customer orders. These picked items 108 may be placed into the tote 116 as the employee progresses through the facility 1002.

After items 108 have been picked, the items 108 may be processed at a transition area 1008. The transition area 1008 may be any designated area within the facility 1002 where items 108 are transitioned from one location to another or from one entity to another. For example, the transition area 1008 may be a packing station within the facility 1002. When the item 108 arrives at the transition area 1008, the item 108 may be transitioned from the storage area 1006 to the packing station. Information about the transition may be maintained by the inventory management system 130.

In another example, if the items 108 are departing the facility 1002, a list of the items 108 may be obtained and used by the inventory management system 130 to transition responsibility for, or custody of, the items 108 from the facility 1002 to another entity. For example, a carrier may accept the items 108 for transport with that carrier accepting responsibility for the items 108 indicated in the list. In another example, a user 112 may purchase or rent the items 108 and remove the items 108 from the facility 1002. During use of the facility 1002, the user 112 may move about the facility 1002 to perform various tasks, such as picking or placing the items 108 in the fixtures.

The inventory management system 130 may generate the interaction data 140. The interaction data 140 may be based at least in part on one or more of the device output data 126, the fixture data, and so forth. The interaction data 140 may provide information about an interaction, such as a pick of an item 108 from the fixture, a place of an item 108 to the fixture, a touch made to an item 108 at the fixture, a gesture associated with an item 108 at the fixture, and so forth. The interaction data 140 may include one or more of the type of interaction, duration of interaction, interaction location identifier indicative of where from the fixture the interaction took place, item identifier, quantity change to the item 108, user identifier, and so forth. The interaction data 140 may then be used to further update the item data. For example, the quantity of items 108 on hand at a particular lane on the shelf may be changed based on an interaction that picks or places one or more items 108.

The inventory management system 130 may combine or otherwise utilize data from different sensors 1012 of different types. For example, weight data obtained from weight sensors 1012(1) at the fixture may be used instead of, or in conjunction with, one or more of the capacitance data to determine the interaction data 140.

Figure 11:
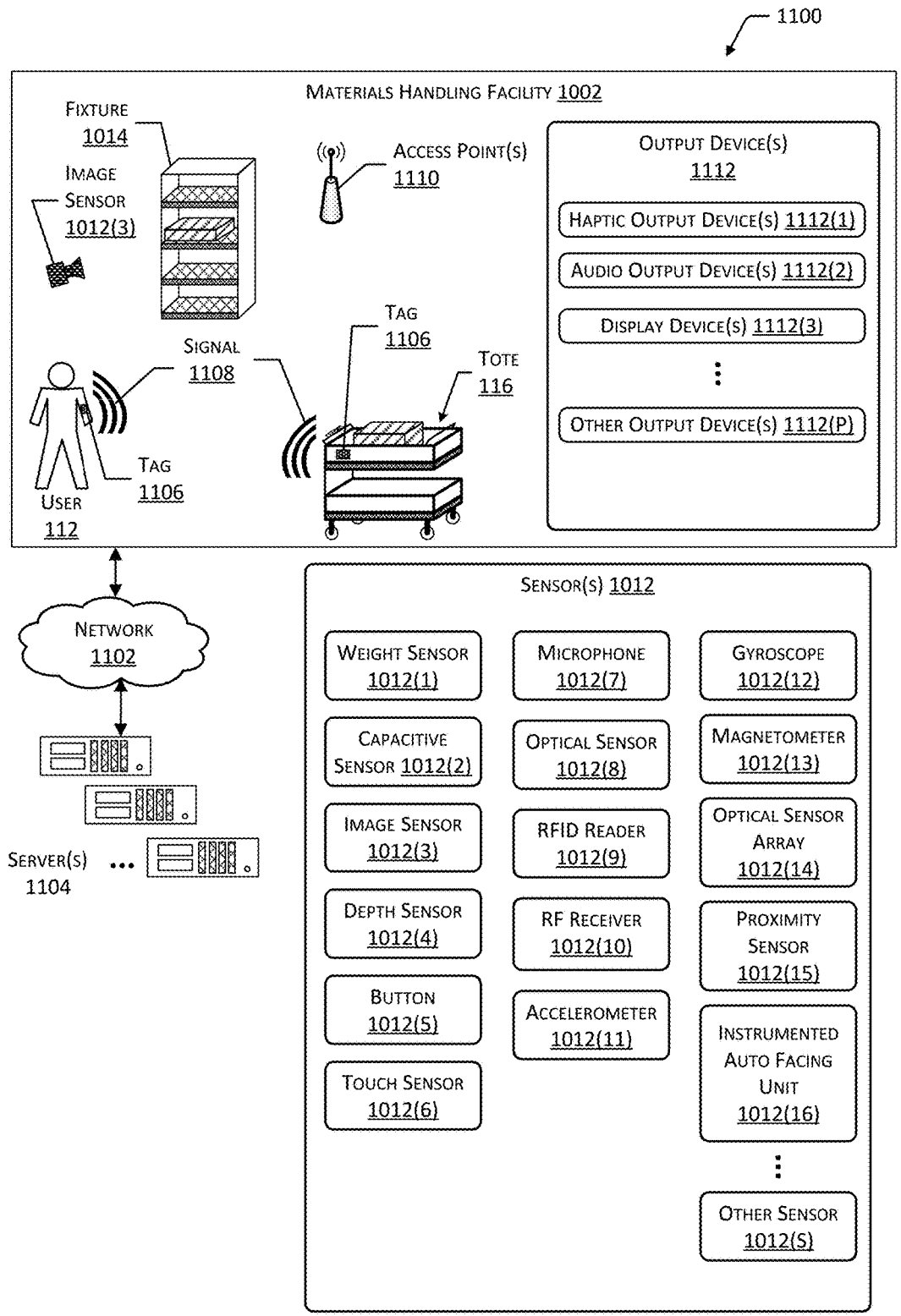
FIG. 11 is a block diagram illustrating additional details of the facility, according to some implementations.

FIG. 11 is a block diagram 1100 illustrating additional details of the facility 1002, according to some implementations. The facility 1002 may be connected to one or more networks 1102, which in turn connect to one or more servers 1104. The network 1102 may include private networks such as an institutional or personal intranet, public networks such as the Internet, or a combination thereof. The network 1102 may utilize wired technologies (e.g., wires, fiber optic cables, and so forth), wireless technologies (e.g., radio frequency, infrared, acoustic, optical, and so forth), or other connection technologies. The network 1102 is representative of any type of communication network, including one or more of data networks or voice networks. The network 1102 may be implemented using wired infrastructure (e.g., copper cable, fiber optic cable, and so forth), a wireless infrastructure (e.g., cellular, microwave, satellite, and so forth), or other connection technologies.

The servers 1104 may be configured to execute one or more modules or software applications associated with the inventory management system 130 or other systems. While the servers 1104 are illustrated as being in a location outside of the facility 1002, in other implementations, at least a portion of the servers 1104 may be located at the facility 1002. The servers 1104 are discussed in more detail below with regard to FIG. 12.

The users 112, the totes 116, or other objects in the facility 1002 may be equipped with one or more tags 1106. The tags 1106 may be configured to emit a signal 1108. In one implementation, the tag 1106 may be a RFID tag 1106 configured to emit a RF signal 1108 upon activation by an external signal. For example, the external signal may comprise a radio frequency signal or a magnetic field configured to energize or activate the RFID tag 1106. In another implementation, the tag 1106 may comprise a transmitter and a power source configured to power the transmitter. For example, the tag 1106 may comprise a Bluetooth Low Energy (BLE) transmitter and battery. In other implementations, the tag 1106 may use other techniques to indicate presence of the tag 1106. For example, an acoustic tag 1106 may be configured to generate an ultrasonic signal 1108, which is detected by corresponding acoustic receivers. In yet another implementation, the tag 1106 may be configured to emit an optical signal 1108.

The inventory management system 130 may be configured to use the tags 1106 for one or more of identification of the object, determining a location of the object, and so forth. For example, the users 112 may wear tags 1106, the totes 116 may have tags 1106 affixed, and so forth, which may be read and, based at least in part on signal strength, used to determine identity and location. In other implementations the users 112 may wear portable transmitters, the totes 116 may be equipped with a portable receiver, portable transmitter, and so forth. In some implementations, the two may be combined, such as tags 1106 and the use of a portable transmitter.

Generally, the inventory management system 130 or other systems associated with the facility 1002 may include any number and combination of input components, output components, and servers 1104.

The one or more sensors 1012 may be arranged at one or more locations within the facility 1002. For example, the sensors 1012 may be mounted on or within a floor 102, wall, at a ceiling, at fixture 1014, on a tote 116, may be carried or worn by a user 112, and so forth.

The sensors 1012 may include one or more weight sensors 1012(1) that are configured to measure the weight of a load, such as the item 108, the tote 116, or other objects. The weight sensors 1012(1) may be configured to measure the weight of the load at one or more of the fixtures 1014, the tote 116, on the floor 102 of the facility 1002, and so forth. For example, the shelf may include a plurality of lanes or platforms, with one or more weight sensors 1012(1) beneath each one to provide weight sensor data about an individual lane or platform. The weight sensors 1012(1) may include one or more sensing mechanisms to determine the weight of a load. These sensing mechanisms may include piezoresistive devices, piezoelectric devices, capacitive devices, electromagnetic devices, optical devices, potentiometric devices, microelectromechanical devices, and so forth. The sensing mechanisms of weight sensors 1012(1) may operate as transducers that generate one or more signals based on an applied force, such as that of the load due to gravity. For example, the weight sensor 1012(1) may comprise a load cell having a strain gauge and a structural member that deforms slightly when weight is applied. By measuring a change in the electrical characteristic of the strain gauge, such as capacitance or resistance, the weight may be determined. In another example, the weight sensor 1012(1) may comprise a force sensing resistor (FSR). The FSR may comprise a resilient material that changes one or more electrical characteristics when compressed. For example, the electrical resistance of a particular portion of the FSR may decrease as the particular portion is compressed. The inventory management system 130 may use the data acquired by the weight sensors 1012(1) to identify an object, determine a change in the quantity of objects, determine a location of an object, maintain shipping records, and so forth.

The sensors 1012 may include capacitive sensors 1012(2). The capacitive sensor 1012(2) may comprise one or more conductive elements and the capacitance measurement/receiver module. In some implementations, the capacitive sensor 1012(2) may include or utilize a switch module. The capacitive sensor 1012(2) may be configured to use a far-field capacitance effect that may comprise measuring the self-capacitance of the conductive elements, rather than a mutual capacitance. In one implementation, a fixed charge may be provided to the conductive element, and the resultant voltage may be measured between the conductive element and the ground.

In other implementations, the capacitive sensor 1012(2) may be configured to operate in a mutual capacitance mode, surface capacitance mode, and so forth. In mutual capacitance mode, at least two conductive layers are arranged in a stack with a dielectric material between the layers. The dielectric may be a solid, such as a plastic, a gas such as air, a vacuum, and so forth. The mutual capacitance at points between these layers is measured. When another object touches the outermost conductive layer, the mutual capacitance between the two layers changes, allowing for detection. In surface capacitance mode, voltages are applied to different points of a conductive element to produce an electrostatic field. By measuring the changes in current draw (or another electrical characteristic) from the different points at which voltage is applied, a location of an object may be determined.

The sensors 1012 may include one or more image sensors 1012(3). The one or more image sensors 1012(3) may include imaging sensors configured to acquire images of a scene. The image sensors 1012(3) are configured to detect light in one or more wavelengths including, but not limited to, terahertz, infrared, visible, ultraviolet, and so forth. The image sensors 1012(3) may comprise charge coupled devices (CCD), complementary metal oxide semiconductor (CMOS) devices, microbolometers, and so forth. The inventory management system 130 may use image data acquired by the image sensors 1012(3) during operation of the facility 1002. For example, the inventory management system 130 may identify items 108, users 112, totes 116, and so forth, based at least in part on their appearance within the image data acquired by the image sensors 1012(3). The image sensors 1012(3) may be mounted in various locations within the facility 1002. For example, image sensors 1012(3) may be mounted overhead, on the fixtures 1014, may be worn or carried by users 112, may be affixed to totes 116, and so forth.

One or more depth sensors 1012(4) may also be included in the sensors 1012. The depth sensors 1012(4) are configured to acquire spatial or three-dimensional (3D) data, such as depth information, about objects within a field-of-view (FOV). The depth sensors 1012(4) may include range cameras, lidar systems, sonar systems, radar systems, structured light systems, stereo vision systems, optical interferometry systems, and so forth. The inventory management system 130 may use the 3D data acquired by the depth sensors 1012(4) to identify objects, determine a location of an object in 3D real space, and so forth.

One or more buttons 1012(5) may be configured to accept input from the user 112. The buttons 1012(5) may comprise mechanical, capacitive, optical, or other mechanisms. For example, the buttons 1012(5) may comprise mechanical switches configured to accept an applied force from a touch of the user 112 to generate an input signal. The inventory management system 130 may use data from the buttons 1012(5) to receive information from the user 112. For example, the tote 116 may be configured with a button 1012(5) to accept input from the user 112 and send information indicative of the input to the inventory management system 130.

The sensors 1012 may include one or more touch sensors 1012(6). The touch sensors 1012(6) may use resistive, capacitive, surface capacitance, projected capacitance, mutual capacitance, optical, Interpolating Force-Sensitive Resistance (IFSR), or other mechanisms to determine the position of a touch or near-touch. For example, the IFSR may comprise a material configured to change electrical resistance responsive to an applied force. The location within the material of that change in electrical resistance may indicate the position of the touch. The inventory management system 130 may use data from the touch sensors 1012(6) to receive information from the user 112. For example, the touch sensor 1012(6) may be integrated with the tote 116 to provide a touchscreen with which the user 112 may select from a menu one or more particular items 108 for picking, enter a manual count of items 108 at fixture, and so forth.

One or more microphones 1012(7) may be configured to acquire information indicative of sound present in the environment. In some implementations, arrays of microphones 1012(7) may be used. These arrays may implement beamforming techniques to provide for directionality of gain. The inventory management system 130 may use the one or more microphones 1012(7) to acquire information from acoustic tags 1106, accept voice input from the users 112, determine ambient noise level, and so forth.

The sensors 1012 may include one or more optical sensors 1012(8). The optical sensors 1012(8) may be configured to provide data indicative of one or more of color or intensity of light impinging thereupon. For example, the optical sensor 1012(8) may comprise a photodiode and associated circuitry configured to generate a signal or data indicative of an incident flux of photons. As described below, the optical sensor array 1012(14) may comprise a plurality of the optical sensors 1012(8). For example, the optical sensor 1012(8) may comprise an array of ambient light sensors such as the ISL76683 as provided by Intersil Corporation of Milpitas, Calif., USA, or the MAX44009 as provided by Maxim Integrated of San Jose, Calif., USA. In other implementations, other optical sensors 1012(8) may be used. The optical sensors 1012(8) may be sensitive to one or more of infrared light, visible light, or ultraviolet light. For example, the optical sensors 1012(8) may be sensitive to infrared light, and infrared light sources such as light emitting diodes (LEDs) may provide illumination.

The optical sensors 1012(8) may include photodiodes, photoresistors, photovoltaic cells, quantum dot photoconductors, bolometers, pyroelectric infrared detectors, and so forth. For example, the optical sensor 1012(8) may use germanium photodiodes to detect infrared light.

One or more radio frequency identification (RFID) readers 1012(9), near field communication (NFC) systems, and so forth, may be included as sensors 1012. For example, the RFID readers 1012(9) may be configured to read the RF tags 1106. Information acquired by the RFID reader 1012(9) may be used by the inventory management system 130 to identify an object associated with the RF tag 1106 such as the item 108, the user 112, the tote 116, and so forth. For example, based on information from the RFID readers 1012(9) detecting the RF tag 1106 at different times and RFID readers 1012(9) having different locations in the facility 1002, a velocity of the RF tag 1106 may be determined.

One or more RF receivers 1012(10) may also be included as sensors 1012. In some implementations, the RF receivers 1012(10) may be part of transceiver assemblies. The RF receivers 1012(10) may be configured to acquire RF signals 1108 associated with Wi-Fi, Bluetooth, ZigBee, 3G, 4G, LTE, or other wireless data transmission technologies. The RF receivers 1012(10) may provide information associated with data transmitted via radio frequencies, signal strength of RF signals 1108, and so forth. For example, information from the RF receivers 1012(10) may be used by the inventory management system 130 to determine a location of an RF source, such as a communication interface onboard the tote 116.

The sensors 1012 may include one or more accelerometers 1012(11), which may be worn or carried by the user 112, mounted to the tote 116, and so forth. The accelerometers 1012(11) may provide information such as the direction and magnitude of an imposed acceleration. Data such as rate of acceleration, determination of changes in direction, speed, and so forth, may be determined using the accelerometers 1012(11).

A gyroscope 1012(12) may provide information indicative of rotation of an object affixed thereto. For example, the tote 116 or other objects may be equipped with a gyroscope 1012(12) to provide data indicative of a change in orientation of the object.

A magnetometer 1012(13) may be used to determine an orientation by measuring ambient magnetic fields, such as the terrestrial magnetic field. The magnetometer 1012(13) may be worn or carried by the user 112, mounted to the tote 116, and so forth. For example, the magnetometer 1012(13) mounted to the tote 116 may act as a compass and provide information indicative of which direction the tote 116 is oriented.

An optical sensor array 1012(14) may comprise one or more optical sensors 1012(8). The optical sensors 1012(8) may be arranged in a regular, repeating, or periodic two-dimensional arrangement such as a grid. The optical sensor array 1012(14) may generate image data. For example, the optical sensor array 1012(14) may be arranged within or below a fixture and obtain information about shadows of items 108, hand of the user 112, and so forth.

The sensors 1012 may include proximity sensors 1012(15) used to determine presence of an object, such as the user 112, the tote 116, and so forth. The proximity sensors 1012(15) may use optical, electrical, ultrasonic, electromagnetic, or other techniques to determine a presence of an object. In some implementations, the proximity sensors 1012(15) may use an optical emitter and an optical detector to determine proximity. For example, an optical emitter may emit light, a portion of which may then be reflected by the object back to the optical detector to provide an indication that the object is proximate to the proximity sensor 1012(15). In other implementations, the proximity sensors 1012(15) may comprise a capacitive proximity sensor 1012(15) configured to provide an electrical field and determine a change in electrical capacitance due to presence or absence of an object within the electrical field.

The proximity sensors 1012(15) may be configured to provide sensor data indicative of one or more of a presence or absence of an object, a distance to the object, or characteristics of the object. An optical proximity sensor 1012(15) may use time-of-flight (ToF), structured light, interferometry, or other techniques to generate the distance data. For example, ToF determines a propagation time (or "round-trip" time) of a pulse of emitted light from an optical emitter or illuminator that is reflected or otherwise returned to an optical detector. By dividing the propagation time in half and multiplying the result by the speed of light in air, the distance to an object may be determined. In another implementation, a structured light pattern may be provided by the optical emitter. A portion of the structured light pattern may then be detected on the object using a sensor 1012 such as an image sensor 1012(3). Based on an apparent distance between the features of the structured light pattern, the distance to the object may be calculated. Other techniques may also be used to determine distance to the object. In another example, the color of the reflected light may be used to characterize the object, such as skin, clothing, tote 116, and so forth.

The sensors 1012 may also include an instrumented auto-facing unit (IAFU) 1012(16). The IAFU 1012(16) may comprise a position sensor configured to provide data indicative of displacement of a pusher. As an item 108 is removed from the IAFU 1012(16), the pusher moves, such as under the influence of a spring, and pushes the remaining items 108 in the IAFU 1012(16) to the front of the fixture. By using data from the position sensor, and given item data such as a depth of an individual item 108, a count may be determined, based on a change in position data. For example, if each item 108 is 1 inch deep, and the position data indicates a change of 17 inches, the quantity held by the IAFU 1012(16) may have changed by 17 items 108. This count information may be used to confirm or provide a cross check for a count obtained by other means, such as analysis of the weight data, the capacitance data, image data, and so forth.

The sensors 1012 may include other sensors 1012(S) as well. For example, the other sensors 1012(S) may include light curtains, ultrasonic rangefinders, thermometers, barometric sensors, air pressure sensors, hygrometers, and so forth. For example, the inventory management system 130 may use information acquired from thermometers and hygrometers in the facility 1002 to direct the user 112 to check on delicate items 108 stored in a particular fixture, which is overheating, too dry, too damp, and so forth.

In one implementation, a light curtain may utilize a linear array of light emitters and a corresponding linear array of light detectors. For example, the light emitters may comprise a line of infrared LEDs or vertical cavity surface emitting lasers (VCSELs) that are arranged in front of the fixture, while the light detectors comprise a line of photodiodes sensitive to infrared light arranged below the light emitters. The light emitters produce a "lightplane" or sheet of infrared light that is then detected by the light detectors. An object passing through the lightplane may decrease the amount of light falling upon the light detectors. For example, the user's 112 hand would prevent at least some of the light from light emitters from reaching a corresponding light detector. As a result, a position along the linear array of the object may be determined that is indicative of a touchpoint. This position may be expressed as touchpoint data, with the touchpoint being indicative of the intersection between the hand of the user 112 and the sheet of infrared light. In some implementations, a pair of light curtains may be arranged at right angles relative to one another to provide two-dimensional touchpoint data indicative of a position of touch in a plane. Input from the light curtain, such as indicating occlusion from a hand of a user 112 may be used to generate interaction data 140.

In some implementations, the image sensor 1012(3) or other sensors 1012(5) may include hardware processors, memory, and other elements configured to perform various functions. For example, the image sensors 1012(3) may be configured to generate image data, send the image data to another device such as the server 1104, and so forth.

The facility 1002 may include one or more access points 1110 configured to establish one or more wireless networks. The access points 1110 may use Wi-Fi, NFC, Bluetooth, or other technologies to establish wireless communications between a device and the network 1102. The wireless networks allow devices to communicate with one or more of the sensors 1012, the inventory management system 130, the optical sensor arrays 1012(14), the tag 1106, a communication device of the tote 116, or other devices.

Output devices 1112 may also be provided in the facility 1002. The output devices 1112 are configured to generate signals, which may be perceived by the user 112 or detected by the sensors 1012. In some implementations, the output devices 1112 may be used to provide illumination of the optical sensor array 1012(14).

Haptic output devices 1112(1) are configured to provide a signal that results in a tactile sensation to the user 112. The haptic output devices 1112(1) may use one or more mechanisms such as electrical stimulation or mechanical displacement to provide the signal. For example, the haptic output devices 1112(1) may be configured to generate a modulated electrical signal, which produces an apparent tactile sensation in one or more fingers of the user 112. In another example, the haptic output devices 1112(1) may comprise piezoelectric or rotary motor devices configured to provide a vibration, which may be felt by the user 112.

One or more audio output devices 1112(2) may be configured to provide acoustic output. The acoustic output includes one or more of infrasonic sound, audible sound, or ultrasonic sound. The audio output devices 1112(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output.

The display devices 1112(3) may be configured to provide output, which may be seen by the user 112 or detected by a light-sensitive sensor such as an image sensor 1012(3) or an optical sensor 1012(8). In some implementations, the display devices 1112(3) may be configured to produce output in one or more of infrared, visible, or ultraviolet light. The output may be monochrome or in color. The display devices 1112(3) may be one or more of emissive, reflective, microelectromechanical, and so forth. An emissive display device 1112(3), such as using LEDs, is configured to emit light during operation. In comparison, a reflective display device 1112(3), such as using an electrophoretic element, relies on ambient light to present an image. Backlights or front lights may be used to illuminate non-emissive display devices 1112(3) to provide visibility of the output in conditions where the ambient light levels are low.

The display devices 1112(3) may be located at various points within the facility 1002. For example, the addressable displays may be located on the fixtures, totes 116, on the floor of the facility 1002, and so forth.

Other output devices 1112(P) may also be present. For example, the other output devices 1112(P) may include scent/odor dispensers, document printers, 3D printers or fabrication equipment, and so forth.

Figure 12:
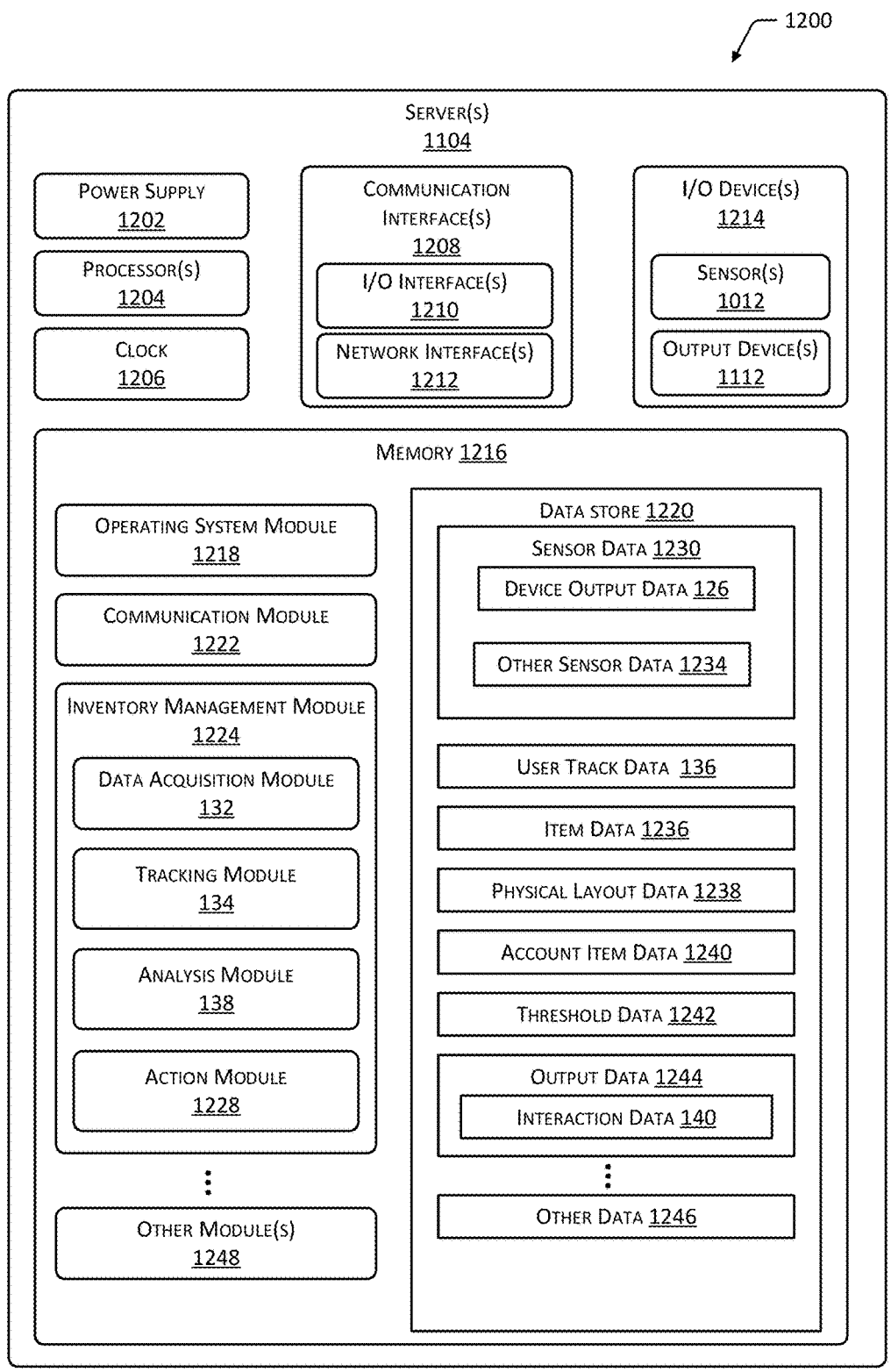
FIG. 12 is a block diagram of a server to support operation of the facility, according to some implementations.

FIG. 12 illustrates a block diagram 1200 of a server 1104 configured to support operation of the facility 1002, according to some implementations. The server 1104 may be physically present at the facility 1002, may be accessible by the network 1102, or a combination of both. The server 1104 does not require end-user knowledge of the physical location and configuration of the system that delivers the services. Common expressions associated with the server 1104 may include "on-demand computing", "software as a service (SaaS)", "platform computing", "network-accessible platform", "cloud services", "data centers", and so forth. Services provided by the server 1104 may be distributed across one or more physical or virtual devices.

One or more power supplies 1202 may be configured to provide electrical power suitable for operating the components in the server 1104. The one or more power supplies 1202 may comprise batteries, capacitors, fuel cells, photovoltaic cells, wireless power receivers, conductive couplings suitable for attachment to an external power source such as provided by an electric utility, and so forth. The server 1104 may include one or more hardware processors 1204 (processors) configured to execute one or more stored instructions. The processors 1204 may comprise one or more cores. One or more clocks 1206 may provide information indicative of date, time, ticks, and so forth. For example, the processor 1204 may use data from the clock 1206 to associate a particular interaction with a particular point in time.

The server 1104 may include one or more communication interfaces 1208 such as input/output (I/O) interfaces 1210, network interfaces 1212, and so forth. The communication interfaces 1208 enable the server 1104, or components thereof, to communicate with other devices or components. The communication interfaces 1208 may include one or more I/O interfaces 1210. The I/O interfaces 1210 may comprise Inter-Integrated Circuit (I2C), Serial Peripheral Interface bus (SPI), Universal Serial Bus (USB) as promulgated by the USB Implementers Forum, RS-232, and so forth.

The I/O interface(s) 1210 may couple to one or more I/O devices 1214. The I/O devices 1214 may include input devices such as one or more of a sensor 1012, keyboard, mouse, scanner, and so forth. The I/O devices 1214 may also include output devices 1112 such as one or more of a display device 1112(3), printer, audio speakers, and so forth. In some embodiments, the I/O devices 1214 may be physically incorporated with the server 1104 or may be externally placed.

The network interfaces 1212 may be configured to provide communications between the server 1104 and other devices, such as the SFDs 104, totes 116, routers, access points 1110, and so forth. The network interfaces 1212 may include devices configured to couple to personal area networks (PANs), local area networks (LANs), wireless local area networks (WLANS), wide area networks (WANs), and so forth. For example, the network interfaces 1212 may include devices compatible with Ethernet, Wi-Fi, Bluetooth, ZigBee, and so forth.

The server 1104 may also include one or more busses or other internal communications hardware or software that allow for the transfer of data between the various modules and components of the server 1104.

As shown in FIG. 12, the server 1104 includes one or more memories 1216. The memory 1216 may comprise one or more non-transitory computer-readable storage media (CRSM). The CRSM may be any one or more of an electronic storage medium, a magnetic storage medium, an optical storage medium, a quantum storage medium, a mechanical computer storage medium, and so forth. The memory 1216 provides storage of computer-readable instructions, data structures, program modules, and other data for the operation of the server 1104. A few example functional modules are shown stored in the memory 1216, although the same functionality may alternatively be implemented in hardware, firmware, or as a system on a chip (SoC).

The memory 1216 may include at least one operating system (OS) module 1218. The OS module 1218 is configured to manage hardware resource devices such as the I/O interfaces 1210, the I/O devices 1214, the communication interfaces 1208, and provide various services to applications or modules executing on the processors 1204. The OS module 1218 may implement a variant of the FreeBSD operating system as promulgated by the FreeBSD Project; other UNIX or UNIX-like variants; a variation of the Linux operating system as promulgated by Linus Torvalds; the Windows operating system from Microsoft Corporation of Redmond, Wash., USA; and so forth.

Also stored in the memory 1216 may be a data store 1220 and one or more of the following modules. These modules may be executed as foreground applications, background tasks, daemons, and so forth. The data store 1220 may use a flat file, database, linked list, tree, executable code, script, or other data structure to store information. In some implementations, the data store 1220 or a portion of the data store 1220 may be distributed across one or more other devices including the servers 1104, network attached storage devices, and so forth.

A communication module 1222 may be configured to establish communications with one or more of the totes 116, sensors 1012, display devices 1112(3), other servers 1104, or other devices. The communications may be authenticated, encrypted, and so forth.

The memory 1216 may store an inventory management module 1224. The inventory management module 1224 is configured to provide the inventory functions as described herein with regard to the inventory management system 130. For example, the inventory management module 1224 may track items 108 between different fixtures, to and from the totes 116, and so forth.

The inventory management module 1224 may include one or more of a data acquisition module 132, the tracking module 134, the analysis module 138, an action module 1228, and so forth. The data acquisition module 132 may be configured to acquire and access information associated with operation of the facility 1002. For example, the data acquisition module 132 may be configured to acquire device output data 126 from the SFDs 104, fixture data, sensor data 1230 such as the weight data, capacitance data, image data, other sensor data 1234, and so forth. The sensor data 1230 may be accessed by the other modules for use.

The data store 1220 may store other data associated with operation of the tracking module 134, such as described above. For example, the data store 1220 may store the user track data 136. Other data may be stored in the data store 1220, but is not depicted for clarity of illustration and not necessarily as a limitation. For example, the data store 1220 may store the OR track data 216, feature data 308, gait data 332, classifier data 312, historical gait data, and so forth.

The data store 1220 may also store item data 1236. The item data 1236 provides information about a particular type of item 108, including characteristics of that type of item 108 such as physical dimensions, where that type of item 108 is located in the facility 1002, characteristics about how the item 108 appears, and so forth. For example, the item data 1236 may indicate that the type of item 108 is "Bob's Low Fat Baked Beans, 10 oz. can" with a stock keeping unit number of "24076513". The item data 1236 may indicate the types and quantities of items 108 that are expected to be stored at that particular fixture such as in a particular lane on a shelf, width and depth of that type of item 108, weight of the item 108 individually or in aggregate, sample images of the type of item 108, and so forth.

The item data 1236 may include an item identifier. The item identifier may be used to distinguish one type of item 108 from another. For example, the item identifier may include a stock keeping unit (SKU) string, Universal Product Code (UPC) number, radio frequency identification (RFID) tag data, and so forth. The items 108 that are of the same type may be referred to by the same item identifier. For example, cans of beef flavor brand X dog food may be represented by the item identifier value of "9811901181". In other implementations, non-fungible items 108 may each be provided with a unique item identifier, allowing each to be distinguished from one another.

The item data 1236 may include one or more of geometry data, item weight data, sample image data, sample capacitance data, or other data. The geometry data may include information indicative of size and shape of the item 108 in one-, two-, or three-dimensions. For example, the geometry data may include the overall shape of an item 108, such as a cuboid, sphere, cylinder, and so forth. The geometry data may also include information such as length, width, depth, and so forth, of the item 108. Dimensional information in the geometry data may be measured in pixels, centimeters, inches, arbitrary units, and so forth. The geometry data may be for a single item 108, or a package, kit, or other grouping considered to be a single item 108.

The item 108 weight data comprises information indicative of a weight of a single item 108, or a package, kit, or other grouping considered to be a single item 108. The item data 1236 may include other data. For example, the other data may comprise weight distribution of the item 108, point cloud data for the item 108, and so forth.

The item data 1236 may include one or more fixture identifiers (IDs). The fixture ID is indicative of a particular area or volume of fixture such as a shelf that is designated for stowage of the type of item 108. For example, a single shelf may have several lanes, each with a different fixture ID. Each of the different fixture IDs may be associated with a lane having a particular area on the shelf designated for stowage of a particular type of item 108. A single type of item 108 may be associated with a particular fixture ID, a plurality of fixture IDs may be associated with the single type of item 108, more than one type of item 108 may be associated with the particular fixture ID, and so forth.

The item data 1236 may also include quantity data. The quantity data may comprise a count or value indicative of a number of items 108. The count may be a measured or an estimated value. The quantity data may be associated with a particular fixture ID, for an entire facility 1002, and so forth. For example, the same type of item 108 may be stored at different shelves within the facility 1002. The quantity data may indicate the quantity on hand for each of the different fixtures.

The tracking module 134 may access physical layout data 1238 and generate account item data 1240. The tracking module 134 may be configured to determine a location within the facility 1002 of the user 112, a user account associated with the user 112, and so forth. For example, the tracking module 134 may determine that an item 108 has been removed from a lane and placed into the tote 116 based on the fixture data indicative of the user's 112 characteristic data 128 having been received at the lane. The tracking module 134 may then determine that the tote 116 is associated with the user 112 or the user account that represents the user 112. Based on this information, the analysis module 138 may generate the interaction data 140.

The tracking module 134 may also use physical layout data 1238 that is indicative of the arrangement of SFDs 104 with respect to one another, with respect to a reference datum, and so forth. The physical layout data 1238 may also include information such as the physical arrangement of segments 404 within the respective SFDs 104. In some implementations the tracking module 134 may maintain cluster layout data that associates a particular segment 404 within a cluster 402 with a particular portion of the SFD 104. For example, with regard to the cluster 402 depicted in FIG. 2, the first segment 404 in SFD 104(B) may be designated in the cluster layout data as segment 5. Likewise, the first segment 404 in SFD 104(C) may be designated in the cluster layout data as segment 9. The cluster layout data may be changed to provide for dynamic readjustment of clusters 402 as described above.

The analysis module 138 may utilize the device output data 126, fixture data, weight data, capacitance data, item data 1236, and other information to generate interaction data 140. The interaction data 140 is indicative of action such as picking or placing an item 108 for a particular fixture, presence of the user 112 at the fixture, and so forth.

The analysis module 138, or other modules, may be configured to determine portions of the SFDs 104 which are to be deactivated or from which information is to be disregarded. In one implementation, during setup of the system, the antennas 504 of SFDs 104 that are located underneath a fixture may be deactivated. In another implementation, the analysis module 138 may determine SFDs 104 or portions thereof that report presence of an object that is unchanging over long periods of time, such as hours or days. These objects, such as a fixture above the SFD 104, may then be subsequently disregarded and information about these positions may be removed from further processing. If a change is detected, such as when the fixture above the SFD 104 is moved, information about that change may be used to re-enable consideration of data from that SFD 104 or portion thereof.

The inventory management module 1224 may utilize the physical layout data 1238. The physical layout data 1238 may provide information indicative of location of the SFDs 104, where sensors 1012 and the fixtures are in the facility 1002 with respect to one another, FOV of sensors 1012 relative to the fixture, and so forth. For example, the physical layout data 1238 may comprise information representative of a map or floor plan of the facility 1002 with relative positions of the fixtures, location of individual SFDs 104 therein, arrangements of the segments 404, planogram data indicative of how items 108 are to be arranged at the fixtures, and so forth. Continuing the example, the physical layout data 1238 may be based on using the relative arrangement of the SFDs 104 in conjunction with their physical dimensions to specify where the SFDs 104 are placed within the facility 1002.

The physical layout data 1238 may associate a particular fixture ID with other information such as physical location data, sensor position data, sensor direction data, sensor identifiers, and so forth. The physical location data 1238 provides information about where in the facility 1002 objects are, such as the fixture, the sensors 1012, and so forth. In some implementations, the physical location data may be relative to another object. For example, the physical location data may indicate that a particular weight sensor 1012(1), capacitive sensor 1012(2), or image sensor 1012(3) is associated with the shelf or portion thereof.

The account item data 1240 may also be included in the data store 1220 and comprises information indicative of one or more items 108 that are within the custody of a particular user 112, within a particular tote 116, and so forth. For example, the account item data 1240 may comprise a list of the contents of the tote 116. Continuing the example, the list may be further associated with the user account representative of the user 112. In another example, the account item data 1240 may comprise a list of items 108 that the user 112 is carrying. The inventory management module 1224 may use the account item data 1240 to determine subsets of possible items 108 with which the user 112 may have interacted.

The inventory management module 1224, and modules associated therewith, may access sensor data 1230, threshold data 1242, and so forth. The threshold data 1242 may comprise one or more thresholds, ranges, percentages, and so forth, that may be used by the various modules in operation.

The inventory management module 1224 may generate output data 1244. For example, the output data 1244 may include the interaction data 140, inventory levels for individual types of items 108, overall inventory, initiate charges for items 108 that have been acquired by the user 112, and so forth.

The action module 1228 may be configured to initiate or coordinate one or more actions responsive to output data 1244. For example, the action module 1228 may access output data 1244 that indicates a particular fixture is empty and in need of restocking. An action such as a dispatch of a work order or transmitting instructions to a robot may be performed to facilitate restocking of the fixture.

Processing sensor data 1230, such as the image data, may be performed by a module implementing, at least in part, one or more of the following tools or techniques. In one implementation, processing of the image data may be performed, at least in part, using one or more tools available in the OpenCV library as developed by Intel Corporation of Santa Clara, Calif., USA; Willow Garage of Menlo Park, Calif., USA; and Itseez of Nizhny Novgorod, Russia, with information available at www.opencv.org. In another implementation, functions available in the OKAO machine vision library as promulgated by Omron Corporation of Kyoto, Japan, may be used to process the sensor data 1230. In still another implementation, functions such as those in the Machine Vision Toolbox for Matlab (MVTB) available using MATLAB as developed by Math Works, Inc. of Natick, Mass., USA, may be utilized.

Techniques such as artificial neural networks (ANNs), convolutional neural networks (CNNs), active appearance models (AAMs), active shape models (ASMs), principal component analysis (PCA), cascade classifiers, Gaussian Naive Bayes classifiers, and so forth, may also be used to process the sensor data 1230 or other data. For example, the ANN may be a trained using a supervised learning algorithm such that object identifiers are associated with images of particular objects within training images provided to the ANN. Once trained, the ANN may be provided with the sensor data 1230 and the item data 1236 to allow for a determination of similarity between two or more images.

The sensor data 1230 obtained from different sensors 1012 may be used to compare or validate output data 1244. For example, the image data may indicate the presence of a person based on a jacket that is arranged across the back of a chair. However, the user track data 136 may indicate that no user 112 is currently present at that location in the facility 1002. This difference may be used to generate an alarm, notify an associate in the facility 1002, and so forth.

Other data 1246 may be stored in the data store 1220 as well as other modules 1248 in the memory 1216. For example, the other modules 1248 may include a billing module while the other data 1246 may include billing data.

Figure 13:
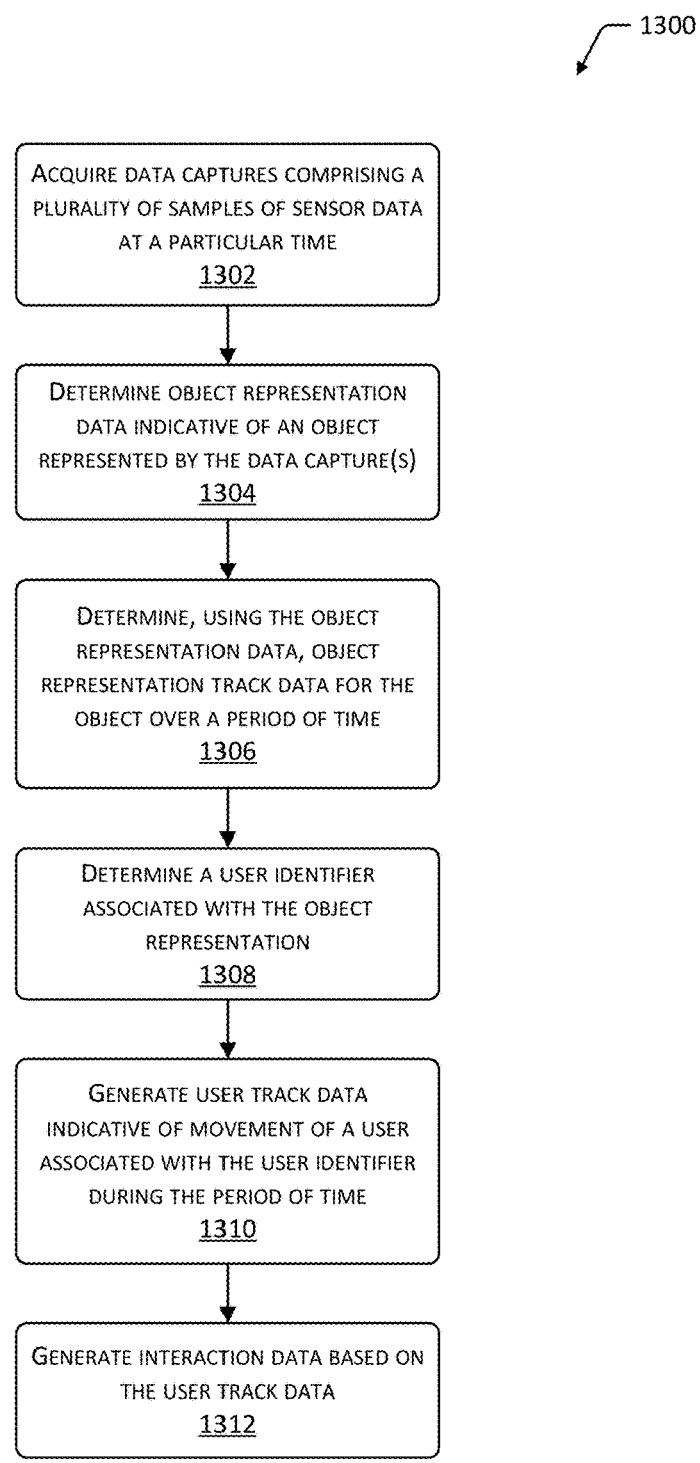
FIG. 13 depicts a flow diagram of a process to generate user track data and interaction data based on information provided by a smart floor, according to some implementations.

FIG. 13 depicts a flow diagram 1300 of a process to generate user track data 136 and interaction data 140 based on information provided by a smart floor, according to some implementations. The process may be implemented at least in part by the tracking module 134.

At 1302, access data captures 204 based on device output data 126 comprising a plurality of samples 202 that have been acquired from a plurality of SFDs 104. For example, the data acquisition module 132 may receive sensor data acquired at a particular time, such as the device output data 126 from a plurality of SFDs 104 and produce the data captures 204.

At 1304, OR data 208 indicative of an OR represented by the device output data 126 may be determined. For example, the OR detection module 206 may process a data capture 204 to determine OR data 208 that is indicative of an OR within the data capture 204.

At 1306, OR track data 216 is determined using the OR data 208. OR track data 216 may be determined for a plurality of data captures 204 that represent samples 202 acquired over a period of time extending from a first time to a second time. For example, the OR track data 216 may comprise time series data that indicates the OR IDs 218, centroid locations 222, and so forth at successive times.

At 1308, a user ID 318 associated with the OR ID 218 is determined. For example, the external identity data 324 may be used to the assert a particular user ID 318 with the OR ID 218. In another example, the feature classifier module 310 may be used to determine the user ID 318 associated with the OR represented by the OR ID 218. In yet another example, the gait data 332 associated with the OR ID 218 may be compared with historical gait data to determine the user ID 318 associated with the OR represented by the OR ID 218.

At 1310, user track data 136 is generated. The user track data 136 may comprise information indicative of movement of a user associated with the user ID 318 during the period of time. For example, the location 320 of the user may be designated as the geometric centroid of the ORs associated with the user ID 318 of that user. The user track data 136 may comprise a time series indicative of the locations 320 at successive times.

At 1312, interaction data 140 may be generated based on the user track data 136. For example, sensors at a particular fixture 1014 may indicate that an item 108 has been picked at a particular time. The user track data 136 may be analyzed to determine the user ID 318 that had a location 320 closest to the particular fixture 1014 at the particular time. Based on this, the account associated with the user ID 318 may be billed for the cost of the item 108.

Figure 14:
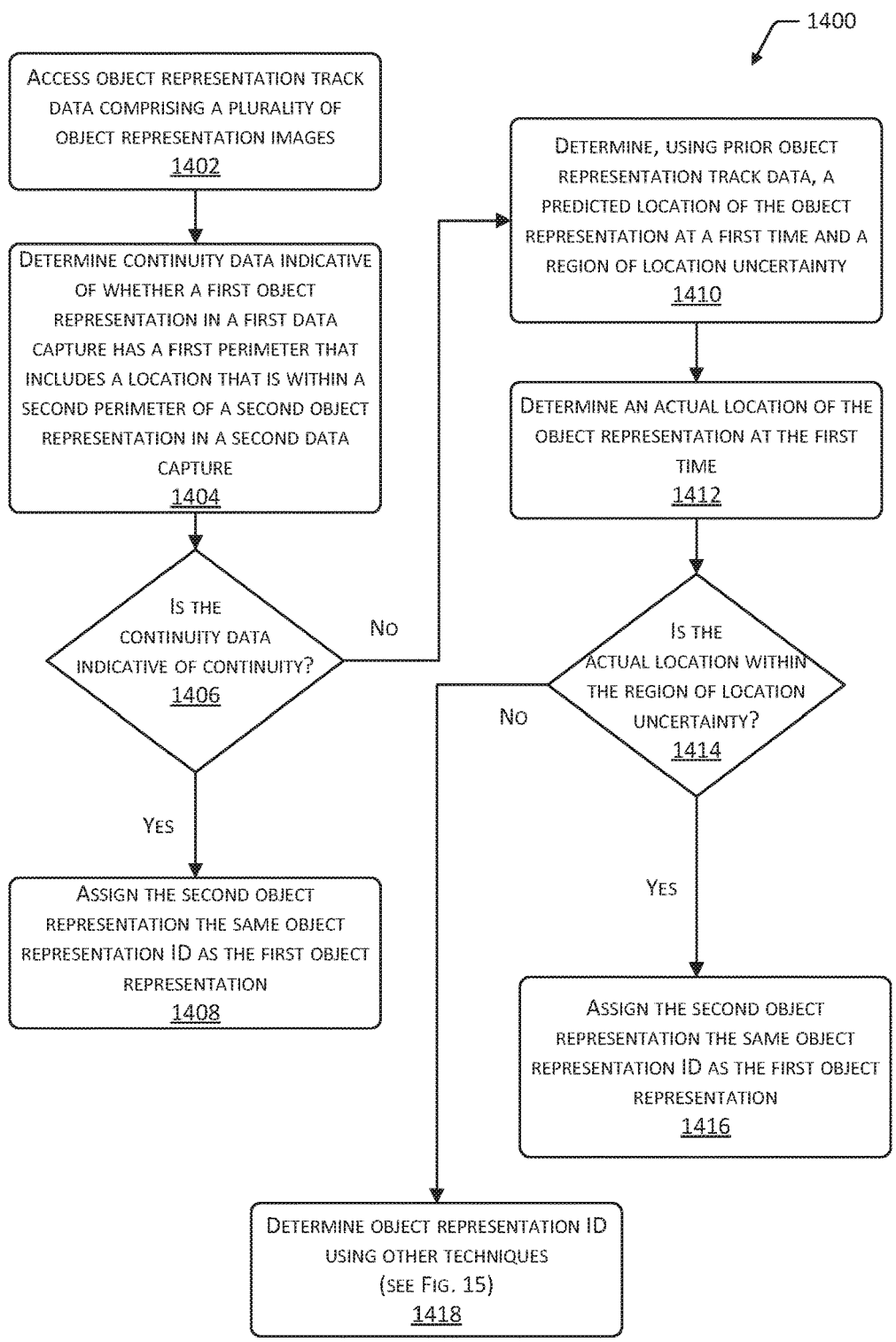
FIG. 14 depicts a flow diagram of a process to determine identifier information associated with ORs, according to some implementations.

FIG. 14 depicts a flow diagram 1400 of a process to determine identifier information associated with ORs, according to some implementations. The process may be implemented at least in part by the tracking module 134.

At 1402, OR track data 216 is accessed. As described above the OR track data 216 may include OR images 226, data indicative of the data captures 204 in which particular ORs occur, and so forth.

At 1404, continuity data is determined that is indicative of whether a first OR in a first data capture 204(1) overlaps a second OR in a second data capture 204(2). For example, as described above the continuity module 212 may determine if a first perimeter of the first OR in the first data capture 204(1) intersects a second perimeter of the second OR in the second data capture 204(2). The first data capture 204(1) and the second data capture 204(2) are successive, in that one of these data captures 204 is based on samples 202 obtained before the other. For example, the first data capture 204(1) may be based on samples 202 obtained at a first time while the second data capture 204(2) is based on samples 202 obtained at a second time that occurred after the first time. For example, the continuity module 212 may determine overlap if the coordinates of a location of a point on the first perimeter is present on or within the second perimeter. Other techniques to determine overlap of the areas or cross-sections of the ORs may also be used.

At 1406, if the continuity data is indicative of continuity between the ORs, the process may proceed to 1408. At 1408, the second OR is assigned the same OR ID 218 as the first OR. For example, because of the overlap in the areas of the ORs in the successive data captures 204, the respective ORs in those data captures 204 may be deemed to be representative of the same object that is moving, and thus the same OR ID 218 is assigned. In some implementations, a user ID 318 that is associated with the first OR may be associated with the second OR.

Returning to 1406, if the continuity data does not indicate continuity between ORs, the process may proceed to 1410. For example, if the user 112 is running, the areas of the ORs representative of the user's 112 feet may not overlap due to the increased speed, the user 112 lifting their feet higher off the floor 102 and thus resulting in the OR disappearing in some data captures 204, and so forth.

At 1410, the prediction module 214 may be used to generate information that predicts the movement of the OR. For example, the prediction module 214 may use the centroid location 222 from OR track data 216 for a series of successive prior times to determine a predicted displacement 808 of the OR in a next data capture 204. For example, the predicted displacement 808 may indicate the OR is expected in the next data capture to move 9 inches along an X axis. With that predicted displacement 808 the predicted location 810 of the OR in that next data capture may be determined. A ROLU 812 may be determined that includes the predicted location 810. For example, the ROLU 812 may be centered on the predicted location 810.

At 1412, the next data capture 204 may then be processed, and the actual location 814 of the OR is determined. At 1414, if the actual location 814 is within the ROLU 812, then the process proceeds to 1416. At 1416, the unidentified OR in that next data capture 204 may be deemed to be the same OR for which the prediction was generated. As a result, that OR may be assigned the OR ID 218 for the OR for which the prediction was generated.

If at 1414 the actual location 814 of the unidentified OR in the next data capture is outside of the ROLU 812, an OR ID 218 is unable to be asserted, and the process may proceed to 1418. At 1418, other techniques may be used to attempt to determine the OR ID 218. As described above, the prediction module 214 may utilize the LQE algorithm, allowing for ongoing predictions to be made and tested. In some implementations the prediction module 214 may operate continuously, in parallel with the continuity module 212.

As described above, in some implementations a user ID 318 may be asserted instead of, or in addition to, the OR ID 218. For example, output from the prediction module 214 may be used to assert a user ID 318 that is associated with the OR ID 218 to the unidentified OR.

Figure 15:
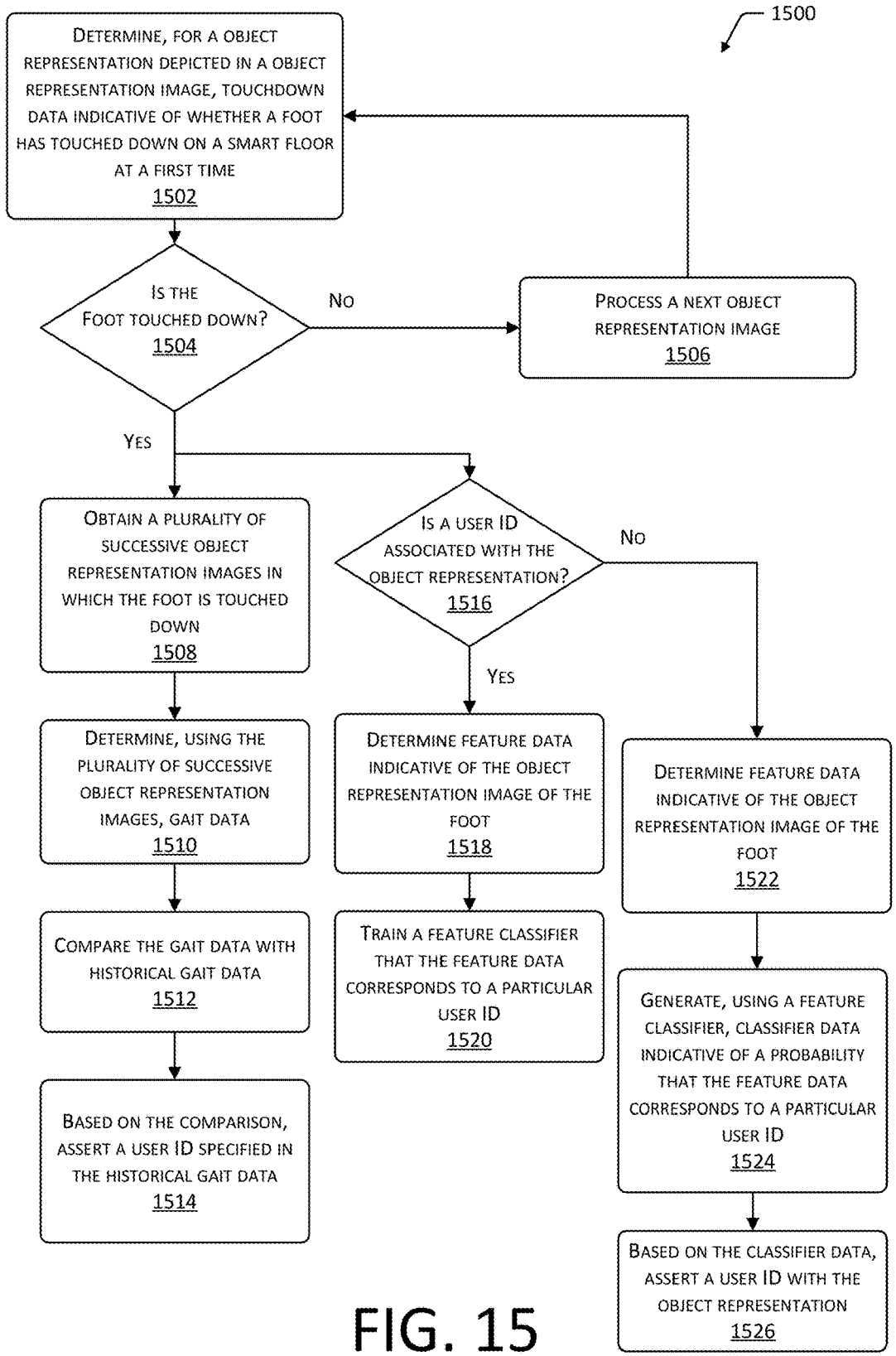
FIG. 15 depicts a flow diagram of a process to further determine identifier information associated with ORs, according to some implementations.

FIG. 15 depicts a flow diagram 1500 of a process to further determine identifier information associated with ORs, according to some implementations. The process may be implemented at least in part by the tracking module 134.

At 1502, touchdown data 304 for an OR depicted in an OR image 226 is determined. As described above, the touchdown detector module 302 may use various techniques to determine if the OR image 226 is representative of a touched down foot. At 1504, if the touchdown data 304 indicates no touchdown is present, the process may proceed to 1506. At 1506, the process may proceed to analyze a different OR image 226. For example, another OR image 226 corresponding to samples 202 acquired at a different time may be processed as described herein. If the touchdown data 304 indicates a touchdown is present, the process may proceed to one or more of 1508 or 1516.

At 1508, a plurality of successive OR images are accessed in which the foot is touched down. For example, a plurality of those OR images 226 from data captures 204 obtained at successive times in which the touchdown data 304 indicates those ORs are touched down may be determined. In some implementations the plurality of successive OR images 226 may comprise those ORs for one foot or both feet of the same user 112. For example, cross-coupling data 224 may be used to determine if two ORs that appear in the same data capture 204 are associated with the same user.

At 1510, the plurality of OR images 226 are processed to determine gait data 332. For example, the gait analysis module 330 may process the successive OR images to determine information such as the length of stride, timing between steps, and so forth.

At 1512, the gait data 332 is compared with historical gait data. For example, one or more values of gait attributes of the gait data 332, such as timing between steps, stride length, touchdown dwell time, acceleration profile, velocity, may be compared with the historical gait data.

At 1514, based on the comparison, if one or more values of one or more attributes of the gait data 332 are within a threshold value with historical gait data, the user ID 318 associated with that historical gait data may be asserted to the one or more ORs.

Other use may be made of the touchdown data 304 as described above. For example, as described above at 1504, if the touchdown data 304 is indicative of a touchdown, the process may proceed to 1516. At 1516, a determination is made as to whether a user ID 318 is associated with the OR ID 218 for the OR that is indicated by the touchdown data 304 as being representative of a touched down foot. If a user ID 318 is associated with the OR ID 218 of the touched down foot, the process may proceed to 1518.

At 1518, feature data 308 about the OR is determined. For example, the OR feature extractor module 306 may be used to generate the feature data 308 as described above in FIG. 3.

At 1520, a feature classifier may be trained using the feature data 308 and the information about one or more of the OR ID 218 or the user ID 318. As described above in FIG. 3, a feature classifier module 310 may implement a Gaussian Naive Bayes classifier that is trained with a plurality of feature data 308 for the same OR, obtained at different times. In other implementations, a convolutional neural network (CNN) may be trained and subsequently used instead of a feature classifier.

Returning to 1516, if no user ID 318 is associated with the OR, the process may proceed to 1522. At 1522, the feature data 308 for an OR that is either unidentified or which is not currently associated with a user ID 318 is determined. For example, the OR image 226 may be processed to determine the feature data 308.

At 1524, the feature classifier is used to generate classifier data 312 that is indicative of a probability that the feature data 308 corresponds to one or more of a particular OR ID 218 or user ID 318. For example, the feature data 308 for the unidentified OR is provided as input to the feature classifier module 310. The feature classifier module 310 provides as output one or more of the OR ID 218 or the user ID 318 and a value indicative of a probability, such as the confidence value.

At 1526, based on the classifier data 312, one or more of an OR ID 218 or a user ID 318 may be asserted with the unidentified OR. For example, if the classifier data 312 exhibits an OR ID 218 that has a confidence value greater than a threshold value, the OR ID 218 may be asserted to the unidentified OR. In some implementations the feature classifier module 310 may produce as output classifier data 312 that is indicative of several possible identifiers and the probability of each. For example, the classifier data 312 may indicate that the unidentified OR has probability of 0.7 of being associated with user ID 318(1) and a probability of 0.3 of being associated with user ID 318(2).

Figure 16:
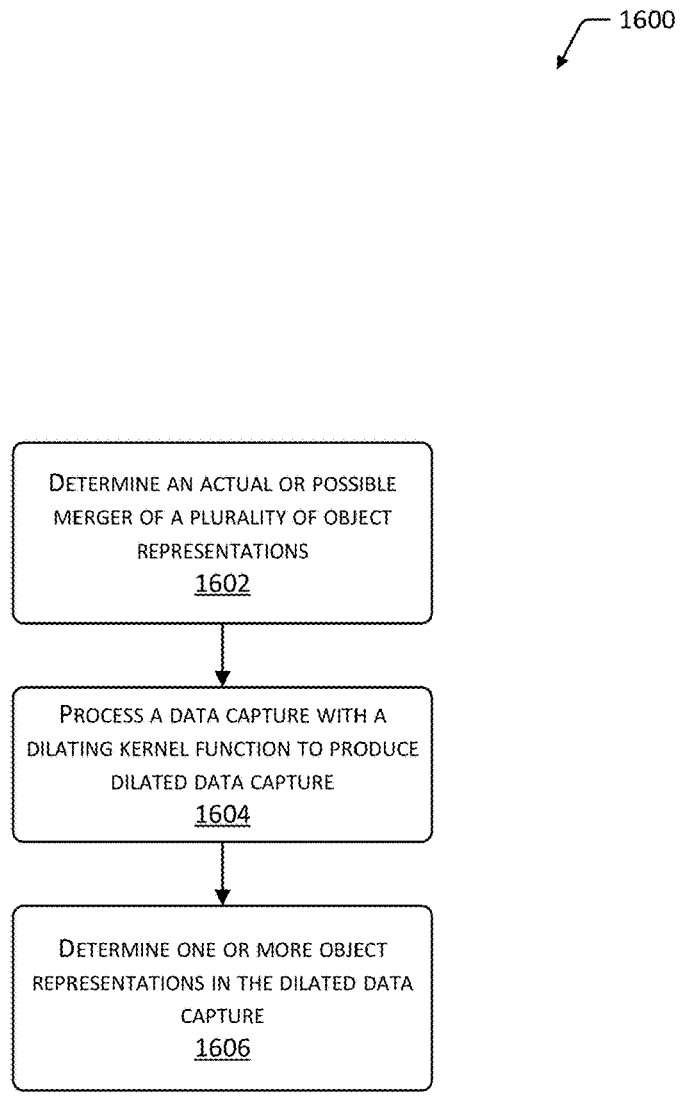
FIG. 16 depicts a flow diagram of a process to resolve merged ORs into separate ORs, according to some implementations.

FIG. 16 depicts a flow diagram 1600 of a process to resolve merged ORs into separate ORs, according to some implementations. The process may be implemented at least in part by the tracking module 134, or a portion thereof such as the OR merger module 230.

At 1602, an actual or possible merger of a plurality of ORs is determined. For example, a count of ORs in a first data capture 204(1) may be greater than a count of ORs in a second data capture 204(2). In another example, OR track data 216 may be processed to determine that between successive data captures two or more ORs are approaching within a threshold distance of one another, or have overlapped. In another example, the ROLUs 812 for two or more ORs may be determined to overlap.

At 1604, the data capture 204 associated with an actual or possible OR merger is processed to attempt to de-merge the ORs. For example, a dilating kernel function may be applied to the data capture 204, producing a dilated data capture 910. As described above, the dilating kernel function may result in a reduction in the area of the ORs, such as a change in the cross section of the ORs in the dilated data capture.

At 1606, one or more ORs are determined in the data capture. For example, the OR detection module 206 may be used to process the dilated data capture 910 and generate OR data 208. This OR data 208 from the dilated data capture 910 may be subsequently processed by the OR tracker module 210. In some implementations, the process may be repeated until the number of ORs present in the dilated data capture is greater, until the number of ORs reaches a maximum number, and so forth.

The system described above may be utilized in a variety of different settings including, but not limited to, commercial, non-commercial, medical, and so forth. For example, the SFDs 104 may be deployed in a home, hospital, care facility, correctional facility, transportation facility, office, and so forth. The tracking module 134 may provide user track data 136 indicative of the location of users 112 within a facility at particular times. In some implementations, the tracking module 134 may provide user track data 136 that is indicative of the identity of a particular user 112. The analysis module 138 may be used to generate output data. This output data may then be used issue a refund in the case of a return of an item 108, issue a charge for an item 108 in the case of a pick from a fixture, and so forth.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A system comprising:
    a plurality of floor devices, each of the plurality of floor devices comprising:
        a flooring material;
        a support structure configured to support the flooring material;
        a first communication interface;
        a transmitter coupled to an antenna, wherein the antenna is underneath the flooring material at a first location;
        a receiver coupled to the antenna;
        a first memory, storing first computer-executable instructions; and
        a first hardware processor to execute the first computer-executable instructions to:
            use the transmitter to transmit a transmitted signal that is radiated by the antenna, wherein the transmitted signal is indicative of the first location;
            use the receiver to receive one or more received signals with the antenna;
            generate first sensor data indicative of a characteristic of the one or more received signals at a first time;
            send the first sensor data using the first communication interface;
            generate second sensor data indicative of a characteristic of the one or more received signals at a second time; and
            send the second sensor data using the first communication interface; and
    a server comprising:
        a second communication interface;
        a second memory, storing second computer-executable instructions; and
        a second hardware processor to execute the second computer-executable instructions to:
            receive the first sensor data and the second sensor data from the plurality of floor devices;
            determine, from the first sensor data, a first object representation that is representative of a first object that is proximate to the flooring material, wherein the first object representation comprises sensor data having values that exceed a threshold value;
            determine, from the second sensor data, a second object representation that is representative of a second object that is proximate to the flooring material, wherein the second object representation comprises sensor data having values that exceed the threshold value;
            determine a first user identifier associated with the first object representation;
            determine that at least a portion of a first perimeter of the first object representation overlaps a portion of a second perimeter of the second object representation; and
            associate the first user identifier with the second object representation.

2. The system of claim 1, wherein the first sensor data is representative of a received signal strength at the first time and the second sensor data is representative of a received signal strength at the second time; and
    the threshold value is indicative of a minimum signal strength representative of detection of an object.

3. The system of claim 1, further comprising:
    determine, from the second sensor data, a third object representation that is representative of a third object that is proximate to the flooring material at the second time, wherein the third object representation comprises sensor data values that exceed the threshold value;
    determine, based on the second sensor data, that a first electromagnetic signal has been transferred from the antenna at the first location that is within the first perimeter of the first object representation, to a second antenna at a second location that is within a third perimeter of the third object representation; and
    determine the first object and the third object are associated with one another.

4. A method comprising:
accessing first sensor data at a first time from one or more sensors at a floor;
accessing second sensor data at a second time from the one or more sensors;
determining, from the first sensor data, a first object representation that is representative of a first object that is above the floor, wherein the first object representation comprises sensor data values that exceed a threshold value;
determining, from the second sensor data, a second object representation that is representative of a second object that is above the floor, wherein the second object representation comprises sensor data values that exceed the threshold value;
determining that the first object and the second object are a same object; and
determining one or more user identifiers associated with the first object representation and the second object representation based on feature data of the first object representation.

5. The method of claim 4, further comprising:
generating user track data indicative of movement with respect to the floor of a user associated with the one or more user identifiers.

6. The method of claim 4, wherein the determining that the first object and the second object are the same object further comprises:
determining a first location that is within a first perimeter of the first object representation; and
determining the first location is within a second perimeter of the second object representation.

7. The method of claim 4, wherein the determining that the first object and the second object are the same object further comprises:
determining a set of prior locations of the first object at times before the second time;
determining a predicted location for the first object at the second time;
determining a region of location uncertainty associated with the predicted location; and
determining that at least a portion of the second object representation overlaps the region of location uncertainty.

8. The method of claim 7, wherein the determining the region of location uncertainty is based on one or more of:
maximum expected displacement of a foot during successive times;
statistical estimation error;
direction of travel indicated by the set of prior locations of the first object; or
speed of the first object during at least a portion of the successive times.

9. The method of claim 4, further comprising:
accessing third sensor data at a third time from the one or more sensors;
determining, from the third sensor data, a third object representation that is representative of a third object that is above the floor, wherein the third object representation comprises sensor data values that exceed the threshold value;
determining a first electromagnetic signal has been transferred, from a first sensor of the one or more sensors that is at a first location within a first perimeter of the first object representation, to a second sensor of the one or more sensors that is at a second location within a second perimeter of the third object representation; and
determining the first object and the third object are associated with one another.

10. The method of claim 4, further comprising:
accessing third sensor data at a third time from the one or more sensors;
determining, from the third sensor data, a third object representation that is representative of a third object that is above the floor, wherein the third object representation comprises sensor data values that exceed the threshold value;
determining the first object is a first foot of a user and the third object is a second foot of the user;
determining, using the first sensor data and the third sensor data, gait data indicative of one or more of:
timing between successive steps of one or more of the first foot and the second foot;
a distance between the first foot and the second foot when both are in contact with the floor; and
a duration of simultaneous contact of the first foot and the second foot with the floor;
accessing historical gait data that associates particular gait data with particular user identifiers;
determining a correspondence between the gait data and the particular gait data of a particular user identifier exceeds a second threshold value; and
associating the particular user identifier with the first object and the second object.

11. The method of claim 4, further comprising:
determining, for the first object representation, a first location at the first time;
determining, for the second object representation, a second location at the second time;
processing the first and second locations using a linear quadratic estimation algorithm to determine a predicted velocity of the first object;
determining the predicted velocity is less than or equal to a threshold; and
generating touchdown data indicative of the first object being stationary at the second time.

12. The method of claim 4, further comprising:
determining a resampled first object representation by resampling the first sensor data from data collected from a first number of samples to a second number of samples, wherein the second number of samples is greater than the first number of samples; and
determining, using the resampled first object representation, the feature data comprising one or more of:
a first cross section of the resampled first object representation, the first cross section comprising each of one or more characteristics having a value that is greater than a first threshold;
a first area of the first cross section;
a volume based on the first cross section and the values of the one or more characteristics within the first cross section;
a centroid of the first cross section;
a location, with respect to the centroid, of one or more local maxima of the values of the one or more characteristics within the first cross section;
a major axis of the first cross section;
a minor axis of the first cross section; or
a heading of the resampled first object representation based on the major axis and the minor axis.

13. The method of claim 12, wherein each sensor in the one or more sensors corresponds to a location of an antenna with respect to the floor and the first sensor data comprises values indicative of at least one or more characteristics of a first signal received by each antenna at the first time and the second sensor data comprises values indicative of at least one or more characteristics of a second signal received by the each antenna at the second time.

14. The method of claim 4, wherein the determining the one or more user identifiers further comprising:
determining the feature data, the feature data indicative of one or more features of the first object representation.

15. The method of claim 4, further comprising:
accessing third sensor data at a third time from the one or more sensors;
determining, from the third sensor data, a third object representation that is representative of a third object that is above the floor and a fourth object representation that is representative of the first object, wherein the third and fourth object representations comprise sensor data values that exceed the threshold value;
determining the third object representation has merged with the fourth object representation at the third time; and
processing the third sensor data with a dilating kernel algorithm to produce dilated data in which the third and fourth object representations are separate from one another, wherein the dilating kernel algorithm convolutes values of the third sensor data with a kernel value.

16. A system comprising:
a first memory, storing first computer-executable instructions; and
a first hardware processor to execute the first computer-executable instructions to:
access first sensor data at a first time from one or more sensors at a floor;
access second sensor data at a second time from the one or more sensors;
determine from the first sensor data, a first object representation that is representative of a first object that is proximate to the floor, wherein the first object representation comprises sensor data values that exceed a threshold value;
determine from the second sensor data, a second object representation that is representative of a second object that is proximate to the floor, wherein the second object representation comprises sensor data values that exceed the threshold value;
determine whether at least a portion of a first perimeter of the first object representation overlaps a portion of a second perimeter of the second object representation; and
determine one or more identifiers associated with the first object representation and the second object representation.

17. The system of claim 16, further comprising:
the first memory, storing second computer-executable instructions; and
the first hardware processor to execute the second computer-executable instructions to:
determine a first location that is within the first perimeter of the first object representation;
determine the first location is within the second perimeter of the second object representation; and
determine that the first object and the second object are the same object.

18. The system of claim 16, further comprising:
the first memory, storing second computer-executable instructions; and
the first hardware processor to execute the second computer-executable instructions to:
determine a set of prior locations of the first object at times before the second time;
determine a predicted location for the first object at the second time;
determine a region of location uncertainty associated with the predicted location;
determine that at least a portion of the second perimeter of the second object representation overlaps the region of location uncertainty; and
determine that the first object and the second object are the same object.

19. The system of claim 16, further comprising:
the first memory, storing second computer-executable instructions; and
the first hardware processor to execute the second computer-executable instructions to:
determine, from the second sensor data, a third object representation that is representative of a third object that is above the floor, wherein the third object representation comprises sensor data values that exceed the threshold value; and
determine, based on the second sensor data, that a first electromagnetic signal has been transferred from a first sensor of the one or more sensors that is at a first location within the first perimeter of the first object representation, to a second sensor of the one or more sensors that is at a second location within a third perimeter of the third object representation; and
determine the first object and the third object are associated with one another.

20. The system of claim 16, further comprising:
a plurality of floor devices, each of the plurality of floor devices comprising:
a flooring material;
a support structure configured to support the flooring material;
a first communication interface;
a transmitter coupled to an antenna, wherein the antenna is underneath the flooring material at a first location;
a receiver coupled to the antenna;
a second memory, storing second computer-executable instructions; and
a second hardware processor to execute the second computer-executable instructions to:
use the transmitter to transmit a transmitted signal that is radiated by the antenna, wherein the transmitted signal is indicative of the first location;
use the receiver to receive one or more received signals with the antenna;
generate the first sensor data indicative of a characteristic of the one or more received signals at the first time;
send the first sensor data using the first communication interface;
generate the second sensor data indicative of a characteristic of the one or more received signals at the second time; and
send the second sensor data using the first communication interface.

21. The system of claim 16, further comprising:
the first memory, storing second computer-executable instructions; and
the first hardware processor to execute the second computer-executable instructions to:
determine, using the first object representation, feature data comprising one or more of:

a first cross section of the first object representation, the first cross section comprising each of one or more characteristics having a value that is greater than a first threshold;

a first area of the first cross section;

a volume based on the first cross section and the value of the each of the one or more characteristics within the first cross section;

a centroid of the first cross section;

a location, with respect to the centroid, of one or more local maxima of the values within the first cross section;

a major axis of the first cross section;

a minor axis of the first cross section; or a heading of the first object representation based on the major axis and the minor axis.

* * * * *